US012702707B2

(12) United States Patent
Friedman et al.

(10) Patent No.: US 12,702,707 B2
(45) **Date of Patent: *Aug. 11, 2026**

(54) MODIFIED mRNA VACCINES ENCODING HERPES SIMPLEX VIRUS GLYCOPROTEINS AND USES THEREOF

(71) Applicant: THE TRUSTEES OF THE UNIVERSITY OF PENNSYLVANIA, Philadelphia, PA (US)

(72) Inventors: Harvey Friedman, Merion, PA (US); Drew Weissman, Wynnewood, PA (US); Sita Awasthi, Bala Cynwyd, PA (US); Gary Cohen, Havertown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,325

(22) Filed: Sep. 19, 2023

(65) Prior Publication Data

US 2024/0024463 A1 Jan. 25, 2024

Related U.S. Application Data

(63) Continuation of application No. 17/349,929, filed on Jun. 17, 2021, now Pat. No. 11,793,872, which is a continuation of application No. 16/640,008, filed as application No. PCT/IB2018/056210 on Aug. 17, 2018, now Pat. No. 11,141,478.

(60) Provisional application No. 62/701,019, filed on Jul. 20, 2018, provisional application No. 62/546,648, filed on Aug. 17, 2017.

(51) Int. Cl.

| | |
|---|---|
| ***A61K 39/245*** | (2006.01) |
| ***A61K 9/00*** | (2006.01) |
| ***A61K 39/00*** | (2006.01) |
| ***A61P 31/22*** | (2006.01) |
| ***C07K 14/005*** | (2006.01) |
| ***C12N 7/00*** | (2006.01) |
| ***C12N 15/11*** | (2006.01) |

(52) U.S. Cl.

CPC .......... *A61K 39/245* (2013.01); *A61K 9/0036* (2013.01); *A61P 31/22* (2018.01); *C07K 14/005* (2013.01); *C12N 7/00* (2013.01); *C12N 15/11* (2013.01); *A61K 2039/53* (2013.01); *A61K 2039/54* (2013.01); *A61K 2039/57* (2013.01); *C12N 2710/16622* (2013.01)

(58) Field of Classification Search

CPC ................ A61K 39/245; A61K 9/0036; A61K 2039/53; A61K 2039/54; A61K 2039/57; A61K 2039/575; A61K 31/7088; A61K 31/7115; A61K 39/12; A61K 2039/70; A61P 31/22; C07K 14/005; C12N 7/00; C12N 15/11; C12N 2710/16622; C12N 2710/16634

See application file for complete search history.

(56) References Cited

U.S. PATENT DOCUMENTS

| | | | | |
|---|---|---|---|---|
| 5,663,153 | A | 9/1997 | Hutcherson et al. | |
| 5,723,335 | A | 3/1998 | Hutcherson et al. | |
| 8,278,036 | B2 | 10/2012 | Kariko et al. | |
| 9,770,463 | B2 | 9/2017 | Gaell | |
| 2008/0102087 | A1 | 5/2008 | Vilalta et al. | |
| 2010/0129877 | A1 | 5/2010 | Sahin et al. | |
| 2010/0330112 | A1 * | 12/2010 | Long ................... | A61K 39/245 424/185.1 |
| 2012/0276209 | A1 | 11/2012 | Pieter et al. | |
| 2012/0328658 | A1 | 12/2012 | Vilata et al. | |
| 2013/0028925 | A1 | 1/2013 | Friedman et al. | |
| 2014/0086947 | A1 * | 3/2014 | Dubensky, Jr. ...... | A61K 39/245 536/23.4 |
| 2016/0074506 | A1 | 3/2016 | Jain et al. | |
| 2018/0303929 | A1 | 10/2018 | Claramella et al. | |
| 2020/0054737 | A1 | 2/2020 | Claramella et al. | |
| 2020/0163878 | A1 | 5/2020 | Baumhof | |

FOREIGN PATENT DOCUMENTS

| | | | |
|---|---|---|---|
| WO | WO 1994/003205 | A1 | 2/1994 |
| WO | WO 1994/020127 | A1 | 9/1994 |
| WO | WO 1995/26204 | | 10/1995 |
| WO | WO 2002/098443 | A2 | 12/2002 |
| WO | WO 2012/016184 | | 2/2012 |
| WO | WO 2015/089340 | A1 | 6/2015 |
| WO | WO 2015/175639 | A1 | 11/2015 |
| WO | WO 2016/005324 | A1 | 1/2016 |
| WO | WO 2016/049705 | A1 | 4/2016 |
| WO | WO 2016/176330 | A1 | 11/2016 |

(Continued)

OTHER PUBLICATIONS

Roychoudhury P, Greninger AL, Jerome KR, Johnston C, Wald A, Xie H. US8 [Human alphaherpesvirus 2]. Envelope glycoprotein E. GenBank: QBH83747.1; Deposit UniProt A0A481TSK5 (A0A481TSK5_HHV2). Mar. 6, 2019. (Year: 2019).*

(Continued)

*Primary Examiner* — Rachel B Gill

(74) *Attorney, Agent, or Firm* — Mark S. Cohen; PEARL COHEN LLP

(57) ABSTRACT

The present invention provides compositions for the prevention and treatment of genital herpes, comprising nucleoside modified mRNAs that encode herpes simplex virus (HSV) glycoproteins, including those involved in virus entry and immune evasion, and methods of use thereof.

17 Claims, 15 Drawing Sheets

Specification includes a Sequence Listing.

(56) References Cited

FOREIGN PATENT DOCUMENTS

| | | | |
|---|---|---|---|
| WO | WO 2017/007616 | 4/2017 | |
| WO | WO 2017/070623 | 4/2017 | |
| WO | WO-2018078053 A1 * | 5/2018 | ............ A61K 31/16 |

OTHER PUBLICATIONS

Meseda CA, Mayer AE Weir JP. Glycoprotein E [Human alphaherpesvirus 2]. GenBank: ABZ04069.1, UniProt B1A187 (B1A187 HHV2). Feb. 10, 2008. (Year: 2008).*

Lasky LA, Dowbenko DJ. Glycoprotein-D [Human alphaherpesvirus 2]. GenBank: AAA45842. 1. (UniProt: P03172, GD_HHV23). Aug. 2, 1993. (Year: 1993).*

Awasthi S, Huang J, Shaw C, Friedman HM. Blocking herpes simplex virus 2 glycoprotein E immune evasion as an approach to enhance efficacy of a trivalent subunit antigen vaccine for genital herpes. J Virol. Aug. 2014;88(15):8421-32. Epub May 14, 2014. (Year: 2014).*

Akinc et al. "Targeted delivery of RNAi therapeutics with endogenous and exogenous ligand-based mechanisms." Molecular Therapy 18.7 (2010): 1357-1364.

Awasthi et al., "A Dual-Modality Herpes Simplex Virus 2 Vaccine for Preventing Genital Herpes by Using Glycoprotein C and D Subunit Antigens to Induce Potent Antibody Responses and Adenovirus Vectors Containing Capsid and Tegument Proteins as T Cell Immunogens." J Virol. Aug. 2015;89(16):8497-509. doi: 10.1128/JVI.01089-15. Epub Jun. 3, 2015. PMID: 26041292; PMCID: PMC4524253.

Awasthi et al., "A trivalent subunit antigen glycoprotein vaccine as immunotherapy for genital herpes in the guinea pig genital infection model." Hum Vaccin Immunother. Dec. 2, 2017;13(12):2785-2793. doi: 10.1080/21645515.2017.1323604. Epub May 8, 2017. PMID: 28481687; PMCID: PMC5718817.

Awasthi et al., An HSV-1 gD mutant virus as an entry-impaired live virus vaccine. Vaccine. Feb. 26, 2008;26(9):1195-203. doi: 10.1016/j.vaccine.2007.12.032. Epub Jan. 14, 2008. PMID: 18243431; PMCID: PMC2680698.

Awasthi et al., An HSV-2 Trivalent Vaccine Is Immunogenic in Rhesus Macaques and Highly Efficacious in Guinea Pigs. PLoS Pathog. Jan. 19, 2017;13(1):e1006141. doi: 10.1371/journal.ppat.1006141. PMID: 28103319; PMCID: PMC5245903.

Awasthi et al., "Better neutralization of herpes simplex virus type 1 (HSV-1) than HSV-2 by antibody from recipients of GlaxoSmithKline HSV-2 glycoprotein D2 subunit vaccine." J Infect Dis. Aug. 15, 2014;210(4):571-5. doi: 10.1093/infdis/jiu177. Epub Mar. 20, 2014. PMID: 24652496; PMCID: PMC4172040.

Awasthi et al., "Blocking Herpes Simplex Virus 2 Glycoprotein E Immune Evasion as an Approach to Enhance Efficacy of a Trivalent Subunit Antigen Vaccine for Genetal Herpes". J. Virol. Aug. 2014, 88(15):8421-32. Epub. May 14, 2014 (year 2014).

Awasthi et al., "Immunization with a vaccine combining herpes simplex virus 2 (HSV-2) glycoprotein C (gC) and gD subunits improves the protection of dorsal root ganglia in mice and reduces the frequency of recurrent vaginal shedding of HSV-2 DNA in guinea pigs compared to immunization with gD alone." J Virol. Oct. 2011;85(20):10472-86. doi: 10.1128/JVI.00849-11. Epub Aug. 3, 2011. PMID: 21813597; PMCID: PMC3187515.

Awasthi et al., "Immunization with HSV-1 glycoprotein C prevents immune evasion from complement and enhances the efficacy of an HSV-1 glycoprotein D subunit vaccine." Vaccine. Nov. 16, 2009;27(49):6845-53. doi: 10.1016/j.vaccine.2009.09.017. Epub Sep. 15, 2009. PMID: 19761834; PMCID: PMC2783579.

Awasthi et al., "Improving immunogenicity and efficacy of vaccines for genital herpes containing herpes simplex virus glycoprotein D. Expert Rev Vaccines." Dec. 2014; 13(12):1475-88. doi: 10.1586/14760584.2014.951336. Epub Aug. 20, 2014. PMID: 25138572.

Awasthi et al., "Protection provided by a herpes simplex virus 2 (HSV-2) glycoprotein C and D subunit antigen vaccine against genital HSV-2 infection in HSV-1-seropositive guinea pigs." J Virol. Feb. 2014;88(4):2000-10. doi: 10.1128/JVI.03163-13. Epub Nov. 27, 2013. PMID: 24284325; PMCID: PMC3911559.

Awasthi et al., Nucleoside-modified mRNA Encoding HSV-2 Glycoroteins C,D, and E Prevent Clinical and Subclinical Genital Herpes. Sci Immunol. Sep. 20, 2019;4(39): eaaw7083. (Year 2019).

Awasthi S, Friedman HM. "A paradigm shift: vaccine-induced antibodies as an immune correlate of protection against herpes simplex virus type 1 genital herpes." J Infect Dis. Mar. 2014;209(6):813-5. doi: 10.1093/infdis/jit658. Epub Nov. 27, 2013. PMID: 24285847.

Awasthi S, Friedman HM."Molecular association of herpes simplex virus type 1 glycoprotein E with membrane protein Us9." Arch Virol. Nov. 2016;161(11):3203-13.doi: 10.1007/s00705-016-3028-z. Epub Aug. 27, 2016. PMID: 27568015; PMCID:PMC5727577.

Basha et al. "Influence of cationic lipid composition on gene silencing properties of lipid nanoparticle formulations of siRNA in antigen-presenting cells." Molecular Therapy 19.12 (2011): 2186-2200.

Basu et al., Characterization of regions of herpes simplex virus type 1 glycoprotein E involved in binding the Fc domain of monomeric IgG and in forming a complex with glycoprotein I. J Immunol. Jan. 1, 1995;154(1):260-7. PMID: 7995945.

Basu et al., Mapping regions of herpes simplex virus type 1 glycoprotein I required for formation of the viral Fc receptor for monomeric IgG. J Immunol. Jan. 1, 1997;158(1):209-15. PMID: 8977192.

Belliveau et al. "Microfluidic synthesis of highly potent limit-size lipid nanoparticles for in vivo delivery of siRNA." Molecular Therapy-Nucleic Acids 1 (2012): e37.

Bonkowsky et al., Herpes Simplex Virus Central Nervous System Relapse During Treatment of Infantile Spasms with Corticotropin. Pediatrics. May 2006; 117(5):e1045-8.

Bose et al., "Role of Nucleolin in Human Parainfluenza Virus Type 3 Infection of Human Lung Epithelial Cells"., J Virol. 78:8146. 2004.

Chang et al., Implications for herpes simplex virus vaccine strategies based on antibodies produced to herpes simplex virus type 1 glycoprotein gC immune evasion domains. Vaccine. Sep. 7, 2005;23(38):4658-65. doi: 10.1016/j.vaccine.2005.04.034. PMID: 15936852.

Jayaraman et al., "Maximizing the Potency if siRNA Lipid Nanoparticles for Hepatic Gene Silencing in Vivo", 2012, Angew Chem Int Ed Engl., 51(34): pp. 8529-8533.

Cuburu et al., "Topical herpes simplex virus 2 (HSV-2) vaccination with human papillomavirus vectors expressing gB/gD ectodomains induces genital-tissue-resident memory CD8+ T cells and reduces genital disease and viral shedding after HSV-2 challenge." Journal of virology 89.1 (2015): 83-96.

Cullis et al., "Lipid Nanoparticle Systems for Enabling Gene Therapies." Molecular therapy, vol. 25, No. 7, Jul. 2017, pp. 1467-1475.

Dong et al., "Poly(d,I-lactide-co-glycolide)/montmorillonite nanoparticles for oral delivery of anticancer drugs". Biomaterials 26(30, pp. 6068-6076. 2005.

Dubin et al., Characterization of domains of herpes simplex virus type 1 glycoprotein E involved in Fc binding activity for immunoglobulin G aggregates. J Virol. Apr. 1994;68(4):2478-85. doi: 10.1128/JVI.68.4.2478-2485.1994. PMID: 7511171; PMCID: PMC236725.

Dubin et al., Herpes simplex virus type 1 encodes two Fc receptors which have different binding characteristics for monomeric immunoglobulin G (IgG) and IgG complexes. J Virol. Jun. 1990;64(6):2725-31. doi:10.1128/JVI.64.6.2725-2731.1990. PMID: 2159540; PMCID: PMC249452.

Dubin et al., "The role of herpes simplex virus glycoproteins in immune evasion." Curr Top Microbiol Immunol. 1992;179:111-20. doi: 10.1007/978-3-642-77247-4_7. PMID: 1323450.

Eisenberg et al., "Complement component C3b binds directly to purified glycoprotein C of herpes simplex virus types 1 and 2." Microb Pathog. Dec. 1987;3(6):423-35. doi: 10.1016/0882-4010(87)90012-x. PMID: 2849025.

Etingin et al., Viral activation of the coagulation cascade: molecular interactions at the surface of infected endothelial cells. Cell. May 18, 1990;61(4):657-62. doi: 10.1016/0092-8674(90)90477-v. PMID: 2160855.

(56) References Cited

OTHER PUBLICATIONS

Friedman et al., "Use of a glucocorticoid-inducible promoter for expression of herpes simplex virus type 1 glycoprotein gC1, a cytotoxic protein in mammalian cells". Mol Cell Biol. Jun. 1989;9(6):2303-14. doi: 10.1128/mcb.9.6.2303. PMID: 2548078; PMCID: PMC362303.
Friedman et al., "Binding of complement component C3b to lycoprotein gC of herpes simplex virus type 1: mapping of gC-binding sites and demonstration of conserved C3b binding in low-passage clinical isolates." J Virol. Nov. 1986;60(2):470-5. doi: 10.1128/JVI.60.2.470-475.1986. PMID: 3021981; PMCID: PMC288914.
Friedman et al., "Glycoprotein C of herpes simplex virus 1 acts as a receptor for the C3b complement component on infected cells." Nature. Jun. 14-20, 1984;309(5969):633-5. doi: 10.1038/309633a0. PMID: 6328323.
Friedman et al., "Immune evasion properties of herpes simplex virus type 1 glycoprotein gC." J Virol. Jul. 1996;70(7):4253-60. doi: 10.1128/JVI.70.7.4253-4260.1996. PMID: 8676446; PMCID: PMC190356.
Friedman et al., "Novel mechanism of antibody-independent complement neutralization of herpes simplex virus type 1." J Immunol. Oct. 15, 2000;165(8):4528-36. doi: 10.4049/jimmunol.165.8.4528. PMID: 11035093.
Friedman et al., Pediatric medulloblastoma xenografts including molecular subgroup 3 and CD133+ and CD15+ cells are sensitive to killing by oncolytic herpes simplex viruses. Neuro Oncol. Feb. 2016;18(2):227-35. doi: 10.1093/neuonc/nov123. Epub Jul. 16, 2015. PMID: 26188016; PMCID: PMC4724175.
Friedman HM. "Immune evasion by herpes simplex virus type 1, strategies for virus survival." Trans Am Clin Climatol Assoc. 2003;114:103-12. PMID: 12813914; PMCID: PMC2194497.
Friedman HM. "Immunologic strategies for herpes vaccination." JAMA. Feb. 9, 2000;283(6):746; author reply 746-7. doi: 10.1001/jama.283.6.746. PMID: 10683051.
Friedman, Frank, I. "HM. A novel function of the herpes simplex virus type 1 Fc receptor: participation in bipolar bridging of antiviral immunoglobulin G." J Virol. Nov. 1989;63(11):4479-88. doi: 10.1128/JVI.63.11.4479-4488.1989. PMID: 2552134; PMCID: PMC251078.
Fries et al., "Glycoprotein C of herpes simplex virus 1 is an inhibitor of the complement cascade." J Immunol. Sep. 1, 1986;137(5):1636-41. PMID: 3018078.
Fruscoloni, et al. "Exonucleolytic degradation of double-stranded RNA by an activity in Xenopus laevis germinal vesicles." Proceedings of the National Academy of Sciences 100.4 (2003): 1639-1644.
Gendelman et al., "A selective defect of interferon alpha production in human immunodeficiency virus-infected monocytes." J Exp Med. Nov. 1, 1990;172(5):1433-42. doi: 10.1084/jem.172.5.1433. Erratum in: J Exp Med. Jan. 1, 1991;173(1):277. PMID: 2264889; PMCID: PMC2188659.
Gerson et al., "Viral infection of vascular endothelial cells alters production of colony-stimulating activity." J Clin Invest. Oct. 1985;76(4):1382-90. doi: 10.1172/JCI112114. PMID: 2414319; PMCID: PMC424082.
Harris et al., "Glycoprotein C of herpes simplex virus type 1 prevents complement-mediated cell lysis and virus neutralization." J Infect Dis. Aug. 1990;162(2):331-7. doi: 10.1093/infdis/162.2.331. PMID: 2165106.
Hook et al., "Blocking antibody access to neutralizing domains on glycoproteins involved in entry as a novel mechanism of immune evasion by herpes simplex virus type 1 glycoproteins C and E." J Virol. Jul. 2008;82(14):6935-41. doi: 10.1128/JVI.02599-07. Epub May 14, 2008. PMID: 18480440; PMCID: PMC2446985.
Hook et al., Herpes simplex virus type 1 and 2 glycoprotein C prevents complement-mediated neutralization induced by natural immunoglobulin M antibody. J Virol. Apr. 2006;80(8):4038-46. doi: 10.1128/JVI.80.8.4038-4046.2006. PMID: 16571820; PMCID: PMC1440426.
International Preliminary Report on Patentability from PCT Patent Application No. PCT/IB2018/56210 dated Feb. 27, 2020.
Judson et al., "Blocking immune evasion as a novel approach for prevention and treatment of herpes simplex virus infection." J Virol. Dec. 2003;77(23):12639-45. doi: 10.1128/jvi.77.23.12639-12645.2003. PMID: 14610186; PMCID: PMC262598.
Karikó et al., Exogenous siRNA mediates sequence-independent gene suppression by signaling through toll-like receptor 3. Cells Tissues Organs. 2004;177(3):132-8. doi: 10.1159/000079987. PMID: 15388987.
Kariko et al., "Increased erythropoiesis in mice injected with submicrogram quantities of pseudouridine-containing mRNA encoding erythropoietin." Molecular therapy 20.5 (2012): 948-953.
Khan et al., "Herpes encephalitis presenting as mild aphasia: Case report." BMC family practice 7.1 (2006): 1-2.
Kielytka et al., "Probing RNA Hairpins with Cobalt(III)hexamine and Electrospray Mass Spectrometry" J. Am Soc Mass Spectrom. Oct. 2006;17(10):1376-1382.
Kober et al., "Optimized signal peptides for the development of high expressing CHO cell lines." Biotechnology and bioengineering 110.4 (2013): 1164-1173.
Langer, Robert. "New methods of drug delivery." Science 249.4976 (1990): 1527-1533.
Lee et al. "Lipid nanoparticle siRNA systems for silencing the androgen receptor in human prostate cancer in vivo." International Journal of Cancer 131.5 (2012): E781-E790.
Leung et al. "Lipid nanoparticles containing siRNA synthesized by microfluidic mixing exhibit an electron-dense nanostructured core." The Journal of Physical Chemistry C 116.34 (2012): 18440-18450.
Lin X, et al., "Immunization strategies to block the herpes simplex virus type 1 immunoglobulin G Fc receptor." J Virol. Mar. 2004;78(5):2562-71. doi: 10.1128/jvi.78.5.2562-2571.2004. PMID: 14963159; PMCID: PMC369259.
Livingston et al., Herpes simplex virus type 1-encoded glycoprotein C contributes to direct coagulation factor X-virus binding. Biochem J. Jan. 15, 2006;393(Pt 2):529-35. doi: 10.1042/BJ20051313. PMID: 16212554; PMCID: PMC1360703.
Löbenberg et. al., "Improved body distribution of 14C-labelled AZT bound to nanoparticles in rats determined by radioluminography." Journal of drug targeting 5.3 (1998): 171-179.
Lopez-Berestein et al. "Liposomes in the therapy of infectious diseases and cancer". AR Liss, 1989, pp. 317-327.
Lubinski et al., Herpes simplex virus type 1 glycoprotein gC mediates immune evasion in vivo. J Virol. Oct. 1998;72(10):8257-63. doi:10.1128/JVI.72.10.8257-8263.1998. PMID: 9733869; PMCID: PMC110183.
Lubinski et al., "In vivo role of complement-interacting domains of herpes simplex virus type 1 glycoprotein gC." J Exp Med. Dec. 1999;190(11):1637-46. doi: 10.1084/jem.190.11.1637. Erratum in: J Exp Med Feb. 21, 2000;191(4):following 746. PMID: 10587354; PMCID: PMC2195732.
Lubinski et al., "The herpes simplex virus 1 IgG fc receptor blocks antibody-mediated complement activation and antibody-dependent cellular cytotoxicity in vivo". J Virol. Apr. 2011;85(7):3239-49. doi: 10.1128/JVI.02509-10. Epub Jan. 12, 2011. PMID: 21228231;PMCID: PMC3067879.
Lubinski et al., "Viral interference with antibody and complement." Semin Cell Dev Biol. Jun. 1998;9(3):329-37. doi: 10.1006/scdb.1998.0242. PMID: 9665870; PMCID: PMC7172161.
Lubinski e al., "Herpes simplex virus type 1 evades the effects of antibody and complement in vivo." J Virol. Sep. 2002;76(18):9232-41. doi: 10.1128/jvi.76.18.9232-9241.2002. PMID: 12186907; PMCID: PMC136467.
Lubinski et al., "Blocking immune evasion as a novel approach for prevention and treatment of herpes simplex virus infection." J Virol. Dec. 2003;77(23):12639-45. doi: 10.1128/jvi.77.23.12639-12645.2003. PMID: 14610186; PMCID: PMC262598.
Maheshwari et al., Defective transport of herpes simplex virus glycoprotein in interferon-treated cells: role of intracellular pH. J Interferon Res. Dec. 1994;14(6):319-24. doi: 10.1089/jir.1994.14.319. PMID: 7897250.
Maier et al. "Biodegradable lipids enabling rapidly eliminated lipid nanoparticles for systemic delivery of RNAi therapeutics." Molecular Therapy 21.8 (2013): 1570-1578.

(56) References Cited

OTHER PUBLICATIONS

Mui et al. "Influence of polyethylene glycol lipid desorption rates on pharmacokinetics and pharmacodynamics of siRNA lipid nanoparticles." Molecular Therapy-Nucleic Acids 2 (2013): e139.
Nagot et al. "Reduction of HIV-1 RNA levels with therapy to suppress herpes simplex virus." New England Journal of Medicine 356.8 (2007): 790-799.
Ngosuwan et al. "Roles of cytosolic Hsp70 and Hsp40 molecular chaperones in post-translational translocation of presecretory proteins into the endoplasmic reticulum." Journal of Biological Chemistry 278.9 (2003): 7034-7042.
Ouedraogo et al.,"Impact on suppressive herpes therapy on gential HIV-1 RNA among women taking antiretrovial therapy: a randomized controlle trial." AIDS. Nov. 28, 2006;20(18):2305-13.
Pardi et al., "Administration of nucleoside-modified mRNA encoding broadly neutralizing antibody protects humanized mice from HIV-1 challenge", Nat Commun. Mar. 2, 2017;8:14630.
Pressey et al., "CD133 marks a myogenically primitive subpopulation in rhabdomyosarcoma cell lines that are relatively chemoresistant but sensitive to mutant HSV." Pediatr Blood Cancer. Jan. 2013;60(1):45-52. doi: 10.1002/pbc.24117. Epub Mar. 9, 2012. PMID: 22408058; PMCID: PMC3374896.
Ratajczyk E et al., The role of TNF-α inhibitor in glioma virotherapy: a mathematical model. Math Biosci Eng. Feb. 1, 2017;14(1):305-319. doi: 10.3934/mbe.2017020. PMID: 27879135.
Richner et al., "Modified mRNA Vaccines Protect Against Zika Virus Infection". Cell Mar. 9, 2017. 168(6):1114-1125.e10.doi: 10.1016/j.cell.2017.02.17. Epub. Feb. 17, 2017. (year 2017).
Rux et al., Kinetic analysis of glycoprotein C of herpes simplex virus types 1 and 2 binding to heparin, heparan sulfate, and complement component C3b. Virology. Mar. 15, 2002;294(2):324-32. doi: 10.1006/viro.2001.1326. PMID: 12009874.
Sakuma et al. "Mucoadhesion of polystyrene nanoparticles having surface hydrophilic polymeric chains in the gastrointestinal tract." International journal of pharmaceutics 177.2 (1999): 161-172.
Saldanha et al., "Herpes simplex virus type 1 glycoprotein E domains involved in virus spread and disease." J Virol. Aug. 2000;74(15):6712-9. doi: 10.1128/jvi.74.15.6712-6719.2000. PMID: 10888608; PMCID: PMC112186.
Schlake et al., "Developing mRNA-vaccine technologies." RNA biology 9.11 (2012): 1319-1330.
Seidel-Dugan et al., "Identification of C3b-binding regions on herpes simplex virus type 2 glycoprotein C." J Virol. May 1990;64(5):1897-906. doi: 10.1128/JVI.64.5.1897-1906.1990. PMID: 2157859; PMCID: PMC249343.
Semple et al. "Rational design of cationic lipids for siRNA delivery." Nature biotechnology 28.2 (2010): 172-176.
Shedlock et al., "DNA vaccination: antigen presentation and the induction of immunity." Journal of leukocyte biology 68.6 (2000): 793-806.
Singh et al., Mechanism of enhancement of the antiviral action of interferon against herpes simplex virus-1 by chloroquine. J Interferon Cytokine Res. Sep. 1996;16(9):725-31. doi: 10.1089/jir.1996.16.725. PMID: 8887057.
Smiley et al., "Binding of complement component C3b to glycoprotein C is modulated by sialic acid on herpes simplex virus type 1-infected cells." J Virol. Sep. 1985;55(3):857-61. doi: 10.1128/JVI.55.3.857-861.1985. PMID: 2991604; PMCID: PMC255075.
Smiley et al., "Herpes simplex virus type 1 infection of endothelial, epithelial, and fibroblast cells induces a receptor for C3b." J Immunol. Apr. 1985;134(4):2673-8. PMID: 2982950.
Sutherland et al., "Herpes simplex virus type 1-encoded glycoprotein C enhances coagulation factor VIIa activity on the virus." Thromb Haemost. Nov. 2004;92(5):947-55. doi: 10.1160/TH04-04-0242. PMID: 15543320.
Sutherland et al., "Thrombin enhances herpes simplex virus infection of cells involving protease-activated receptor 1." J Thromb Haemost. May 2007;5(5):1055-61. doi: 10.1111/j.1538-7836.2007.02441.x. PMID: 17461934.
Syverton et al., "Studies on herpes simplex virus. III. The effects of roentgen radiation, cortisone and gastric mucin upon the infectivity of herpes simplex virus for laboratory mice." J Infect Dis. Jan.-Feb. 1955;96(1):9-13. doi: 10.1093/infdis/96.1.9. PMID: 14354231.
Tal-Singer et al., Herpes simplex virus glycoprotein C is a receptor for complement component iC3b. J Infect Dis. Oct. 1991;164(4):750-3. doi:10.1093/infdis/164.4.750. PMID: 1654359.
Tam et al. "Small molecule ligands for enhanced intracellular delivery of lipid nanoparticle formulations of siRNA." *Nanomedicine: Nanotechnology, Biology and Medicine* 9.5 (2013): 665-674.
Treat et al., "Liposomes in the Therapy of Infectious Disease and Cancer", Lopez-Berestein and Filder (eds.), Liss, New York, pp. 353-365 (1989).
Virovic et al. "Novel delivery methods for treatment of viral hepatitis: an update." Expert opinion on drug delivery 2.4 (2005): 707-717.
Wall et al. "Effective translation of the second cistron in two *Drosophila* dicistronic transcripts is determined by the absence of in-frame AUG codons in the first cistron." Journal of Biological Chemistry 280.30 (2005): 27670-27678.
Wang et al., "Herpes simplex virus type 1 glycoprotein e is required for axonal localization of capsid, tegument, and membrane glycoproteins." J Virol. Nov. 2005;79(21):13362-72. doi:10.1128/JVI.79.21.13362-13372.2005. PMID: 16227258; PMCID: PMC1262596.
Weeks et al., Laminin reduces HSV-1 spread from cell to cell in human keratinocyte cultures. Biochem Biophys Res Commun. Jan. 13, 1997;230(2):466-9. doi: 10.1006/bbrc.1996.5925. PMID: 9016804.
Witmer et al., "Cytotoxic T lymphocytes specific for herpes simplex virus (HSV) studied using adenovirus vectors expressing HSV glycoproteins." J Gen Virol. Feb. 1990;71 ( Pt 2):387-96. doi: 10.1099/0022-1317-71-2-387. PMID: 2155292.
Zajac et al., Increased adherence of human granulocytes to herpes simplex virus type 1 infected endothelial cells. In Vitro Cell Dev Biol. Apr. 1988;24(4):321-5. doi: 10.1007/BF02628834. PMID: 2835355.
Ziaie et al., "Suppression of matrix protein synthesis by herpes simplex virus type 1 in human endothelial cells." Coll Relat Res. Oct. 1986;6(4):333-49. doi: 10.1016/s0174-173x(86)80004-8. PMID: 3028708.
Zhang et al., "Alteration in the IL-2 signal peptide affects secretion of proteins in vitro and in vivo." The Journal of Gene Medicine: a cross-disciplinary journal for research on the science of gene transfer and its clinical applications 7.3 (2005): 354-365.
Zimmermann et al. "Electrolyte-and pH-stabilities of aqueous solid lipid nanoparticle (SLN™) dispersions in artificial gastrointestinal media." European Journal of Pharmaceutics and Biopharmaceutics 52.203 (2001): 203-210.
Busch et al. "Degenerate binding of immunogenic peptides to HLA-DR proteins on B cell surfaces" International immunology. 1990;2(5):443-51.
Ceppellini et al. "Binding of labelled influenza matrix peptide to HLA DR in living B lymphoid cells" Nature. Jun. 1, 1989;339(6223):392-4.
Cerundolo et al. "The binding affinity and dissociation rates of peptides for class I major histocompatibility complex molecules" European journal of immunology. Sep. 1991;21(9):2069-75.
Christinck et al. "Peptide binding to class I MHC on living cells and quantitation of complexes required for CTL lysis" Nature. Jul. 4, 1991;352(6330):67-70.
Daffis et al. "2'-O methylation of the viral mRNA cap evades host restriction by IFIT family members" Nature. 2010;468(7322):452.
Decroly et al. "Conventional and unconventional mechanisms for capping viral mRNA" Nature reviews. Microbiology. Dec. 5, 2011;10(1):51-65.
Del Guerci et al. "Binding of a peptide antigen to multiple HLA alleles allows definition of an A2-like supertype" Journal of immunology (Baltimore, Md.: 1950). Jan. 15, 1995;154(2):685-93.
Diamond MS. "IFIT1: a dual sensor and effector molecule that detects non-2'-O methylated viral RNA and inhibits its translation" Cytokine & growth factor reviews. Oct. 2014;25(5):543-50.

(56) References Cited

OTHER PUBLICATIONS

Dolan et al. RecName: Full=Envelope glycoprotein D; Short=gD; Flags: Precursor UniProtKB/Swiss-Prot: Q69467.1. Updated Dec. 14, 2022. First deposit Nov. 11, 2005.
European Search Report from European Patent Application No. 231691551 dated Feb. 9, 2024.
Fath et al. "Multiparameter RNA and codon optimization: a standardized tool to assess and enhance autologous mammalian gene expression" PloS one. Mar. 3, 2011;6(3):e17596.
Graf et al. "Codon-optimized genes that enable increased heterologous expression in mammalian cells and elicit efficient immune responses in mice after vaccination of naked DNA" Methods in molecular medicine. 2004;94:197-210.
Hammer J. "Precuse Oreductuib if nahir gusticinoatubukuty complex class II-peptide interaction based on peptide side chain scanning" J. Exp. Med. 1994;180:2353.
Hill et al. "Conformational and structural characteristics of peptides binding to HLA-DR molecules" Journal of immunology (Baltimore, Md.: 1950). Jul. 1, 1991;147(1):189-97.
Hill et al. "Exploration of requirements for peptide binding to HLA DRB1* 0101 and DRB1* 0401" Journal of immunology (Baltimore, Md.: 1950). Mar. 15, 1994;152(6):2890-8.
Holtkamp et al. "Modification of antigen-encoding RNA increases stability, translational efficacy, and T-cell stimulatory capacity of dendritic cells" Blood. Dec. 15, 2006;108(13):4009-17.
International Search Report and Written Opinion from PCT Patent Application No. PCT/IB2018/56210 dated Dec. 13, 2018.
Johnston et al. envelope glycoprotein E [Human alphaherpesvirus 2]. GenBank: AQZ58667.1. Updated Aug. 14, 2017; first deposit Mar. 26, 2017.
Khilko et al. "Direct detection of major histocompatibility complex class I binding to antigenic peptides using surface plasmon resonance. Peptide immobilization and characterization of binding specificity" The Journal of biological chemistry. Jul. 25, 1993;268(21):15425-34.
Ljunggren et al. "Empty MHC class I molecules come out in the cold" Nature. Aug. 2, 1990;346(6283):476-80.
Marshall et al. "Role of the polymorphic residues in HLA-DR molecules in allele-specific binding of peptide ligands" Journal of immunology (Baltimore, Md.: 1950). May 15, 1994;152(10):4946-57.
Maruggi et al. "Immunogenicity and protective efficacy induced by self-amplifying mRNA vaccines encoding bacterial antigens" Vaccine. Jan. 5, 2017;35(2):361-8.
Meyers et al. "Row replacement algorithms for screen editors" ACM Transactions on Programming Languages and Systems (TOPLAS). Jan. 1, 1989;11(1):33-56.
Pan et al. "Inhibition of II-type Herpes Simplex Virus by UL5-targeted Small Interfering RNA" Chinese Journal of Tissue Engineering Research, Sep. 9, 2012; 16(37):6931-6936.
Parker et al. "The beta 2-microglobulin dissociation rate is an accurate measure of the stability of MHC class I heterotrimers and depends on which peptide is bound" Journal of immunology (Baltimore, Md.: 1950). Sep. 15, 1992;149(6):1896-904.
Raab et al. "The GeneOptimizer Algorithm: using a sliding window approach to cope with the vast sequence space in multiparameter DNA sequence optimization" Systems and synthetic biology. Sep. 2010;4(3):215-25.
Ramanathan et al. "mRNA capping: biological functions and applications" Nucleic acids research. Sep. 19, 2016;44(16):7511-26.
Reay et al. "pH dependence and exchange of high and low responder peptides binding to a class II MHC molecule" The EMBO journal. Aug. 1992;11(8):2829-39.
Schumacher et al. "Direct binding of peptide to empty MHC class I molecules on intact cells and in vitro" Cell. Aug. 10, 1990;62(3):563-7.
Sette et al. "Peptide binding to the most frequent HLA-A class I alleles measured by quantitative molecular binding assays" Molecular immunology. Aug. 1994;31(11):813-22.
Sidney et al. "Measurement of MHC/peptide interactions by gel filtration or monoclonal antibody capture" Current protocols in immunology. Feb. 2013;100(1):18-3.
Sidney et al. "Several HLA alleles share overlapping peptide specificities" Journal of immunology (Baltimore, Md.: 1950). Jan. 1, 1995;154(1):247-59.
Supplemental European Search Report from European Patent Application No. 18846061.2 dated Apr. 14, 2021.
Swain et al. RecName: Full=Envelope glycoprotein C; Flags: Precursor, UniProtKB/Swiss-Prot: P06475.1; Updated Dec. 14, 2022. First deposit Apr. 24, 1993.
Townsend et al. "Assembly of MHC class I molecules analyzed in vitro" Cell. Jul. 27, 1990;62(2):285-95.
Züst et al. "Ribose 2'-O-methylation provides a molecular signature for the distinction of self and non-self mRNA dependent on the RNA sensor Mda5" Nature Immunology. 2011;12(2):137.

* cited by examiner

Weight loss and neurological signs

| Condition | Mock | gD2 | Tri – individual | Tri - combined |
|---|---|---|---|---|
| Weight loss/gain | -15% | +5% | +5% | +4% |
| Neurological signs | 100% | 0% | 0% | 0% |

Germinal center B cells

Number of GC B cells in spleen 1,200,000
900,000
600,000
300,000
0 naive
Poly(C) mRNA-LNP
Trivalent mRNA-LNP

*
*

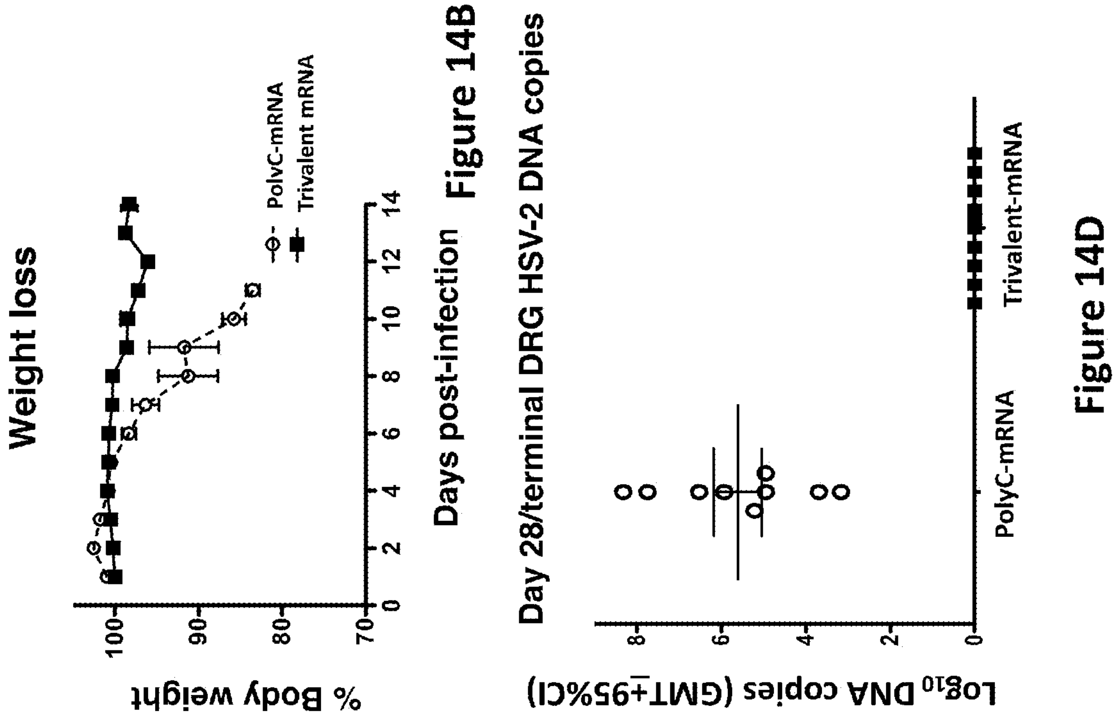
Weight loss
% Body weight
Days post-infection
PolyC-mRNA
Trivalent mRNA
Figure 14B
Day 28/terminal DRG HSV-2 DNA copies
Log10 DNA copies (GMT+95%CI)
PolyC-mRNA
Trivalent-mRNA
Figure 14D
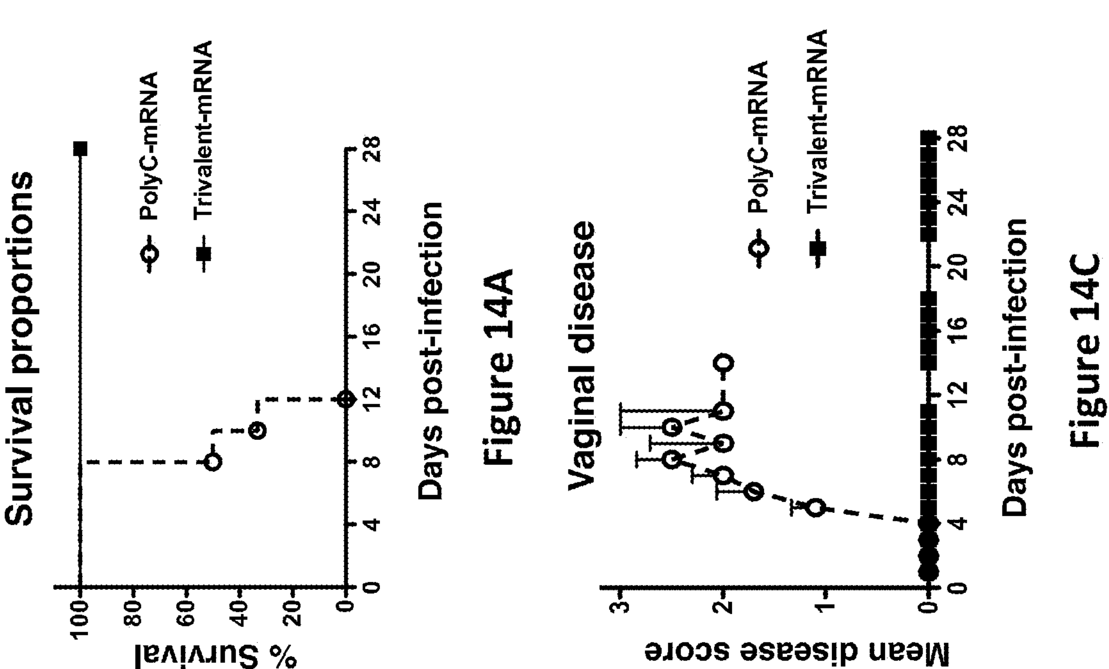
Survival proportions
% Survival
Days post-infection
PolyC-mRNA
Trivalent-mRNA
Figure 14A
Vaginal disease
Mean disease score
Days post-infection
PolyC-mRNA
Trivalent-mRNA
Figure 14C

SEQUENCE LISTING

```
Sequence total quantity: 24
SEQ ID NO: 1           moltype = RNA  length = 1386
FEATURE                Location/Qualifiers
misc_feature           1..1386
                       note = All uridine residues are 1-methyl-pseudouridine -
                        encodes glycoprotein D from Herpes Simplex Virus-1
source                 1..1386
                       mol_type = other RNA
                       organism = synthetic construct
SEQUENCE: 1
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcatgcgcat gcagctgctg ctgctgatcg ccctgtccct  180
ggccctggtg accaactcca agtacgccct ggccgacgcc tccctgaaga tggccgaccc  240
caaccgcttc cgcggcaagg acctgcccgt gctggaccag ctgaccgacc cccccggcgt  300
gcgccgcgtg taccacatcc aggccggcct gcccgacccc ttccagcccc cctccctgcc  360
catcaccgtg tactacgccg tgctggagcg cgcctgccgc tccgtgctgc tgaacgcccc  420
ctccgaggcc ccccagatcg tgcgcggcgc ctccgaggac gtgcgcaagc agccctacaa  480
cctgaccatc gcctggttcc gcatgggcgg caactgcgcc atccccatca ccgtgatgga  540
gtacaccgag tgctcctaca acaagtccct gggcgcctgc cccatccgca cccagccccg  600
ctggaactac tacgactcct tctccgccgt gtccgaggac aacctgggct tcctgatgca  660
cgcccccgcc ttcgagaccg ccggcaccta cctgcgcctg gtgaagatca acgactggac  720
cgagatcacc cagttcatcc tggagcaccg cgccaagggc tcctgcaagt acgccctgcc  780
cctgcgcatc ccccccctccg cctgcctgtc cccccaggcc taccagcagg gcgtgaccgt  840
ggactccatc ggcatgctgc cccgcttcat ccccgagaac cagcgcaccg tggccgtgta  900
ctccctgaag atcgccggct ggcacggccc caaggccccc tacacctcca ccctgctgcc  960
ccccgagctg tccgagaccc ccaacgccac ccagcccgag ctggcccccg aggaccccga  1020
ggactccgcc ctgctggagg accccgtggg caccgtggcc ccccagatcc cccccaactg  1080
gcacatcccc tccatccagg acgccgccac cccctactaa ctagtagtga ctgactagga  1140
tctggttacc actaaaccag cctcaagaac acccgaatgg agtctctaag ctacataata  1200
ccaacttaca cttacaaaat gttgtccccc aaaatgtagc cattcgtatc tgctcctaat  1260
aaaaagaaag tttcttcaca ttctaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaac                                                             1386

SEQ ID NO: 2           moltype = AA  length = 306
FEATURE                Location/Qualifiers
source                 1..306
                       mol_type = protein
                       organism = Human alphaherpesvirus 1
SEQUENCE: 2
KYALADASLK MADPNRFRGK DLPVLDQLTD PPGVRRVYHI QAGLPDPFQP PSLPITVYYA  60
VLERACRSVL LNAPSEAPQI VRGASEDVRK QPYNLTIAWF RMGGNCAIPI TVMEYTECSY  120
NKSLGACPIR TQPRWNYYDS FSAVSEDNLG FLMHAPAFET AGTYLRLVKI NDWTEITQFI  180
LEHRAKGSCK YALPLRIPPS ACLSPQAYQQ GVTVDSIGML PRFIPENQRT VAVYSLKIAG  240
WHGPKAPYTS TLLPPELSET PNATQPELAP EDPEDSALLE DPVGTVAPQI PPNWHIPSIQ  300
DAATPY                                                             306

SEQ ID NO: 3           moltype = AA  length = 394
FEATURE                Location/Qualifiers
source                 1..394
                       mol_type = protein
```

```
                         organism = Human alphaherpesvirus 1
SEQUENCE: 3
MGGAAARLGA VILFVVIVGL HGVRGKYALA DASLKLADPN RFRRKDLPVL DQLTDPPGVR  60
RVYHIQAGLP DPFQPPSLPI TVYYAVLERA CRSVLLNAPS EAPQIVRGAS EDVRKQPYNL  120
TIAWFRMGGN CAIPITVMEY TECSYNKSLG ACPIRTQPRW NYYDSFSAVS EDNLGFLMHA  180
PAFETAGTYL RLVKINDWTE ITQFILEHRA KGSCKYALPL RIPPSACLSP QAYQQGVTVD  240
SIGMLPRFIP ENQRTVAVYS LKIAGWHGPK APYTSTLLPP ELSETPNATQ PELAPEAPED  300
SALLEDPVGT VAPQIPPNWH IPSIQDAATP YHPPATPNNM GLIAGAVGGS LLAALVICGI  360
VYWMRRRTQK APKRIRLPHI REDDQPSSHQ PLFY                              394

SEQ ID NO: 4             moltype = RNA  length = 1386
FEATURE                  Location/Qualifiers
misc_feature             1..1386
                         note = All uridine residues are 1-methyl-pseudouridine -
                          encodes glycoprotein D from Herpes Simplex Virus-2
source                   1..1386
                         mol_type = other RNA
                         organism = synthetic construct
SEQUENCE: 4
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcatgacccg cctgaccgtg ctggccctgc tggccggcct  180
gctggcctcc tcccgcgcca agtacgccct ggccgacccc tccctgaaga tggccgaccc  240
caaccgcttc cgcggcaaga acctgcccgt gctggaccag ctgaccgacc cccccggcgt  300
gaagcgcgtg taccacatcc agccctccct ggaggacccc ttccagcccc cctccatccc  360
catcaccgtg tactacgccg tgctggagcg cgcctgccgc tccgtgctgc tgcacgcccc  420
ctccgaggcc ccccagatcg tgcgcggcgc ctccgacgag gcccgcaagc acacctacaa  480
cctgaccatc gcctggtacc gcatgggcga caactgcgcc atccccatca ccgtgatgga  540
gtacaccgag tgcccctaca acaagtccct gggcgtgtgc cccatccgca cccagccccg  600
ctggtcctac tacgactcct tctccgccgt gtccgaggac aacctgggct tcctgatgca  660
cgcccccgcc ttcgagaccg ccggcaccta cctgcgcctg gtgaagatca acgactggac  720
cgagatcacc cagttcatcc tggagcaccg cgcccgcgcc tcctgcaagt acgccctgcc  780
cctgcgcatc ccccccgccg cctgcctgac ctccaaggcc taccagcagg gcgtgaccgt  840
ggactccatc ggcatgctgc cccgcttcat ccccgagaac cagcgcaccg tggccctgta  900
ctccctgaag atcgccggct ggcacggccc caagcccccc tacacctcca ccctgctgcc  960
ccccgagctg tccgacacca ccaacgccac ccagcccgag ctggtgcccg aggaccccga  1020
ggactccgcc ctgctggagg accccgccgg caccgtgtcc tcccagatcc cccccaactg  1080
gcacatcccc tccatccagg acgtggcccc ccaccactaa ctagtagtga ctgactagga  1140
tctggttacc actaaaccag cctcaagaac acccgaatgg agtctctaag ctacataata  1200
ccaacttaca cttacaaaat gttgtccccc aaaatgtagc cattcgtatc tgctcctaat  1260
aaaaagaaag tttcttcaca ttctaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaac                                                             1386

SEQ ID NO: 5             moltype = AA  length = 306
FEATURE                  Location/Qualifiers
source                   1..306
                         mol_type = protein
                         organism = Human alphaherpesvirus 2
SEQUENCE: 5
KYALADPSLK MADPNRFRGK NLPVLDQLTD PPGVKRVYHI QPSLEDPFQP PSIPITVYYA  60
VLERACRSVL LHAPSEAPQI VRGASDEARK HTYNLTIAWY RMGDNCAIPI TVMEYTECPY  120
NKSLGVCPIR TQPRWSYYDS FSAVSEDNLG FLMHAPAFET AGTYLRLVKI NDWTEITQFI  180
LEHRARASCK YALPLRIPPA ACLTSKAYQQ GVTVDSIGML PRFIPENQRT VALYSLKIAG  240
WHGPKPPYTS TLLPPELSDT TNATQPELVP EDPEDSALLE DPAGTVSSQI PPNWHIPSIQ  300
DVAPHH                                                             306

SEQ ID NO: 6             moltype = AA  length = 393
FEATURE                  Location/Qualifiers
source                   1..393
                         mol_type = protein
                         organism = Human alphaherpesvirus 2
SEQUENCE: 6
MGRLTSGVGT AALLVVAVGL RVVCAKYALA DPSLKMADPN RFRGKNLPVL DQLTDPPGVK  60
RVYHIQPSLE DPFQPPSIPI TVYYAVLERA CRSVLLHAPS EAPQIVRGAS DEARKHTYNL  120
TIAWYRMGDN CAIPITVMEY TECPYNKSLG VCPIRTQPRW SYYDSFSAVS EDNLGFLMHA  180
PAFETAGTYL RLVKINDWTE ITQFILEHRA RASCKYALPL RIPPAACLTS KAYQQGVTVD  240
SIGMLPRFIP ENQRTVALYS LKIAGWHGPK PPYTSTLLPP ELSDTTNATQ PELVPEDPED  300
SALLEDPAGT VSSQIPPNWH IPSIQDVAPH HAPAAPSNPG LIIGALAGST LAVLVIGGIA  360
FWVRRRAQMA PKRLRLPHIR DDDAPPSHQP LFY                               393

SEQ ID NO: 7             moltype = RNA  length = 1779
FEATURE                  Location/Qualifiers
misc_feature             1..1779
                         note = All uridine residues are 1-methyl-pseudouridine -
                          encodes glycoprotein C from Herpes Simplex Virus-1
source                   1..1779
                         mol_type = other RNA
                         organism = synthetic construct
```

```
SEQUENCE: 7
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcatggccat ctccggcgtg cccgtgctgg gcttcttcat  180
catcgccgtg ctgatgtccg cccaggagtc ctgggccgag accgcctcca ccggccccac  240
catcaccgcc ggcgccgtga ccaacgcctc cgaggccccc acctccggct cccccggctc  300
cgccgcctcc cccgaggtga cccccacctc cacccccaac cccaacaacg tgacccagaa  360
caagaccacc cccaccgagc ccgcctcccc ccccaccacc cccaagccca cctccacccc  420
caagtccccc cccacctcca cccccgaccc caagcccaag aacaacacca cccccgccaa  480
gtccggccgc cccaccaagc cccccggccc cgtgtggtgc gaccgccgcg accccctggc  540
ccgctacggc tcccgcgtgc agatccgctg ccgcttccgc aactccaccc gcatggagtt  600
ccgcctgcag atctggcgct actccatggg cccctcccc  cccatcgccc ccgcccccga  660
cctggaggag gtgctgacca acatcaccgc ccccccggc  ggcctgctgg tgtacgactc  720
cgcccccaac ctgaccgacc cccacgtgct gtgggccgag ggcgccggcc ccggcgccga  780
cccccccctg tactccgtga ccggccccct gcccacccag cgcctgatca tcggcgaggt  840
gacccccgcc acccagggca tgtactacct ggcctggggc cgcatggact ccccccacga  900
gtacggcacc tgggtgcgcg tgcgcatgtt ccgccccccc tccctgaccc tgcagcccca  960
cgccgtgatg gagggccagc ccttcaaggc cacctgcacc gccgccgcct actacccccg  1020
caacccgtg  gagttcgact ggttcgagga cgaccgccag gtgttcaacc ccggccagat  1080
cgacacccag acccacgagc accccgacgg cttcaccacc gtgtccaccg tgacctccga  1140
ggccgtgggc ggccaggtgc ccccccgcac cttcacctgc cagatgacct ggcaccgcga  1200
ctccgtgacc ttctcccgcc gcaacgccac cggcctggcc ctggtgctgc cccgccccac  1260
catcaccatg gagttcggcg tgcgccacgt ggtgtgcacc gccggctgcg tgcccgaggg  1320
cgtgaccttc gcctggttcc tgggcgacga cccctcccc  gccgccaagt ccgccgtgac  1380
cgcccaggag tcctgcgacc accccggcct ggccaccgtg cgctccaccc tgcccatctc  1440
ctacgactac tccgagtaca tctgccgcct gaccggctac cccgccggca tccccgtgct  1500
ggagcaccac taactagtag tgactgacta ggatctggtt accactaaac cagcctcaag  1560
aacacccgaa tggagtctct aagctacata ataccaactt acacttacaa aatgttgtcc  1620
cccaaaatgt agccattcgt atctgctcct aataaaaaga aagtttcttc acattctaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaac                         1779

SEQ ID NO: 8           moltype = AA  length = 431
FEATURE                Location/Qualifiers
source                 1..431
                       mol_type = protein
                       organism = Human alphaherpesvirus 1
SEQUENCE: 8
ETASTGPTIT AGAVTNASEA PTSGSPGSAA SPEVTPTSTP NPNNVTQNKT TPTEPASPPT  60
TPKPTSTPKS PPTSTPDPKP KNNTTPAKSG RPTKPPGPVW CDRRDPLARY GSRVQIRCRF  120
RNSTRMEFRL QIWRYSMGPS PPIAPAPDLE EVLTNITAPP GGLLVYDSAP NLTDPHVLWA  180
EGAGPGADPP LYSVTGPLPT QRLIIGEVTP ATQGMYYLAW GRMDSPHEYG TWVRVRMFRP  240
PSLTLQPHAV MEGQPFKATC TAAAYYPRNP VEFDWFEDDR QVFNPGQIDT QTHEHPDGFT  300
TVSTVTSEAV GGQVPPRTFT CQMTWHRDSV TFSRRNATGL ALVLPRPTIT MEFGVRHVVC  360
TAGCVPEGVT FAWFLGDDPS PAAKSAVTAQ ESCDHPGLAT VRSTLPISYD YSEYICRLTG  420
YPAGIPVLEH H                                                        431

SEQ ID NO: 9           moltype = AA  length = 511
FEATURE                Location/Qualifiers
source                 1..511
                       mol_type = protein
                       organism = Human alphaherpesvirus 1
SEQUENCE: 9
MAPGRVGLAV VLWGLLWLGA GVAGGSETAS TGPTITAGAV TNASEAPTSG SPGSAASPEV  60
TPTSTPNPNN VTQNKTTPTE PASPPTTPKP TSTPKSPPTS TPDPKPKNNT TPAKSGRPTK  120
PPGPVWCDRR DPLARYGSRV QIRCRFRNST RMEFRLQIWR YSMGPSPPIA PAPDLEEVLT  180
NITAPPGGLL VYDSAPNLTD PHVLWAEGAG PGADPPLYSV TGPLPTQRLI IGEVTPATQG  240
MYYLAWGRMD SPHEYGTWVR VRMFRPPSLT LQPHAVMEGQ PFKATCTAAA YYPRNPVEFD  300
WFEDDRQVFN PGQIDTQTHE HPDGFTTVST VTSEAVGGQV PPRTFTCQMT WHRDSVTFSR  360
RNATGLALVL PRPTITMEFG VRHVVCTAGC VPEGVTFAWF LGDDPSPAAK SAVTAQESCD  420
HPGLATVRST LPISYDYSEY ICRLTGYPAG IPVLEHHGSH QPPPRDPTER QVIEAIEWVG  480
IGIGVLAAGV LVVTAIVYVV RTSQSRQRHR R                                 511

SEQ ID NO: 10          moltype = RNA  length = 1668
FEATURE                Location/Qualifiers
misc_feature           1..1668
                       note = All uridine residues are 1-methyl-pseudouridine -
                        encodes glycoprotein C from Herpes Simplex Virus-2
source                 1..1668
                       mol_type = other RNA
                       organism = synthetic construct
SEQUENCE: 10
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcatgcgcat gcagctgctg ctgctgatcg ccctgtccct  180
ggccctggtg accaactccg cctcccccgg ccgcaccatc accgtgggcc cccgcggcaa  240
cgcctccaac gccgccccct ccgcctcccc ccgcaacgcc tccgcccccc gcaccacccc  300
cacccccccc cagccccgca aggccaccaa gtccaaggcc tccaccgcca agcccgcccc  360
cccccccaag accggccccc ccaagacctc ctccgagccc gtgcgctgca accgccacga  420
```

```
cccccctggcc cgctacggct cccgcgtgca gatccgctgc cgcttcccca actccacccg  480
caccgagttc cgcctgcaga tctggcgcta cgccaccgcc accgacgccg agatcggcac  540
cgccccctcc ctggaggagg tgatggtgaa cgtgtccgcc ccccccggcg gccagctggt  600
gtacgactcc gcccccaacc gcaccgaccc ccacgtgatc tgggccgagg gcgccggccc  660
cggcgcctcc ccccgcctgt actccgtggt gggccccctg ggccgccagc gcctgatcat  720
cgaggagctg accctggaga cccagggcat gtactactgg gtgtggggcc gcaccgaccg  780
cccctccgcc tacggcacct gggtgcgcgt gcgcgtgttc cgccccccct ccctgaccat  840
ccacccccac gccgtgctgg agggccagcc cttcaaggcc acctgcaccg ccgccaccta  900
ctaccccggc aaccgcgccg agttcgtgtg gttcgaggac ggccgccgcg tgttcgaccc  960
cgcccagatc cacacccaga cccaggagaa ccccgacggc ttctccaccg tgtccaccgt  1020
gacctccgcc gccgtgggcg gccagggccc cccccgcacc ttcacctgcc agctgacctg  1080
gcaccgcgac tccgtgtcct tctcccgccg caacgcctcc ggcaccgcct ccgtgctgcc  1140
ccgccccacc atcaccatgg agttcaccgg cgaccacgcc gtgtgcaccg ccggctgcgt  1200
gcccgagggc gtgaccttcg cctggttcct gggcgacgac tcctcccccg ccgagaaggt  1260
ggccgtggcc tcccagacct cctgcggccg ccccggcacc gccaccatcc gctccaccct  1320
gcccgtgtcc tacgagcaga ccgagtacat ctgccgcctg gccggctacc ccgacggcat  1380
ccccgtgctg gagcaccact aactagtagt gactgactag gatctggtta ccactaaacc  1440
agcctcaaga acacccgaat ggagtctcta agctacataa taccaactta cacttacaaa  1500
atgttgtccc ccaaaatgta gccattcgta tctgctccta ataaaaagaa agtttcttca  1560
cattctaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaac              1668

SEQ ID NO: 11          moltype = AA  length = 400
FEATURE                Location/Qualifiers
source                 1..400
                       mol_type = protein
                       organism = Human alphaherpesvirus 2
SEQUENCE: 11
ASPGRTITVG PRGNASNAAP SASPRNASAP RTTPTPPQPR KATKSKASTA KPAPPPKTGP  60
PKTSSEPVRC NRHDPLARYG SRVQIRCRFP NSTRTESRLQ IWRYATATDA EIGTAPSLEE  120
VMVNVSAPPG GQLVYDSAPN RTDPHVIWAE GAGPGASPRL YSVVGPLGRQ RLIIEELTLE  180
TQGMYYWVWG RTDRPSAYGT WVRVRVFRPP SLTIHPHAVL EGQPFKATCT AATYYPGNRA  240
EFVWFEDGRR VFDPAQIHTQ TQENPDGFST VSTVTSAAVG GQGPPRTFTC QLTWHRDSVS  300
FSRRNASGTA SVLPRPTITM EFTGDHAVCT AGCVPEGVTF AWFLGDDSSP AEKVAVASQT  360
SCGRPGTATI RSTLPVSYEQ TEYICRLAGY PDGIPVLEHH                        400

SEQ ID NO: 12          moltype = AA  length = 480
FEATURE                Location/Qualifiers
source                 1..480
                       mol_type = protein
                       organism = Human alphaherpesvirus 2
SEQUENCE: 12
MALGRVGLAV GLWGLLWVGV VVVLANASPG RTITVGPRGN ASNAAPSASP RNASAPRTTP  60
TPPQPRKATK SKASTAKPAP PPKTGPPKTS SEPVRCNRHD PLARYGSRVQ IRCRFPNSTR  120
TEFRLQIWRY ATATDAEIGT APSLEEVMVN VSAPPGGQLV YDSAPNRTDP HVIWAEGAGP  180
GASPRLYSVV GPLGRQRLII EELTLETQGM YYWVWGRTDR PSAYGTWVRV RVFRPPSLTI  240
HPHAVLEGQP FKATCTAATY YPGNRAEFVW FEDGRRVFDP AQIHTQTQEN PDGFSTVSTV  300
TSAAVGGQGP PRTFTCQLTW HRDSVSFSRR NASGTASVLP RPTITMEFTG DHAVCTAGCV  360
PEGVTFAWFL GDDSSPAEKV AVASQTSCGR PGTATIRSTL PVSYEQTEYI CRLAGYPDGI  420
PVLEHHGSHQ PPPRDPTERQ VIRAVEGAGI GVAVLVAVVL AGTAVVYLTH ASSVRYRRLR  480

SEQ ID NO: 13          moltype = RNA  length = 1626
FEATURE                Location/Qualifiers
misc_feature           1..1626
                       note = All uridine residues are 1-methyl-pseudouridine -
                        encodes glycoprotein E from Herpes Simplex Virus-1
source                 1..1626
                       mol_type = other RNA
                       organism = synthetic construct
SEQUENCE: 13
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcatgcgcat gcagctgctg ctgctgatcg ccctgtccct  180
ggccctggtg accaactcca agacctcctg gcgccgcgtg tccgtgggcg aggacgtgtc  240
cctgctgccc gcccccggcc ccaccggccg cggccccacc cagaagctgc tgtgggccgt  300
ggagcccctg gacggctgcg gcccctgca cccctcctgg gtgtccctga tgcccccaa  360
gcaggtgccc gagaccgtgg tggacgccgc ctgcatgcgc gcccccgtgc ccctggccat  420
ggcctacgcc ccccccgccc cctccgccac cggcggcctg cgcaccgact tcgtgtggca  480
ggagcgcgcc gccgtggtga accgctccct ggtgatctac ggcgtgcgcg agaccgactc  540
cggcctgtac accctgtccg tgggcgacat caaggacccc gcccgccagg tggcctccgt  600
ggtgctggtg gtgcagcccg cccccgtgcc caccccccc cccacccccg ccgactacga  660
cgaggacgac aacgacgagg gcgagggcga ggacgagtcc ctggccggca cccccgcctc  720
cggcaccccc cgcctgcccc cctcccccgc cccccccgc tcctggccct ccgcccccga  780
ggtgtcccac gtgcgcggcg tgaccgtgcg catggagacc cccgaggcca tcctgttctc  840
ccccggcgag gccttctcca ccaacgtgtc catccacgcc atcgcccacg acgaccagac  900
ctacaccatg gacgtggtgt ggctgcgctt cgacgtgccc acctcctgcg ccgagatgcg  960
catctacgag tcctgcctgt accaccccca gctgcccgag tgcctgtccc ccgccgacgc  1020
cccctgcgcc gcctccacct ggacctcccg cctggccgtg cgctcctacg ccggctgctc  1080
ccgcaccaac cccccccccc gctgctccgc cgaggcccac atggagccct tccccggcct  1140
```

-continued

```
ggcctggcag gccgcctccg tgaacctgga gttccgcgac gcctcccccc agcactccgg  1200
cctgtacctg tgcgtggtgt acgtgaacga ccacatccac gcctggggcc acatcaccat  1260
caacaccgcc gcccagtacc gcaacgccgt ggtggagcag cccctgcccc agcgcggcgc  1320
cgacctggcc gagcccaccc acccccacgt gggcgcctaa ctagtagtga ctgactagga  1380
tctggttacc actaaaccag cctcaagaac acccgaatgg agtctctaag ctacataata  1440
ccaacttaca cttacaaaat gttgtccccc aaaatgtagc cattcgtatc tgctcctaat  1500
aaaaagaaag tttcttcaca ttctaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaac                                                              1626

SEQ ID NO: 14          moltype = AA  length = 386
FEATURE                Location/Qualifiers
source                 1..386
                       mol_type = protein
                       organism = Human alphaherpesvirus 1
SEQUENCE: 14
KTSWRRVSVG EDVSLLPAPG PTGRGPTQKL LWAVEPLDGC GPLHPSWVSL MPPKQVPETV  60
VDAACMRAPV PLAMAYAPPA PSATGGLRTD FVWQERAAVV NRSLVIYGVR ETDSGLYTLS  120
VGDIKDPARQ VASVVLVVQP APVPTPPPTP ADYDEDDNDE GEGEDESLAG TPASGTPRLP  180
PSPAPPRSWP SAPEVSHVRG VTVRMETPEA ILFSPGEAFS TNVSIHAIAH DDQTYTMDVV  240
WLRFDVPTSC AEMRIYESCL YHPQLPECLS PADAPCAAST WTSRLAVRSY AGCSRTNPPP  300
RCSAEAHMEP FPGLAWQAAS VNLEFRDASP QHSGLYLCVV YVNDHIHAWG HITINTAAQY  360
RNAVVEQPLP QRGADLAEPT HPHVGA                                        386

SEQ ID NO: 15          moltype = AA  length = 552
FEATURE                Location/Qualifiers
source                 1..552
                       mol_type = protein
                       organism = Human alphaherpesvirus 1
SEQUENCE: 15
MDRGAVVGFL LGVCVVSCLA GTPKTSWRRV SVGEDVSLLP APGPTGRGPT QKLLWAVEPL  60
DGCGPLHPSW VSLMPPKQVP ETVVDAACMR APVPLAMAYA PPAPSATGGL RTDFVWQERA  120
AVVNRSLVIY GVRETDSGLY TLSVGDIKDP ARQVASVVLV VQPAPVPTPP PTPADYDEDD  180
NDEGEGEDES LAGTPASGTP RLPPSPAPPR SWPSAPEVSH VRGVTVRMET PEAILFSPGE  240
AFSTNVSIHA IAHDDQTYTM DVVWLRFDVP TSCAEMRIYE SCLYHPQLPE CLSPADAPCA  300
ASTWTSRLAV RSYAGCSRTN PPPRCSAEAH MEPFPGLAWQ AASVNLEFRD ASPQHSGLYL  360
CVVYVNDHIH AWGHITINTA AQYRNAVVEQ PLPQRGADLA EPTHPHVGAP PHAPPTHGAL  420
RLGAVMGAAL LLSALGLSVW ACMTCWRRRA WRAVKSRASG KGPTYIRVAD SELYADWSSD  480
SEGERDQVPW LAPPERPDSP STNGSGFEIL SPTAPSVYPR SDGHQSRRQL TTFGSGRPDR  540
RYSQASDSSV FW                                                       552

SEQ ID NO: 16          moltype = RNA  length = 1614
FEATURE                Location/Qualifiers
misc_feature           1..1614
                       note = All uridine residues are 1-methyl-pseudouridine -
                        encodes glycoprotein E from Herpes Simplex Virus-2
source                 1..1614
                       mol_type = other RNA
                       organism = synthetic construct
SEQUENCE: 16
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcatgcgcat gcagctgctg ctgctgatcg ccctgtccct  180
ggccctggtg accaactccc gcacctcctg gaagcgcgtg acctccggcg aggacgtggt  240
gctgctgccc gcccccgccg gccccgagga gcgcacccgc gcccacaagc tgctgtgggc  300
cgccgagccc ctggacgcct gcggccccct gcgcccctcc tgggtggccc tgtggccccc  360
ccgccgcgtg ctggagaccg tggtggacgc cgcctgcatg cgcgccccgg agcccctggc  420
catcgcctac tcccccccct tccccgccgg cgacgagggc ctgtactccg agctggcctg  480
gcgcgaccgc gtggccgtgg tgaacgagtc cctggtgatc tacggcgccc tggagaccga  540
ctccggcctg tacaccctgt ccgtggtggg cctgtccgac gaggcccgcc aggtggcctc  600
cgtggtgctg gtggtggagc ccgcccccgt gcccaccccc acccccgacg actacgacga  660
ggaggacgac gccggcgtgt ccgagcgcac ccccgtgtcc gtgccccccc ccaccccccc  720
ccgccgcccc cccgtggccc cccccaccca cccccgcgtg atccccgagg tgtcccacgt  780
gcgcggcgtg accgtgcaca tggagacccc cgaggccatc ctgttcgccc ccggcgagac  840
cttcggcacc aacgtgtcca tccacgccat cgcccacgac gacggcccct acgccatgga  900
cgtggtgtgg atgcgcttcg acgtgccctc ctcctgcgcc gagatgcgca tctacgaggc  960
ctgcctgtac cacccccagc tgcccgagtg cctgtccccc gccgacgccc cctgcgccgt  1020
gtcctcctgg gcctaccgcc tggccgtgcg ctcctacgcc ggctgctccc gcaccacccc  1080
cccccccgc tgcttcgccg aggccgcat ggagcccgtg cccggcctgg cctggctggc  1140
ctccaccgtg aacctggagt tccagcacgc ctccccccag cacgccggcc tgtacctgtg  1200
cgtggtgtac gtggacgacc acatccacgc ctggggccac atgaccatct ccaccgccgc  1260
ccagtaccgc aacgccgtgg tggagcagca cctgccccag cgccagcccg agcccgtgga  1320
gcccacccgc ccccacgtgc gcgcctaact agtagtgact gactaggatc tggttaccac  1380
taaaccagcc tcaagaacac ccgaatggag tctctaagct acataatacc aacttacact  1440
tacaaaatgt tgtcccccaa aatgtagcca ttcgtatctg ctcctaataa aaagaaagtt  1500
tcttcacatt ctaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaac        1614

SEQ ID NO: 17          moltype = AA  length = 382
```

```
FEATURE               Location/Qualifiers
source                1..382
                      mol_type = protein
                      organism = Human alphaherpesvirus 2
SEQUENCE: 17
RTSWKRVTSG EDVVLLPAPA GPEERTRAHK LLWAAEPLDA CGPLRPSWVA LWPPRRVLET  60
VVDAACMRAP EPLAIAYSPP FPAGDEGLYS ELAWRDRVAV VNESLVIYGA LETDSGLYTL  120
SVVGLSDEAR QVASVVLVVE PAPVPTPTPD DYDEEDDAGV SERTPVSVPP PTPPRRPPVA  180
PPTHPRVIPE VSHVRGVTVH METPEAILFA PGETFGTNVS IHAIAHDDGP YAMDVVWMRF  240
DVPSSCAEMR IYEACLYHPQ LPECLSPADA PCAVSSWAYR LAVRSYAGCS RTTPPPRCFA  300
EARMEPVPGL AWLASTVNLE FQHASPQHAG LYLCVVYVDD HIHAWGHMTI STAAQYRNAV  360
VEQHLPQRQP EPVEPTRPHV RA                                         382

SEQ ID NO: 18         moltype = AA  length = 545
FEATURE               Location/Qualifiers
source                1..545
                      mol_type = protein
                      organism = Human alphaherpesvirus 2
SEQUENCE: 18
MARGAGLVFF VGVWVVSCLA AAPRTSWKRV TSGEDVVLLP APAERTRAHK LLWAAEPLDA  60
CGPLRPSWVA LWPPRRVLET VVDAACMRAP EPLAIAYSPP FPAGDEGLYS ELAWRDRVAV  120
VNESLVIYGA LETDSGLYTL SVVGLSDEAR QVASVVLVVE PAPVPTPTPD DYDEEDDAGV  180
TNARRSAFPP QPPPRRPPVA PPTHPRVIPE VSHVRGVTVH METLEAILFA PGETFGTNVS  240
IHAIAHDDGP YAMDVVWMRF DVPSSCADMR IYEACLYHPQ LPECLSPADA PCAVSSWAYR  300
LAVRSYAGCS RTTPPPRCFA EARMEPVPGL AWLASTVNLE FQHASPQHAG LYLCVVYVDD  360
HIHAWGHMTI STAAQYRNAV VEQHLPQRQP EPVEPTRPHV RAPHPAPSAR GPLRLGAVLG  420
AALLLAALGL SAWACMTCWR RRSWRAVKSR ASATGPTYIR VADSELYADW SSDSEGERDG  480
SLWQDPPERP DSPSTNGSGF EILSPTAPSV YPHSEGRKSR RPLTTFGSGS PGRRHSQASY  540
PSVLW                                                            545

SEQ ID NO: 19         moltype = RNA  length = 57
FEATURE               Location/Qualifiers
source                1..57
                      mol_type = mRNA
                      organism = Human alphaherpesvirus 2
SEQUENCE: 19
atgacccgcc tgaccgtgct ggccctgctg gccggcctgc tggcctcctc ccgcgcc    57

SEQ ID NO: 20         moltype = RNA  length = 57
FEATURE               Location/Qualifiers
misc_feature          1..57
                      note = codon-optimized form of human IL-2
source                1..57
                      mol_type = mRNA
                      organism = Homo sapiens
SEQUENCE: 20
atgcgcatgc agctgctgct gctgatcgcc ctgtccctgg ccctggtgac caactcc    57

SEQ ID NO: 21         moltype = RNA  length = 75
FEATURE               Location/Qualifiers
source                1..75
                      mol_type = mRNA
                      organism = Homo sapiens
SEQUENCE: 21
atggccatct ccggcgtgcc cgtgctgggc ttcttcatca tcgccgtgct gatgtccgcc  60
caggagtcct gggcc                                                  75

SEQ ID NO: 22         moltype = RNA  length = 921
FEATURE               Location/Qualifiers
source                1..921
                      mol_type = mRNA
                      organism = Human alphaherpesvirus 2
SEQUENCE: 22
aagtacgccc tggccgaccc ctccctgaag atggccgacc ccaaccgctt ccgcggcaag  60
aacctgcccg tgctggacca gctgaccgac cccccccggcg tgaagcgcgt gtaccacatc  120
cagccctccc tggaggaccc cttccagccc ccctccatcc ccatcaccgt gtactacgcc  180
gtgctggagc gcgcctgccg ctccgtgctg ctgcacgccc cctccgaggc cccccagatc  240
gtgcgcggcg cctccgacga ggcccgcaag cacacctaca acctgaccat cgcctggtac  300
cgcatgggcg acaactgcgc catccccatc accgtgatgg agtacaccga gtgcccctac  360
aacaagtccc tgggcgtgtg ccccatccgc acccagcccc gctggtccta ctacgactcc  420
ttctccgccg tgtccgagga caacctgggc ttcctgatgc acgcccccgc cttcgagacc  480
gccggcacct acctgcgcct ggtgaagatc aacgactgga ccgagatcac ccagttcatc  540
ctggagcacc gcgcccgcgc ctcctgcaag tacgccctgc ccctgcgcat ccccccccgcc  600
gcctgcctga cctccaaggc ctaccagcag ggcgtgaccg tggactccat cggcatgctg  660
ccccgcttca tccccgagaa ccagcgcacc gtggccctgt actccctgaa gatcgccggc  720
tggcacggcc ccaagcccc ctacacctcc accctgctgc cccccgagct gtccgacacc  780
accaacgcca cccagcccga gctggtgccc gaggaccccg aggactccgc cctgctggag  840
gaccccgccg gcaccgtgtc ctcccagatc ccccccaact ggcacatccc ctccatccag  900
gacgtggccc cccaccacta a                                           921
```

```
SEQ ID NO: 23            moltype = RNA  length = 1203
FEATURE                  Location/Qualifiers
source                   1..1203
                         mol_type = mRNA
                         organism = Human alphaherpesvirus 2
SEQUENCE: 23
gcctccccg gccgcaccat caccgtgggc ccccgcggca acgcctccaa cgccgccccc  60
tccgcctccc cccgcaacgc ctccgccccc cgcaccaccc ccacccccc ccagccccgc  120
aaggccacca agtccaaggc ctccaccgcc aagcccgccc cccccccaa gaccggcccc  180
cccaagacct cctccgagcc cgtgcgctgc aaccgccacg acccccctggc ccgctacggc  240
tcccgcgtgc agatccgctg ccgcttcccc aactccaccc gcaccgagtt ccgcctgcag  300
atctggcgct acgccaccgc caccgacgcc gagatcggca ccgccccctc cctggaggag  360
gtgatggtga acgtgtccgc cccccccggc ggccagctgg tgtacgactc cgcccccaac  420
cgcaccgacc cccacgtgat ctgggccgag ggcgccggcc ccggcgcctc cccccgcctg  480
tactccgtgg tgggcccccct gggccgccag cgcctgatca tcgaggagct gaccctggag  540
acccagggca tgtactactg ggtgtggggc cgcaccgacc gcccctccgc ctacggcacc  600
tgggtgcgcg tgcgcgtgtt ccgccccccc tccctgacca tccaccccca cgccgtgctg  660
gagggccagc ccttcaaggc cacctgcacc gccgccacct actaccccgg caaccgcgcc  720
gagttcgtgt ggttcgagga cggccgccgc gtgttcgacc ccgcccagat ccacacccag  780
acccaggaga accccgacgg cttctccacc gtgtccaccg tgacctccgc cgccgtgggc  840
ggccagggcc ccccccgcac cttcacctgc cagctgacct ggcaccgcga ctccgtgtcc  900
ttctcccgcc gcaacgcctc cggcaccgcc tccgtgctgc cccgccccac catcaccatg  960
gagttcaccg gcgaccacgc cgtgtgcacc gccggctgcg tgcccgaggg cgtgaccttc  1020
gcctggttcc tgggcgacga ctcctccccc gccgagaagg tggccgtggc ctcccagacc  1080
tcctgcggcc gccccggcac cgccaccatc cgctccaccc tgcccgtgtc ctacgagcag  1140
accgagtaca tctgccgcct ggccggctac cccgacggca tccccgtgct ggagcaccac  1200
taa                                                               1203

SEQ ID NO: 24            moltype = RNA  length = 1149
FEATURE                  Location/Qualifiers
source                   1..1149
                         mol_type = mRNA
                         organism = Human alphaherpesvirus 2
SEQUENCE: 24
cgcacctcct ggaagcgcgt gacctccggc gaggacgtgg tgctgctgcc cgcccccgcc  60
ggccccgagg agcgcacccg cgcccacaag ctgctgtggg ccgccgagcc cctggacgcc  120
tgcggccccc tgcgcccctc ctgggtggcc ctgtggcccc cccgccgcgt gctggagacc  180
gtggtggacg ccgcctgcat gcgcgccccc gagcccctgg ccatcgccta ctcccccccc  240
ttccccgccg gcgacgaggg cctgtactcc gagctggcct ggcgcgaccg cgtggccgtg  300
gtgaacgagt ccctggtgat ctacggcgcc ctggagaccg actccggcct gtacaccctg  360
tccgtggtgg gcctgtccga cgaggcccgc caggtggcct ccgtggtgct ggtggtggag  420
cccgcccccg tgcccacccc cacccccgac gactacgacg aggaggacga cgccggcgtg  480
tccgagcgca cccccgtgtc cgtgcccccc cccacccccc cccgccgccc ccccgtggcc  540
cccccccaccc acccccgcgt gatccccgag gtgtcccacg tgcgcggcgt gaccgtgcac  600
atggagaccc ccgaggccat cctgttcgcc cccggcgaga ccttcggcac caacgtgtcc  660
atccacgcca tcgcccacga cgacggcccc tacgccatgg acgtggtgtg gatgcgcttc  720
gacgtgccct cctcctgcgc cgagatgcgc atctacgagg cctgcctgta ccacccccag  780
ctgcccgagt gcctgtcccc cgccgacgcc ccctgcgccg tgtcctcctg ggcctaccgc  840
ctggccgtgc gctcctacgc cggctgctcc cgcaccaccc cccccccccg ctgcttcgcc  900
gaggcccgca tggagcccgt gcccggcctg gcctggctgg cctccaccgt gaacctggag  960
ttccagcacg cctcccccca gcacgccggc ctgtacctgt gcgtggtgta cgtggacgac  1020
cacatccacg cctggggcca catgaccatc tccaccgccg cccagtaccg caacgccgtg  1080
gtggagcagc acctgcccca gcgccagccc gagcccgtgg agcccacccg cccccacgtg  1140
cgcgcctaa                                                         1149
```

MODIFIED mRNA VACCINES ENCODING HERPES SIMPLEX VIRUS GLYCOPROTEINS AND USES THEREOF

CROSS-REFERENCE TO RELATED APPLICATIONS

This application is a Continuation of U.S. patent application Ser. No. 17/349,929 filed Jun. 17, 2021, which is a Continuation of U.S. patent application Ser. No. 16/640,008, filed Feb. 18, 2020, which is a National Phase of PCT International Application No. PCT/IB2018/056210 filed Aug. 17, 2018, claiming the benefit of U.S. Patent Application No. 62/546,648, filed Aug. 17, 2017 and U.S. Patent Application No. 62/701,019, filed Jul. 20, 2018 which are hereby incorporated by reference.

STATEMENT REGARDING FEDERALLY SPONSORED RESEARCH OR DEVELOPMENT

This invention was made with government support under AI104854 awarded by the National Institutes of Health. The government has certain rights in the invention.

INCORPORATION OF SEQUENCE LISTING

The instant application contains a Sequence Listing that has been submitted electronically in XML format and is hereby incorporated by reference in its entirety. The XML copy, created on Sep. 18, 2023, is named P-572137-US3-SEQLIST.xml and is 42 kilobytes in size.

FIELD OF INVENTION

The present invention provides compositions for the prevention and treatment of genital herpes, comprising nucleoside modified mRNAs that encode herpes simplex virus (HSV) glycoproteins, including those involved in virus entry and immune evasion, and methods of use thereof.

BACKGROUND OF THE INVENTION

A genital herpes vaccine is urgently needed to prevent pain and suffering, reduce the incidence of neonatal herpes, and decrease the risk of HIV acquisition and transmission that accompanies genital infection. Approximately a half-billion people worldwide are infected with herpes simplex virus type 2 (HSV-2), the virus that causes genital herpes. In some individuals, infection results in painful, recurrent genital ulcers, while in others, the infection remains quiescent. In both settings, infected individuals may transmit virus to their intimate partners. Genital herpes increases the risk that an infected person will acquire HIV if exposed during sexual intercourse. A vaccine for genital herpes is urgently needed, yet none is available.

Chiron Corp. evaluated a prophylactic vaccine containing two HSV-2 glycoproteins involved in virus entry, glycoproteins B (gB2) and D (gD2) given with MF59 as adjuvant. The vaccine did not protect seronegative partners from HSV-2 infection, although it delayed onset of infection over the first 5 months after immunization. GlaxoSmithKline (GSK) assessed a prophylactic vaccine using gD2 antigen with monophosphoryl lipid A (MPL) and alum as adjuvants. Overall, no protection against genital lesions was detected, although significant protection was noted in a subgroup of HSV-1 and HSV-2 doubly seronegative women. A follow-up trial was performed in doubly seronegative women that showed no overall protection against genital herpes; however, the vaccine was efficacious against HSV-1. This result was noteworthy because HSV-1 accounted for 60% of genital herpes infections in the control group. These studies indicate that targeting a vaccine to block HSV-2 entry is not sufficient.

HSV-1 and HSV-2 gC are immune evasion molecules that function as regulators of the complement cascade. During complement activation, C3, the most abundant complement protein, is cleaved to C3b, which activates the membrane attack complex leading to virus neutralization and lysis of infected cells. C3b stimulates B- and T-cell responses and serves as a link between innate and acquired immunity. HSV-1 and HSV-2 gC bind C3b to inhibit activities mediated by C3b. Immunization with gC1 and gC2 produces antibodies that bind to the glycoprotein and block its immune evasion functions.

HSV-1 and HSV-2 glycoprotein E (gE) function as immune evasion molecules by binding the Fc domain of an IgG molecule that is bound by its F(ab')2 domain to its target. A vaccine containing gE2 subunit antigen produces antibodies that bind to gE2 and block its immune evasion functions. HSV-2 gC2 and gE2 perform activities similar to mammalian complement and IgG Fc regulatory proteins, yet share no sequence homology with mammalian receptors, which suggests virtually no risk that immunization will induce autoimmunity.

Previous work from our lab examined vaccines containing gC, gD and gE and found that such vaccines provide protection against HSV infection. However, it is not known if mRNA vaccines encoding HSV gC, gD and gE would be effective in protecting against HSV infection.

Using nucleic acids as vaccines has multiple advantages. Nucleic acid vaccines can induce both humoral and cellular immune responses; have low effective dosages; are simple to manipulate; avail rapid testing; are cost-effective and reproducible in large scale production and isolation; can be produced at high frequency and are easily isolated; are more temperature-stable than conventional vaccines; have a long shelf-life; are easy to store and transport; and are unlikely to require a cold chain (Shedlock & Weiner, *J Leukocyte Biol.* Vol 68, 2000).

In principle, either exogenous DNA or RNA can express proteins in the mammalian body. Whether or not similar immune activity can be produced with both DNA and mRNA expressed proteins is uncertain. Conventional wisdom is that DNA is superior for the creation of vaccines and gene therapy due to its stability and ease of use.

DNA has been used in vaccines with success. DNA is fairly stable and unreactive and can be stored long term. However, DNA is self-replicating and can be easily damaged by ultra-violet radiation. DNA based vaccines may also raise safety concerns due to possible insertion of DNA into the genome, possible interruption of genes and formation of anti-DNA antibodies.

RNA vaccines exhibit important safety features. RNA is more reactive than DNA and less stable but is resistant to ultra-violet radiation. mRNA does not integrate into the host chromosomes. The delivery of mRNA results in faster expression of the antigen of interest and requires fewer copies for expression. mRNA expression is transient, which adds to its safety. mRNA is more effective than DNA for protein production in post mitotic and non-dividing cells because DNA requires translocation through the nuclear member and plasma membrane, while mRNA requires translocation only through the plasma membrane. mRNA is not only a template for translation, but also acts as a ligand for toll-like receptors and is nuclease sensitive; therefore it presents less concern for horizontal transmission.

In addition, RNA vaccines elegantly integrate adjuvanticity and antigen expression, thereby mimicking relevant aspects of viral infections. This increases their efficacy compared to inactivated vaccines that require the use of adjuvants, simplifying handling and production. RNA can address a range of dedicated immunologic pattern recognition receptors, including toll-like receptors 3, 7, and 8, RIG-I, MDA5, PKR, and others that may act synergistically and serve to enhance the induction of antigen-specific adaptive B and T cell responses. Importantly, by antigen synthesis in transfected host cells, mRNA vaccines directly introduce antigen into cellular antigen processing and presentation pathways, granting access to MHC molecules and triggering T cell responses, irrespective of the hosts MHC haplotype. This enables the induction of polyclonal T cell responses that may act synergistically with other immune responses, including B cells. Also, endogenous production of antigen ensures faithful posttranslational modification (e.g. proteolytic processing, glycosylation, etc.) that may positively impact immunogenicity.

SUMMARY OF THE INVENTION

In one embodiment, the present invention provides compositions comprising one or more nucleoside modified mRNAs, wherein each of said nucleoside modified mRNAs encodes a Herpes Simplex Virus (HSV) glycoprotein or immunogenic fragment thereof, and wherein said nucleoside modified mRNA comprises one or more pseudouridine residues.

In another embodiment, the present invention provides compositions comprising one or more nucleoside modified mRNAs, wherein each of said modified mRNAs encodes a Herpes Simplex Virus (HSV) glycoprotein or immunogenic fragment thereof, and wherein said nucleoside modified mRNA comprises 1-methylpseudouridine, wherein said pseudouridine residues comprise $m^1acp^3\Psi$ (1-methyl-3-(3-amino-5-carboxypropyl)pseudouridine, $m^1\Psi$ (1-methylpseudouridine), $\Psi m$ (2'-O-methylpseudouridine, $m^5D$ (5-methyldihydrouridine), $m^3\Psi$ (3-methylpseudouridine), or any combination thereof.

In another embodiment, the present invention provides compositions comprising modified mRNAs comprising one or more pseudouridine residues, wherein each of said modified mRNAs encode an a) HSV glycoprotein D (gD) or an immunogenic fragment thereof, b) HSV glycoprotein C (gC) or an immunogenic fragment thereof, c) HSV glycoprotein E (gE) or an immunogenic fragment thereof, or any combination thereof.

In another embodiment, the present invention provides a method of treating a Herpes Simplex Virus (HSV) infection in a subject, the method comprising the step of administering to said subject a composition comprising one or more modified mRNAs, wherein each of said modified mRNAs encodes an HSV glycoprotein or immunogenic fragment thereof, and wherein said modified mRNA comprises pseudouridine residues.

In another embodiment, the present invention provides a method of inducing an immune response in a subject, comprising the step of administering to said subject a composition comprising one or more modified mRNAs, wherein each of said modified mRNAs encodes an HSV glycoprotein or immunogenic fragment thereof, and wherein said modified mRNA comprises pseudouridine residues.

In a further embodiment, the present invention provides a method of suppressing, inhibiting, or reducing the incidence of a Herpes Simplex Virus (HSV) infection in a subject, the method comprising the step of administering to said subject a composition comprising one or more modified mRNAs, wherein each of said modified mRNAs encodes an HSV glycoprotein or immunogenic fragment thereof, and wherein said modified mRNA comprises pseudouridine residues.

In yet another embodiment, the present invention provides a method of treating a Herpes Simplex Virus (HSV) infection in a subject, the method comprising the step of administering to said subject a composition comprising one or more modified mRNAs encoding a) an HSV glycoprotein D (gD) or an immunogenic fragment thereof, b) an HSV glycoprotein C (gC) or an immunogenic fragment thereof, c) an HSV glycoprotein E (gE) or an immunogenic fragment thereof, or any combination thereof.

In a yet a further embodiment, the present invention provides a method of suppressing, inhibiting, or reducing the incidence of a Herpes Simplex Virus (HSV) infection in a subject, the method comprising the step of administering to said subject a composition comprising one to three modified mRNAs, wherein each of said modified mRNAs encodes a) HSV glycoprotein D (gD) or an immunogenic fragment thereof, b) HSV glycoprotein C (gC) or an immunogenic fragment thereof, and c) HSV glycoprotein E (gE) or an immunogenic fragment thereof, or any combination thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 1A. Western blot showing expression of gC2 by modified mRNA.

FIG. 1B. Western blot showing expression of gD2 by modified mRNA.

FIG. 1C. Western blot showing expression of gE2 by modified mRNA.

Figures 3A, 3B:
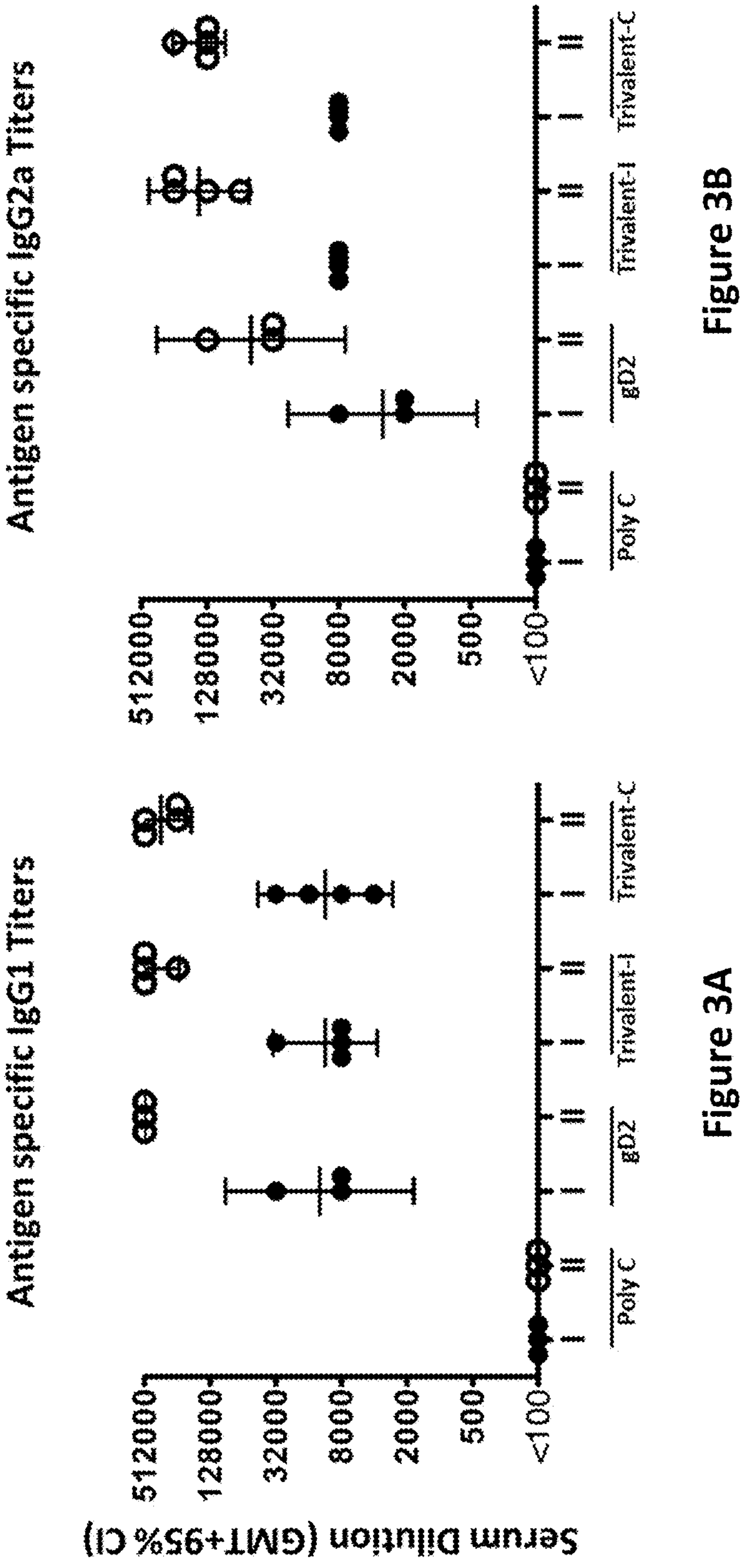

FIG. 3A. Antigen-specific IgG1 responses in mRNA vaccinated mice. Antibodies were evaluated after the first and second immunization for IgG1 responses. I indicates first immunization; II indicates second immunization.

FIG. 3B. Antigen-specific IgG2a responses in mRNA vaccinated mice. Antibodies were evaluated after the first and second immunization for IgG2a responses. I indicates first immunization; II indicates second immunization.

Figure 4:
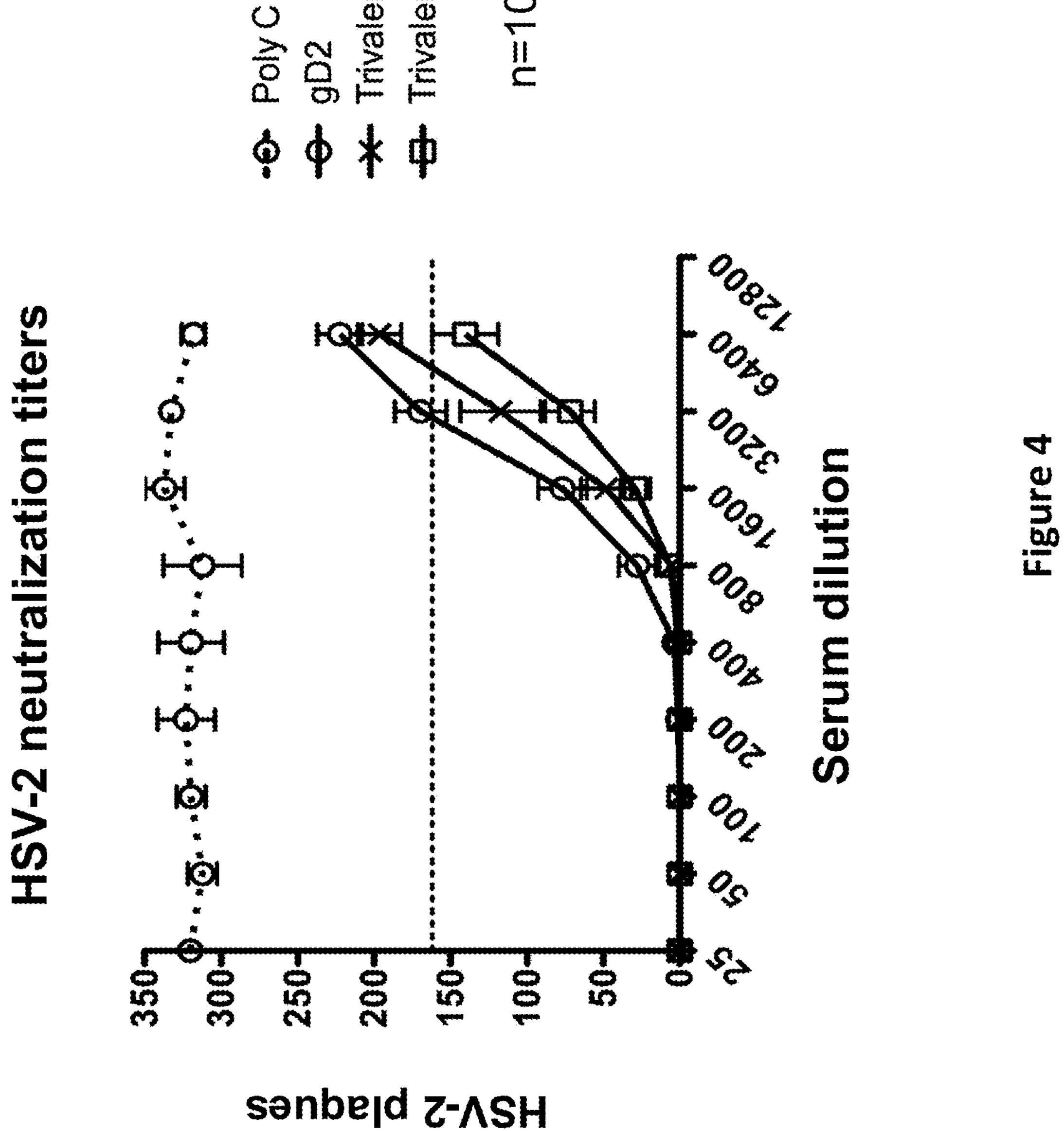

FIG. 4. Neutralizing antibody titers in mRNA vaccinated mice. 50% endpoint neutralization titers of serum were obtained after the second immunization. Titers were performed using 10% human complement. Trivalent-I animals were immunized with gC2/liposomal nanoparticle (LNP), gD2/LNP, and gE2/LNP, each given at a different site. Trivalent-C animals were immunized with gC2, gD2 and gE2 combined into a single LNP. P values comparing 50% endpoint neutralizing titers: Trivalent-I versus gD2, p=0.04; Trivalent-C versus gD2, p=0.002; Trivalent-I versus Trivalent-C, p-0.026.

Figures 5A, 5B:
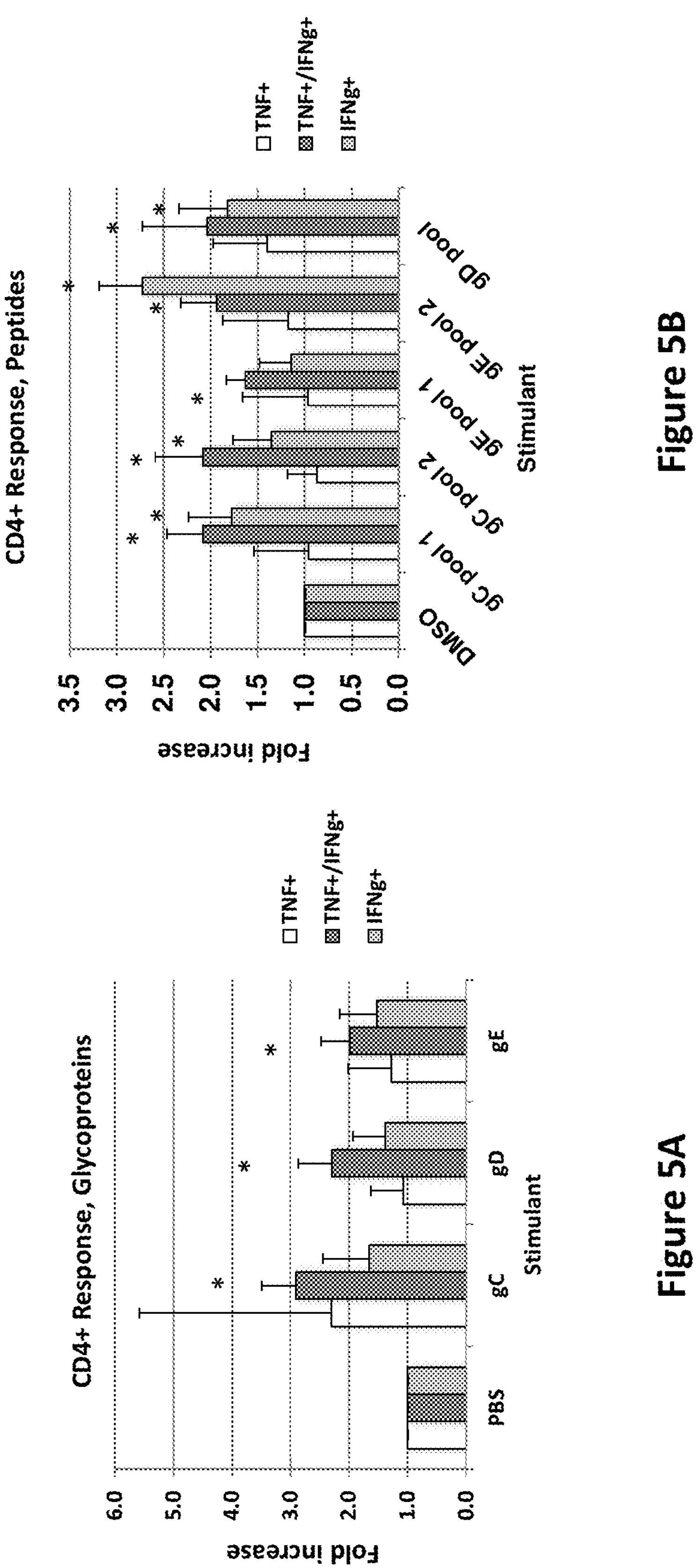

FIGS. 5A-5B. $CD4^+$ T cell responses to gC2, gD2 and gE2 mRNA each administered at a different intradermal site. Splenocytes were stimulated with subunit antigen glycoproteins (FIG. 5A) or 15 amino acid peptides with 11 overlapping amino acids to stimulate HSV-2 specific T cell responses (FIG. 5B). * indicates p<0.05 (t test) comparing gC, gD or gE with PBS stimulated $CD4^+$ T cells or DMSO stimulated $CD4^+$ T cells. Error bars represent SD.

Figure 6B:
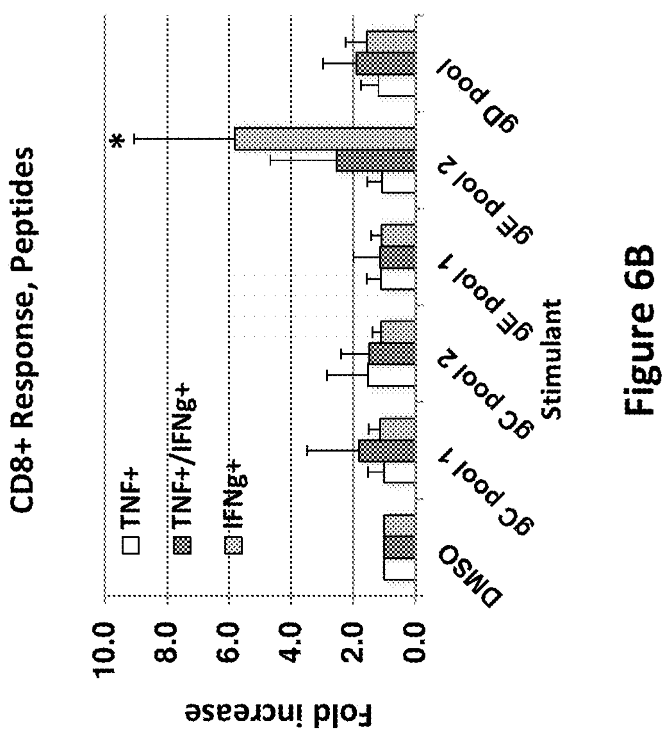
Figure 6A:
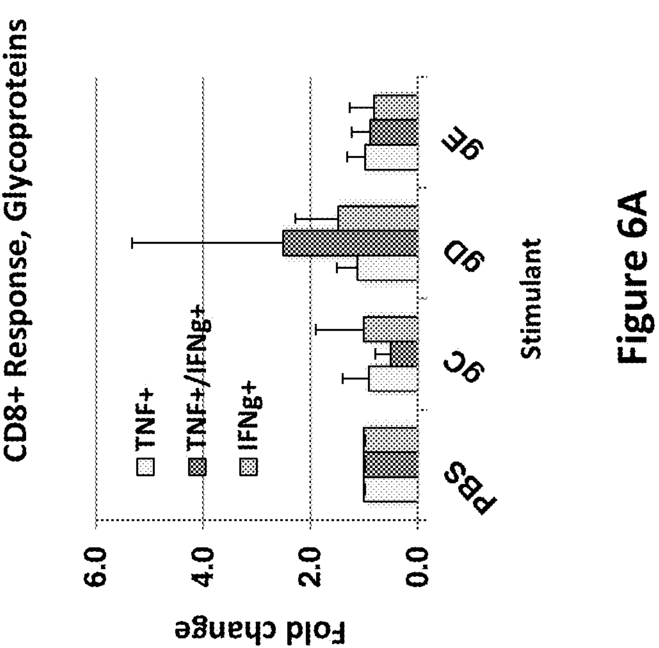

FIGS. 6A-6B. $CD8^+$ T cell responses to gC2, gD2 and gE2 mRNA, each administered at a different intradermal site. Splenocytes were stimulated with subunit antigen glycoproteins (FIG. 6A) or 15 amino acid peptides with 11 overlapping amino acids to stimulate HSV-2 specific T cell responses (FIG. 6B). * indicates p<0.05 comparing gE pool 2 with DMSO control. Error bars represent SD.

Figures 7A, 7B:
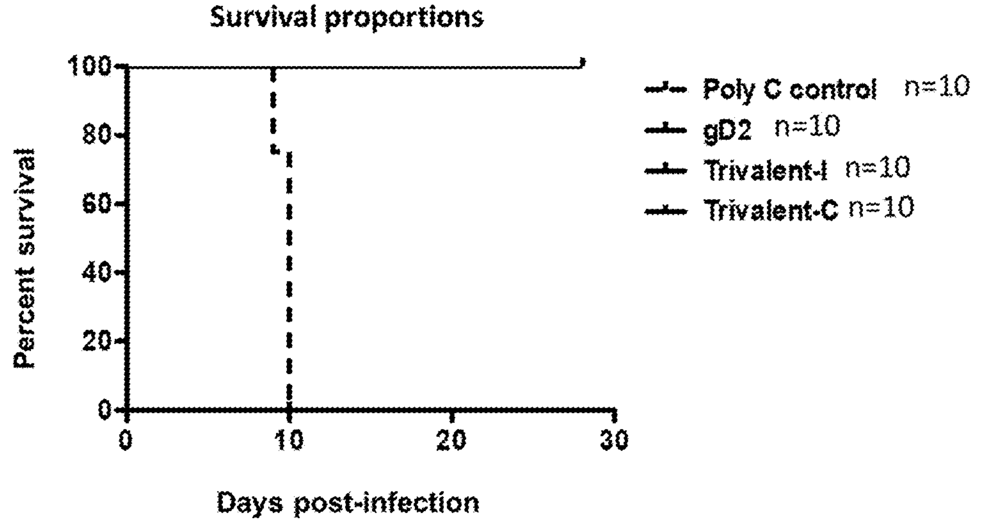

FIG. 7A. Survival in BALB/c mice immunized with mRNA twice at 28 day intervals and challenged intravaginally with HSV-2. Trivalent-I represents animals immunized with gC2/LNP, gD2/LNP, and gE2/LNP each given at different intradermal sites. Trivalent-C represents animals immunized with gC2, gD2 and gE2 combined into a single LNP for immunization.

FIG. 7B. Weight loss (−) or gain (+) and neurological signs in BALB/c mice immunized with mRNA twice at 28 day intervals and challenged intravaginally with HSV-2. Trivalent-I represents animals immunized with gC2/LNP, gD2/LNP, and gE2/LNP each given at different intradermal sites. Trivalent-C represents animals immunized with gC2, gD2 and gE2 combined into a single LNP for immunization.

Figures 8A, 8B:
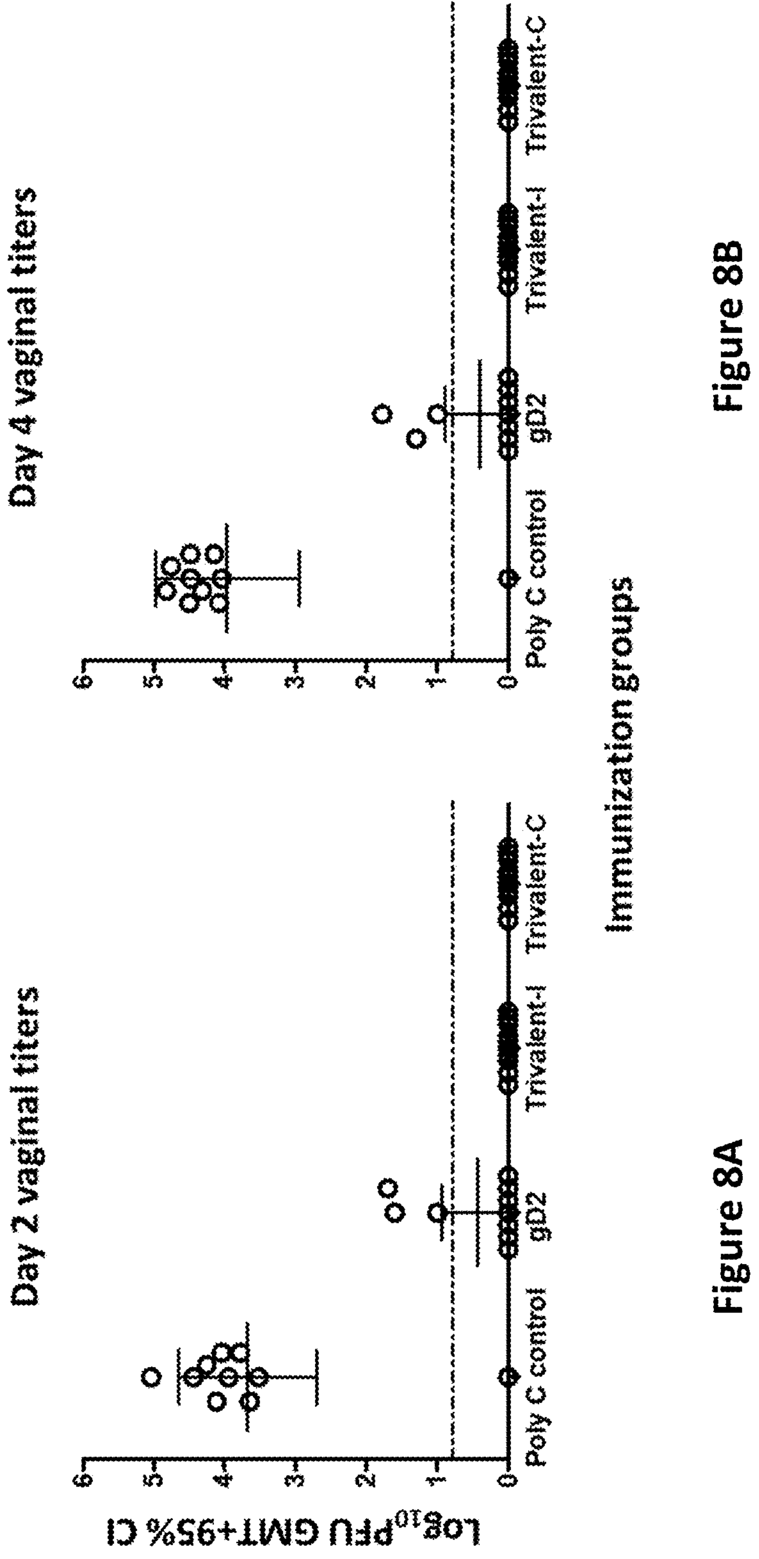

FIGS. 8A-8B. Vaginal viral titers in mRNA vaccinated mice after intravaginal challenge with HSV-2. Vaginal swab titers were obtained on Day 2 (FIG. 8A) and Day 4 (FIG. 8B) post-challenge. The dotted lines indicate the limit of detection of the assay at 7 PFU/ml.

Figure 9:
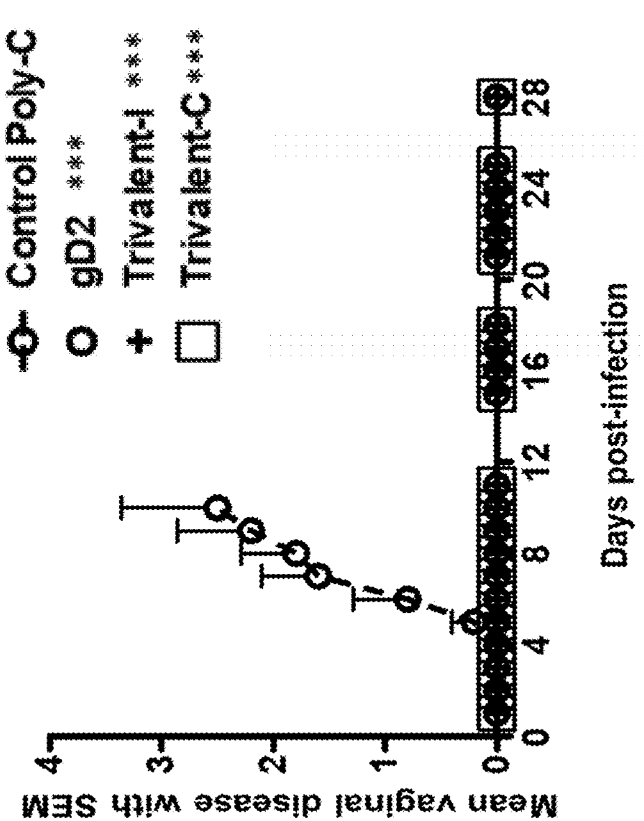

FIG. 9. Genital disease in mRNA-vaccinated mice after HSV-2 vaginal challenge. Mice were immunized with poly C as a control, or with gD2 mRNA/LNP, trivalent at individual sites for each glycoprotein mRNA (Trivalent-I) or trivalent with all three mRNAs combined (Trivalent-C). Genital disease was scored for 28 days. All animals in the poly C group died by day 10. ***, indicates p<0.001 comparing poly C with the other 3 groups.

Figure 10:
Figure 10:
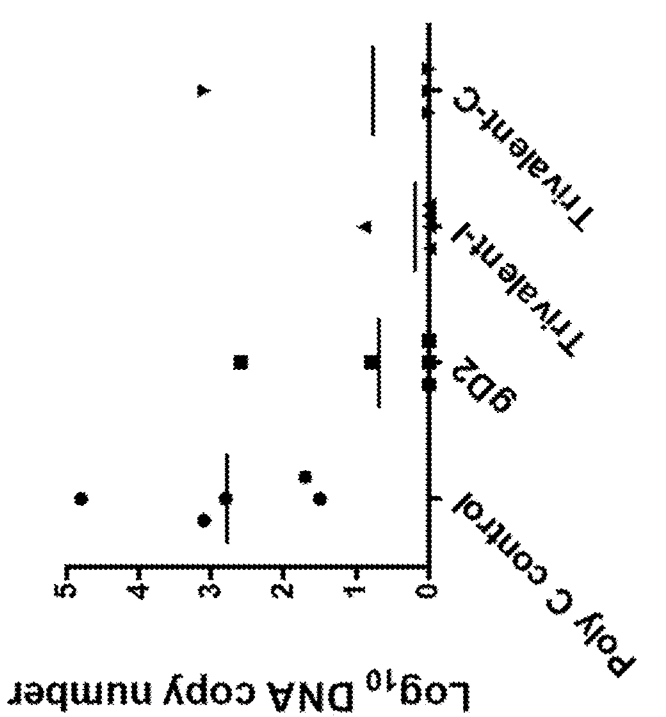

FIG. 10. HSV-2 DNA copies in dorsal root ganglia (DRG) in mRNA vaccinated mice on day 4 post challenge. HSV-2 DNA in DRG was measured by qPCR. DRG from 4 to 5 animals per group were evaluated for HSV-2 DNA at 4 days post challenge. The bars represent the mean values per group.

Figures 11A, 11B:
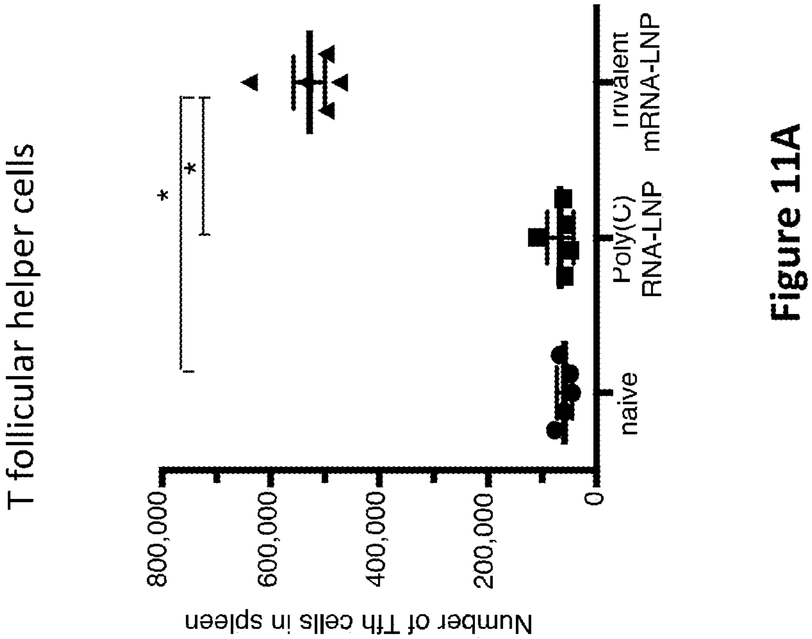

FIG. 11A. The trivalent mRNA-LNP vaccine induces a potent T follicular helper cell response in mice. BALB/c female mice were left un-immunized as naïve control animals or immunized intradermally twice at 28 day intervals with poly C mRNA-LNP or trivalent modified mRNA-LNP. The poly C mRNA controls received 10 μg Poly C mRNA-LNP divided into 4 aliquots and administered at 4 separate sites. The trivalent modified mRNA group received 10 g gC2 mRNA-LNP, 10 μg gD2 mRNA-LNP, and 10 μg gE2 mRNA-LNP each divided into 2 aliquots and each given at 2 sites. Two weeks after the second immunization, spleens were harvested from 5 animals per group and flow cytometry performed to detect T follicular helper (Tfh) cell responses (*p<0.05).

FIG. 11B. The trivalent mRNA-LNP vaccine induces a potent germinal center B cell response in mice. BALB/c female mice were left un-immunized as naïve control animals or immunized intradermally twice at 28 day intervals with poly C mRNA-LNP or trivalent modified mRNA-LNP. The poly C mRNA controls received 10 μg Poly C mRNA-LNP divided into 4 aliquots and administered at 4 separate sites. The trivalent modified mRNA group received 10 g gC2 mRNA-LNP, 10 μg gD2 mRNA-LNP, and 10 μg gE2 mRNA-LNP each divided into 2 aliquots and each given at 2 sites. Two weeks after the second immunization, spleens were harvested from 5 animals per group and flow cytometry performed to detect germinal center B cell responses (*p<0.05).

Figures 12A, 12B, 12C:
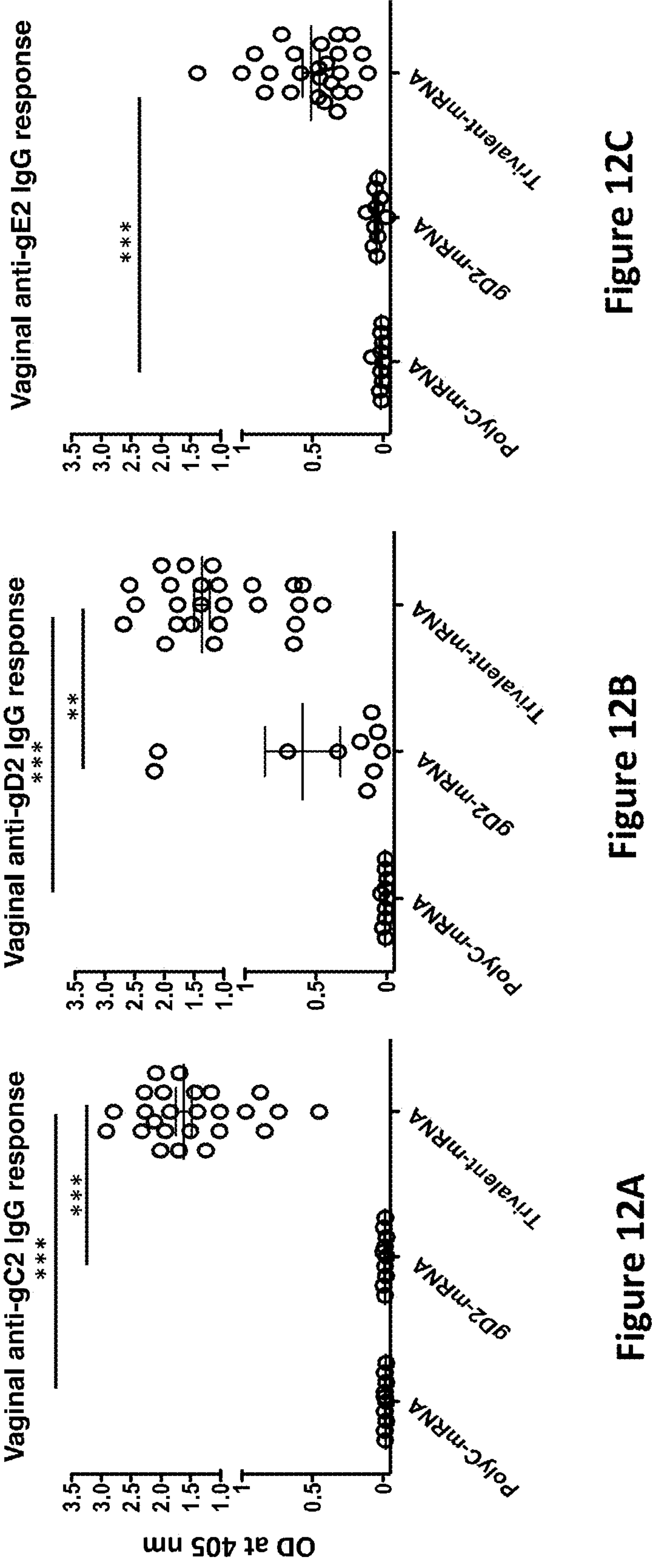

FIGS. 12A-12C. Genital mucosa IgG antibody responses. BALB/c mice were immunized intradermally twice at 28 day intervals with 10 μg of ploy C mRNA-LNP, 10 μg gD2 mRNA-LNP or 10 μg each of gC2, gD2, gE trivalent modified mRNA-LNP. The trivalent mRNA was combined and administered as 10 μg gC2 mRNA & 10 μg gD2 mRNA & 10 μg gE2 mRNA combined into LNP and divided into 4 aliquots and given at 4 sites. One month after the second immunization, 60 μl of media was introduced in the vaginal cavity and retrieved. IgG titers were determined at a 1:50 dilution of the vaginal wash fluids by ELISA to gC2 (FIG. 12A), gD2 (FIG. 12B), and gE2 (FIG. 12C) (n=10 mice in the poly C group, n=10 in the gD2 mRNA group and n=25 in the trivalent mRNA group; *p<0.001; p<0.01).

Figure 13:
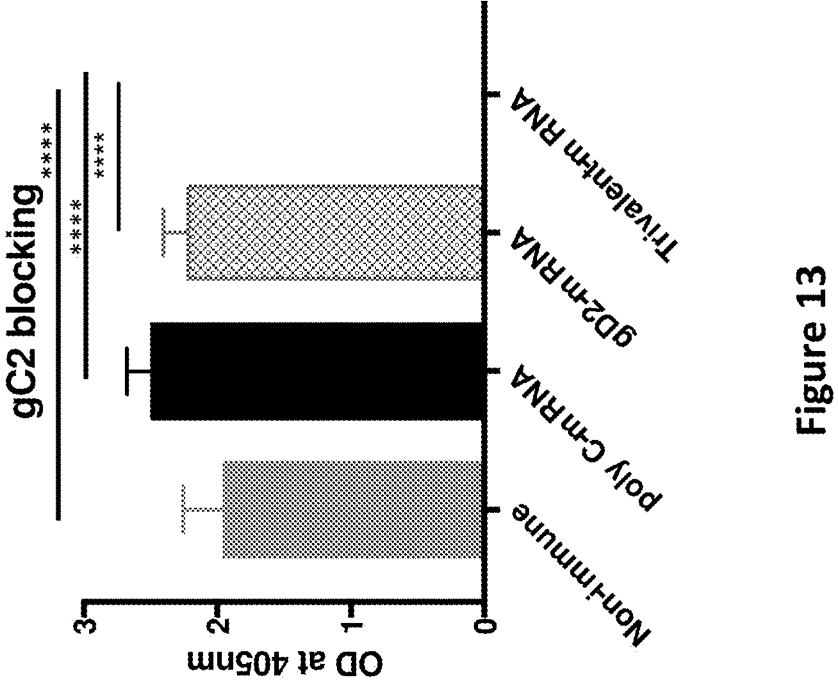

FIG. 13. The trivalent mRNA-LNP vaccine produces antibodies that block gC2 binding to complement component C3b. BALB/c mice were left unimmunized as a source of non-immune IgG, or immunized intradermally with poly C mRNA-LNP or trivalent mRNA-LNP. The poly C mRNA controls received 10 μg poly C mRNA-LNP divided into 4 aliquots and administered at 4 separate sites. The gD2 mRNA group received 10 μg gD2 mRNA-LNP administered as described for the poly C mRNA-LNP. The trivalent modified mRNA group received 10 μg gC2 mRNA-LNP, 10 μg gD2 mRNA-LNP, and 10 μg gE2 mRNA-LNP combined into LNP and divided into 4 aliquots and given at 4 sites. There were 10 mice in each group. Sera from the 10 mice were pooled and IgG was purified. The IgG was evaluated at 12 g/200 μl for its ability to block complement component C3b binding to gC2. (****p<0.0001).

Figures 14E, 14F:
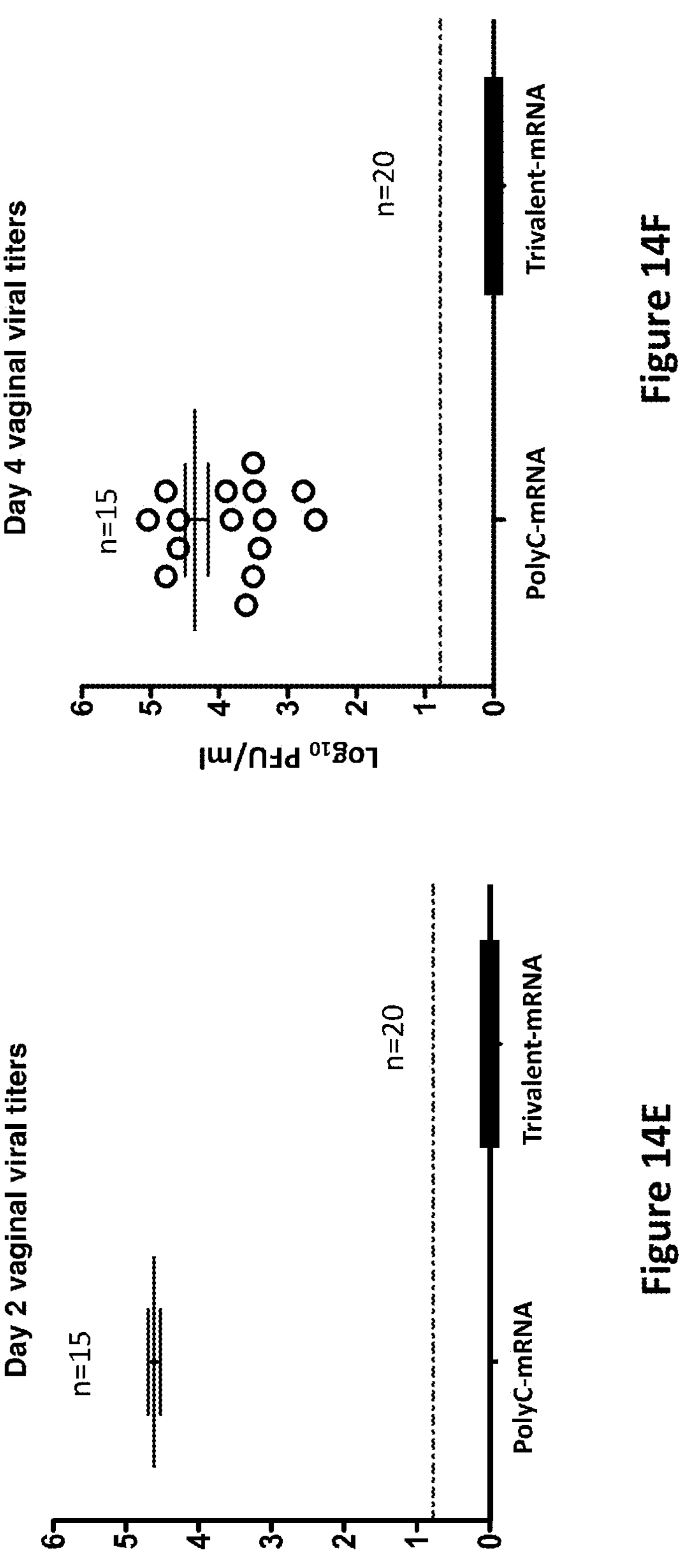

FIGS. 14A-14F. The trivalent mRNA vaccine provides outstanding protection in mice when the vaccine is administered intramuscularly. BALB/c mice were immunized intramuscularly with poly C mRNA-LNP as a control (15/group) or with trivalent mRNA containing 10 μg each of gC2, gD2 and gE2 mRNA-LNP (20/group). FIG. 14A presents data on mouse survival; FIG. 14B presents data on weight loss; FIG. 14C presents data on genital disease. DRG were harvested from nine poly C animals at the time of euthanasia between days 7 and 12 post-infection or at the end of the experiment on day 28 in the trivalent mRNA group. FIG. 14D presents data on HSV-2 DNA in DRG. FIG. 14E presents data on vaginal viral cultures on Day 2 and FIG. 14F presents data on vaginal viral cultures on Day 4. Difference between poly C and trivalent groups are significant, $p<0.001$ for FIGS. 14A-14F.

Figures 15A, 15B, 15C:
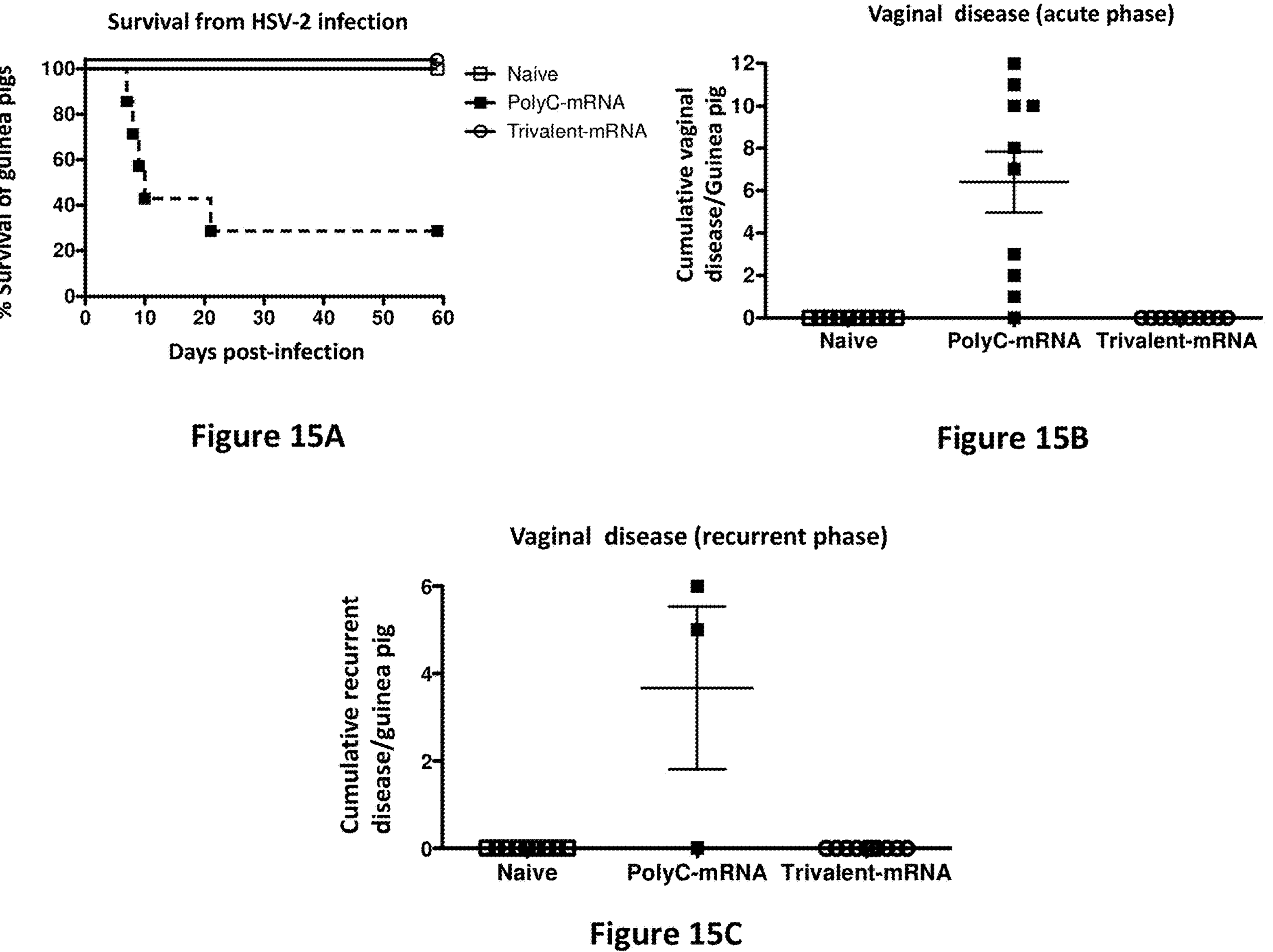

FIGS. 15A-15C. The trivalent mRNA vaccine is highly efficacious in the guinea pig genital infection model. Hartley Strain female guinea pigs were left unimmunized and uninfected (naive group, n=10), immunized three times intradermally at monthly intervals with 20 μg poly C mRNA-LNP (n=10) or with 20 μg each of gC2, gD2, gE modified mRNA-LNP (n=10). One month after the final immunization, animals in the poly C and trivalent mRNA groups were infected intravaginally with $5\times10^5$ PFU of HSV-2 strain MS (50 $LD_{50}$). Animals were observed for death, genital lesions during the acute phase of infection (days 1-14) and genital lesions during the recurrent phase of infection (days 15-60). FIG. 15A presents data on survival; FIG. 15B provides data on vaginal disease (acute phase); and FIG. 15C provides data on vaginal disease (recurrent phase).

DETAILED DESCRIPTION OF THE INVENTION

Compositions

In one embodiment, the present invention provides compositions comprising one or more modified mRNAs, wherein each of said modified mRNAs encodes a Herpes Simplex Virus (HSV) glycoprotein or immunogenic fragment thereof.

In one embodiment, the present invention provides a composition comprising one or more nucleoside modified mRNAs, wherein each of said modified mRNAs encodes a Herpes Simplex Virus (HSV) glycoprotein or immunogenic fragment thereof, and wherein said modified mRNA comprises one or more pseudouridine or pseudouridine family residues.

In one embodiment, the HSV glycoprotein comprises glycoprotein D (gD), glycoprotein C (gC), glycoprotein E (gE), glycoprotein B (gB), glycoprotein H (gH), glycoprotein L (gL) glycoprotein I (gI), or a combination thereof.

Thus, in one embodiment, the present invention provides a composition comprising one or more modified mRNAs encoding HSV gD, gC, gE, gB, gH, gL, gI, or immunogenic fragments thereof. In one embodiment, the modified mRNAs comprise pseudouridine-modified mRNAs.

In one embodiment, the present invention provides compositions comprising a modified mRNA encoding HSV gD or fragment thereof. In another embodiment, the present invention provides compositions comprising a modified mRNA encoding HSV gC or fragment thereof. In another embodiment, the present invention provides compositions comprising a modified mRNA encoding HSV gE or fragment thereof. In another embodiment, the present invention provides compositions comprising a modified mRNA encoding HSV gB or fragment thereof. In another embodiment, the present invention provides compositions comprising a modified mRNA encoding HSV gH or fragment thereof. In another embodiment, the present invention provides compositions comprising a modified mRNA encoding HSV gL or fragment thereof. In another embodiment, the present invention provides compositions comprising a modified mRNA encoding HSV gI or fragment thereof.

In one embodiment, the present invention provides a composition comprising: (a) a modified mRNA encoding HSV gD or fragment thereof; and (b) a modified mRNA encoding HSV gC or fragment thereof.

In another embodiment, the present invention provides a composition comprising: (a) a modified mRNA encoding HSV gD or fragment thereof; and (b) a modified mRNA encoding HSV gE or fragment thereof.

In another embodiment, the present invention provides a composition comprising: (a) a modified mRNA encoding HSV gC or fragment thereof; and (b) a modified mRNA encoding HSV gE or fragment thereof.

In another embodiment, the present invention provides a composition comprising: (a) a modified mRNA encoding HSV gD or fragment thereof; (b) a modified mRNA encoding HSV gC or fragment thereof, and (c) a modified mRNA encoding HSV gE or fragment thereof.

In another embodiment, the present invention provides a composition comprising: (a) a modified mRNA encoding HSV gD or fragment thereof; (b) a modified mRNA encoding HSV gC or fragment thereof, (c) a modified mRNA encoding HSV gE or fragment thereof, and (d) a modified mRNA encoding HSV gB or fragment thereof.

In one embodiment, the HSV glycoproteins are HSV-2 glycoproteins. In another embodiment, the HSV glycoproteins are HSV-1 glycoproteins. In one embodiment, the HSV glycoproteins comprise both HSV-2 glycoproteins and HSV-1 glycoproteins. In another embodiment, the HSV glycoproteins comprise a mixture of HSV-2 glycoproteins and HSV-1 glycoproteins.

In one embodiment, the present invention provides compositions comprising a modified mRNA encoding HSV-2 gD or fragment thereof. In another embodiment, the present invention provides compositions comprising a modified mRNA encoding HSV-2 gC or fragment thereof. In another embodiment, the present invention provides compositions comprising a modified mRNA encoding HSV-2 gE or fragment thereof. In another embodiment, the present invention provides compositions comprising a modified mRNA encoding HSV-2 gE or fragment thereof. In another embodiment, the present invention provides compositions comprising a modified mRNA encoding HSV-2 gB or fragment thereof. In another embodiment, the present invention provides compositions comprising a modified mRNA encoding HSV-2 gH or fragment thereof. In another embodiment, the present invention provides compositions comprising a modified mRNA encoding HSV-2 gL or fragment thereof. In another embodiment, the present invention provides compositions comprising a modified mRNA encoding HSV-2 gI or fragment thereof.

In one embodiment, the present invention provides a composition comprising: (a) a modified mRNA encoding HSV-2 gD or fragment thereof, and (b) a modified mRNA encoding HSV-2 gC or fragment thereof.

In another embodiment, the present invention provides a composition comprising: (a) a modified mRNA encoding HSV-2 gD or fragment thereof, and (b) a modified mRNA encoding HSV-2 gE or fragment thereof.

In another embodiment, the present invention provides a composition comprising: (a) a modified mRNA encoding HSV-2 gC or fragment thereof; and (b) a modified mRNA encoding HSV-2 gE or fragment thereof.

In another embodiment, the present invention provides a composition comprising: (a) a modified mRNA encoding HSV-2 gD or fragment thereof; (b) a modified mRNA encoding HSV-2 gC or fragment thereof, and (c) a modified mRNA encoding HSV-2 gE or fragment thereof.

In one embodiment, the present invention provides compositions comprising a modified mRNA encoding HSV-1 gD or fragment thereof. In another embodiment, the present invention provides compositions comprising a modified mRNA encoding HSV-1 gC or fragment thereof. In another embodiment, the present invention provides compositions comprising a modified mRNA encoding HSV-1 gE or fragment thereof. In another embodiment, the present invention provides compositions comprising a modified mRNA encoding HSV-1 gE or fragment thereof. In another embodiment, the present invention provides compositions comprising a modified mRNA encoding HSV-1 gB or fragment thereof. In another embodiment, the present invention provides compositions comprising a modified mRNA encoding HSV-1 gH or fragment thereof. In another embodiment, the present invention provides compositions comprising a modified mRNA encoding HSV-1 gL or fragment thereof. In another embodiment, the present invention provides compositions comprising a modified mRNA encoding HSV-1 gI or fragment thereof.

In one embodiment, the present invention provides a composition comprising: (a) a modified mRNA encoding HSV-1 gD or fragment thereof, and (b) a modified mRNA encoding HSV-1 gC or fragment thereof.

In another embodiment, the present invention provides a composition comprising: (a) a modified mRNA encoding HSV-1 gD or fragment thereof, and (b) a modified mRNA encoding HSV-1 gE or fragment thereof.

In another embodiment, the present invention provides a composition comprising: (a) a modified mRNA encoding HSV-1 gC or fragment thereof; and (b) a modified mRNA encoding HSV-1 gE or fragment thereof.

In another embodiment, the present invention provides a composition comprising: (a) a modified mRNA encoding HSV-1 gD or fragment thereof; (b) a modified mRNA encoding HSV-1 gC or fragment thereof, and (c) a modified mRNA encoding HSV-1 gE or fragment thereof.

In one embodiment, any of the compositions as described herein consists essentially of one or more modified mRNAs, wherein each of said modified mRNAs encodes an HSV glycoprotein or immunogenic fragment thereof. In another embodiment, any of the compositions as described herein consists of one or more modified mRNAs, wherein each of said modified mRNAs encodes an HSV glycoprotein or immunogenic fragment thereof.

In another embodiment, the present invention provides compositions comprising a modified mRNA encoding an HSV gD protein, a modified mRNA encoding an HSV gC protein, a modified mRNA encoding an HSV gE protein and modified mRNAs encoding one or more additional HSV glycoproteins. In one embodiment, said additional HSV glycoproteins comprise gB or immunogenic fragment thereof, gH or immunogenic fragment thereof, gL or immunogenic fragment thereof, gI or immunogenic fragment thereof, or any combination thereof. In one embodiment, said additional HSV glycoproteins comprise glycoprotein M (gM), glycoprotein N (gN), glycoprotein K (gK), glycoprotein G (gG), glycoprotein J (gJ), or an immunogenic fragment thereof.

In one embodiment, compositions of the present invention and for use in the methods of the present invention comprise both HSV-2 glycoproteins or glycoprotein fragments and HSV-1 glycoproteins or glycoprotein fragments. In another embodiment, compositions of the present invention and for use in the methods of the present invention comprise a mixture of HSV-2 glycoproteins or glycoprotein fragments and HSV-1 glycoproteins or glycoprotein fragments. For example, in one embodiment, a composition of the present invention comprises HSV-2 gC, HSV-1 gD, and HSV-2 gE, or fragments thereof. In another embodiment, a composition of the present invention comprises HSV-1 gC, HSV-2 gD, and HSV-2 gE, or fragments thereof. In another embodiment, a composition of the present invention comprises HSV-2 gC, HSV-2 gD, and HSV-1 gE, or fragments thereof. In another embodiment, a composition of the present invention comprises HSV-1 gC, HSV-1 gD, and HSV-2 gE, or fragments thereof. In another embodiment, a composition of the present invention comprises HSV-1 gC, HSV-2 gD, and HSV-1 gE, or fragments thereof. In another embodiment, a composition of the present invention comprises HSV-2 gC, HSV-1 gD, and HSV-1 gE, or fragments thereof.

In another embodiment, the compositions of the present invention comprise one or more additional HSV-1 glycoproteins or HSV-2 glycoproteins or both HSV-1 and HSV-2 glycoproteins, as described herein. For example, in one embodiment, a composition of the present invention comprising HSV-2 gC, HSV-1 gD, and HSV-2 gE may further comprise HSV-1 gI. In another embodiment, a composition of the present invention comprising HSV-2 gC, HSV-2 gD, and HSV-2 gE may further comprise HSV-1 gB. Each of the possible combinations of HSV-1 and HSV-2 glycoproteins represents a separate embodiment of the invention.

"Encoding" refers, in one embodiment, to an RNA molecule that contains a gene that encodes the protein of interest. In another embodiment, the RNA molecule comprises a protein coding sequence that encodes the protein of interest. In another embodiment, one or more other proteins is also encoded. In another embodiment, the protein of interest is the only protein encoded. Each possibility represents a separate embodiment of the present invention.

"Immunogenic fragment" refers, in another embodiment, to a portion of a protein that is immunogenic and elicits a protective immune response when administered to a subject.

In one embodiment, "immunogenicity" or "immunogenic" is used herein to refer to the innate ability of a protein, peptide, nucleic acid, antigen or organism to elicit an immune response in an animal when the protein, peptide, nucleic acid, antigen or organism is administered to the animal. Thus, "enhancing the immunogenicity" in one embodiment, refers to increasing the ability of a protein, peptide, nucleic acid, antigen or organism to elicit an immune response in an animal when the protein, peptide, nucleic acid, antigen or organism is administered to an animal. The increased ability of a protein, peptide, nucleic acid, antigen or organism to elicit an immune response can be measured by, in one embodiment, a greater number of antibodies to a protein, peptide, nucleic acid, antigen or organism, a greater diversity of antibodies to an antigen or organism, a greater number of T-cells specific for a protein, peptide, nucleic acid, antigen or organism, a greater cytotoxic or helper T-cell response to a protein, peptide, nucleic acid, antigen or organism, and the like.

In one embodiment, an immunogenic polypeptide is also antigenic. "Antigenic" refers, in another embodiment, to a peptide capable of specifically interacting with an antigen recognition molecule of the immune system, e.g. an immunoglobulin (antibody) or T cell antigen receptor. An antigenic peptide contains, in another embodiment, an epitope of at least about 8 amino acids (AA). An antigenic portion of a polypeptide, also called herein the epitope in one embodiment, can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

In one embodiment, "functional" within the meaning of the invention, is used herein to refer to the innate ability of a protein, peptide, nucleic acid, fragment or a variant thereof to exhibit a biological activity or function. In one embodiment, such a biological function is its binding property to an interaction partner, e.g., a membrane-associated receptor, and in another embodiment, its trimerization property. In the case of functional fragments and the functional variants of the invention, these biological functions may in fact be changed, e.g., with respect to their specificity or selectivity, but with retention of the basic biological function.

In one embodiment, the term "fragment" is used herein to refer to a protein or polypeptide that is shorter or comprises fewer amino acids than the full length protein or polypeptide. In another embodiment, fragment refers to a nucleic acid encoding the protein fragment that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In another embodiment, the fragment is an immunogenic intrasequential section of the protein, peptide or nucleic acid. In another embodiment, the fragment is a functional intrasequential section within the protein, peptide or nucleic acid. In another embodiment, the fragment is an N-terminal immunogenic fragment. In one embodiment, the fragment is a C-terminal immunogenic fragment. In another embodiment, the fragment is an N-terminal functional fragment. In another embodiment, the fragment is a C-terminal functional fragment. In another embodiment, the fragment contains pieces of the protein linked together or pieces of multiple proteins linked together.

Thus, in one embodiment, an "immunogenic fragment" of a protein as described in the present invention refers to a portion of the protein that is immunogenic, in one embodiment and in another embodiment, elicits a protective immune response when administered to a subject.

In another aspect, the present invention provides compositions comprising modified mRNAs, wherein each of said modified mRNAs encodes a) HSV glycoprotein D (gD) or an immunogenic fragment thereof, b) HSV glycoprotein C (gC) or an immunogenic fragment thereof, c) HSV glycoprotein E (gE) or an immunogenic fragment thereof, or any combination thereof.

In one embodiment, the present invention provides a composition comprising a modified mRNA encoding an HSV gD or an immunogenic fragment thereof, a modified mRNA encoding an HSV gC or an immunogenic fragment thereof, and a modified mRNA encoding an HSV gE or an immunogenic fragment thereof.

In one embodiment, compositions of modified mRNA encoding gD-1 are protective against HSV-1 infection. Further, combination compositions of modified mRNA encoding gC-1/gD-1/gE-1 confer superior protection compared with compositions containing modified mRNA encoding gC-1 alone, gD-1 alone, or gE-1 alone. Further, as provided herein, compositions of modified mRNA encoding gD-2 are protective against HSV-2 infection (FIGS. 7-10). Further, combination compositions of modified mRNA encoding gC-2/gD-2/gE-2 confer superior protection compared with compositions containing modified mRNA encoding gC-2 alone, gD-2 alone, or gE-2 alone.

In another embodiment, inclusion of a modified mRNA encoding gC, and/or a modified mRNA encoding gE in the composition of the present invention increases the efficaciousness of anti-gD antibodies elicited by the composition. In another embodiment, inclusion of a modified mRNA encoding gC, and/or a modified mRNA encoding gE in the composition of the present invention increases the dose of modified mRNA encoding gD required to elicit antibodies that inhibit binding of gD to a cellular receptor. In another embodiment, inclusion of a modified mRNA encoding gC, and/or a modified mRNA encoding gE in the composition of the present invention decreases the dose of modified mRNA encoding gD required to elicit antibodies that inhibit binding of gD to a cellular receptor when a dose of modified mRNA encoding a gD is administered separately from modified mRNAs encoding the gC protein or gE protein.

In another embodiment, inclusion of a modified mRNA encoding gC, and/or a modified mRNA encoding gE in the composition of the present invention enhances the effectiveness of an innate immune response. In another embodiment, the innate immune response is an antibody-mediated immune response. In another embodiment, the innate immune response is a non-antibody-mediated immune response. In another embodiment, the innate immune response is an NK (natural killer) cell response. In another embodiment, the innate immune response is any other innate immune response known in the art.

In another embodiment, inclusion of a modified mRNA encoding gC, and/or a modified mRNA encoding gE in the composition of the present invention increases the efficaciousness of antibodies elicited by the composition against one of the above glycoproteins. In another embodiment, inclusion of a modified mRNA encoding gC, and/or a modified mRNA encoding gE in the composition of the present invention decreases the dose of one of the above glycoproteins required to elicit antibodies that inhibit binding of the glycoprotein to a cellular receptor thereof, when a dose of one of the glycoproteins is administered separately from one of the other glycoproteins.

Glycoprotein D

In one embodiment, a composition of the present invention comprises a modified mRNA encoding HSV-1 gD protein. In another embodiment, the composition comprises a modified mRNA encoding a fragment of an HSV-1 gD protein.

In one embodiment, the nucleotide sequence of the modified mRNA encoding an HSV-1 gD fragment comprises:

(SEQ ID NO: 1)

GGAAUAAAAGUCUCAACACAACAUAUACAAAACAAACGAAUCUCAAGCA

AUCAAGCAUUCUACUUCUAUUGCAGCAAUUUAAAUCAUUUCUUUUAAAG

CAAAAGCAAUUUUCUGAAAAUUUUCACCAUUUACGAACGAUAGCAUGCG

CAUGCAGCUGCUGCUGCUGAUCGCCCUGUCCCUGGCCCUGGUGACCAAC

UCCAAGUACGCCCUGGCCGACGCCUCCCUGAAGAUGGCCGACCCCAACC

GCUUCCGCGGCAAGGACCUGCCCGUGCUGGACCAGCUGACCGACCCCCC

CGGCGUGCGCCGCGUGUACCACAUCCAGGCCGGCCUGCCCGACCCCUUC

CAGCCCCCCUCCCUGCCCAUCACCGUGUACUACGCCGUGCUGGAGCGCG

CCUGCCGCUCCGUGCUGCUGAACGCCCCCUCCGAGGCCCCCCAGAUCGU

-continued

```
GCGCGGCGCCUCCGAGGACGUGCGCAAGCAGCCCUACAACCUGACCAUC
GCCUGGUUCCGCAUGGGCGGCAACUGCGCCAUCCCCAUCACCGUGAUGG
AGUACACCGAGUGCUCCUACAACAAGUCCCUGGGCGCCUGCCCCAUCCG
CACCCAGCCCCGCUGGAACUACUACGACUCCUUCUCCGCCGUGUCCGAG
GACAACCUGGGCUUCCUGAUGCACGCCCCCGCCUUCGAGACCGCCGGCA
CCUACCUGCGCCUGGUGAAGAUCAACGACUGGACCGAGAUCACCCAGUU
CAUCCUGGAGCACCGCGCCAAGGGCUCCUGCAAGUACGCCCUGCCCCUG
CGCAUCCCCCCCUCCGCCUGCCUGUCCCCCCAGGCCUACCAGCAGGGCG
UGACCGUGGACUCCAUCGGCAUGCUGCCCCGCUUCAUCCCCGAGAACCA
GCGCACCGUGGCCGUGUACUCCCUGAAGAUCGCCGGCUGGCACGGCCCC
AAGGCCCCCUACACCUCCACCCUGCUGCCCCCCGAGCUGUCCGAGACCC
CCAACGCCACCCAGCCCGAGCUGGCCCCCGAGGACCCCGAGGACUCCGC
CCUGCUGGAGGACCCCGUGGGCACCGUGGCCCCCCAGAUCCCCCCCAAC
UGGCACAUCCCCUCCAUCCAGGACGCCGCCACCCCCUACUAACUAGUAG
UGACUGACUAGGAUCUGGUUACCACUAAACCAGCCUCAAGAACACCCGA
AUGGAGUCUCUAAGCUACAUAAUACCAACUUACACUUACAAAAUGUUGU
CCCCCAAAAUGUAGCCAUUCGUAUCUGCUCCUAAUAAAAAGAAAGUUUC
UUCACAUUCUAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAC
```

In one embodiment, all uridine residues are 1-methyl-pseudouridine. In one embodiment, underlined residues represent 5' untranslated sequences. In one embodiment, bold residues represent a signal sequence (leader sequence) to assist expression of the gD1 fragment. In one embodiment, italicized residues represent 3' untranslated sequences and poly adenylation tail.

In another embodiment, the nucleotide sequence of the modified mRNA encoding an HSV-1 gD fragment lacks the 5' untranslated sequences, the signal sequence, the 3' untranslated sequences, the poly adenylation tail, or a combination thereof.

In one embodiment, the HSV-1 gD fragment encoded by modified mRNA utilized in the methods and compositions of the present invention comprises amino acids 26-331 of gD from HSV-1 Patton strain, as set forth in the following amino acid sequence:

```
                                           (SEQ ID NO: 2)
KYALADASLKMADPNRFRGKDLPVLDQLTDPPGVRRVYHIQAGLPDPFQ
PPSLPITVYYAVLERACRSVLLNAPSEAPQIVRGASEDVRKQPYNLTIA
WFRMGGNCAIPITVMEYTECSYNKSLGACPIRTQPRWNYYDSFSAVSED
NLGFLMHAPAFETAGTYLRLVKINDWTEITQFILEHRAKGSCKYALPLR
IPPSACLSPQAYQQGVTVDSIGMLPRFIPENQRTVAVYSLKIAGWHGPK
APYTSTLLPPELSETPNATQPELAPEDPEDSALLEDPVGTVAPQIPPNW
HIPSIQDAATPY
```

In one embodiment, the full length HSV-1 gD encoded by modified mRNA utilized in the methods and compositions of the present invention comprises the following amino acid sequence:

```
                                           (SEQ ID NO: 3)
MGGAAARLGAVILFVVIVGLHGVRGKYALADASLKLADPNRFRRKDLPV
LDQLTDPPGVRRVYHIQAGLPDPFQPPSLPITVYYAVLERACRSVLLNA
PSEAPQIVRGASEDVRKQPYNLTIAWFRMGGNCAIPITVMEYTECSYNK
SLGACPIRTQPRWNYYDSFSAVSEDNLGFLMHAPAFETAGTYLRLVKIN
DWTEITQFILEHRAKGSCKYALPLRIPPSACLSPQAYQQGVTVDSIGML
PRFIPENQRTVAVYSLKIAGWHGPKAPYTSTLLPPELSETPNATQPELA
PEAPEDSALLEDPVGTVAPQIPPNWHIPSIQDAATPYHPPATPNNMGLI
AGAVGGSLLAALVICGIVYWMRRRTQKAPKRIRLPHIREDDQPSSHQPL
FY
```

In another embodiment, the HSV-1 gD encoded by modified mRNA utilized in the methods and compositions of the present invention comprises the amino acid sequences as set forth in any one of the following GenBank Accession Numbers: AAL90884.1 (KHS2 strain), AAL90883.1 (KHS1 strain), AAK93950.1 (F strain), AAB59754.1 (F strain), AAA19631.1 (mutant strain not identified), AAA19630.1 (mutant strain not identified), or AAA19629.1 (strain not identified).

In another embodiment, the HSV-1 gD encoded by modified mRNA utilized in the methods and compositions of the present invention comprises the amino acid sequences as set forth in any of the following GenBank Accession Numbers: A1Z0Q5.2, AAA45780.1, AAA45785.1, AAA45786.1, AAA96682.1, AAK19597.1, AAN74642.1, ABI63524.1, ABM52978.1, ABM52979.1, ABM52980.1, ABM52981.1, ABM66847.1, ABM66848.1, ACM62295.1, ADD60053.1, ADD60130.1, ADM22389.1, ADM22466.1, ADM22542.1, ADM22619.1, ADM22696.1, ADM22773.1, ADM22849.1, ADM22926.1, ADM23003.1, ADM23079.1, ADM23155.1, ADM23231.1, ADM23309.1, ADM23383.1, ADM23457.1, ADM23531.1, ADM23605.1, ADM23680.1, ADM23755.1, ADM23831.1, AEQ77097.1, AER37647.1, AER37715.1, AER37786.1, AER37857.1, AER37929.1, AER38000.1, AER38070.1, AFE62894.1, AFH41180.1, AFI23657.1, AFK50415.1, AFP86430.1, AGZ01928.1, AIR95858.1, AJE60009.1, AJE60080.1, AJE60151.1, AJE60222.1, AJE60293.1, AJE60439.1, AKE48645.1, AKG59246.1, AKG59318.1, AKG59391.1, AKG59462.1, AKG59536.1, AKG59609.1, AKG59682.1, AKG59755.1, AKG59826.1, AKG59898.1, AKG59972.1, AKG60046.1, AKG60118.1, AKG60189.1, AKG60261.1, AKG60334.1, AKG60404.1, AKG60474.1, AKG60546.1, AKG60620.1, AKG60692.1, AKG60763.1, AKG60835.1, AKG60906.1, AKG60978.1, AKG61050.1, AKG61123.1, AKG61194.1, AKG61267.1, AKG61339.1, AKG61411.1, AKG61484.1, AKG61556.1, AKG61629.1, AKG61703.1, AKG61774.1, AKG61847.1, AKG61920.1, AKG61993.1, AKH80463.1, AKH80536.1, ALM22635.1, ALM22709.1, ALM22783.1, ALM22857.1, ALO18662.1, ALO18738.1, AMB65662.1, AMB65735.1, AMB65809.1, AMB65885.1, AMB65956.1, AMN09832.1, ANN83964.1, ANN84041.1, ANN84117.1, ANN84194.1, ANN84271.1, ANN84348.1, ANN84424.1, ANN84500.1, ANN84577.1, ANN84653.1, ANN84730.1, ANN84806.1, ANN84883.1, ANN84959.1, ANN85036.1, ANN85112.1, ANN85187.1, ANN85264.1, ANN85341.1, ANN85416.1, ANN85494.1, ANN85571.1, ANN85648.1, ANN85724.1, ANN85801.1, AOY34093.1, AOY34141.1, AOY34243.1, AOY34271.1, AOY34337.1, AOY36685.1, ARB08957.1, ARO37961.1, ARO37962.1, ARO37963.1, ARO37964.1, ARO37965.1, ARO37966.1, ARO37967.1, ARO37968.1, ARO37969.1, ARO37970.1, ARO37971.1, ARO37972.1, ARO37973.1, ARO37974.1, ARO37975.1, ARO37976.1, ARO37977.1, ARO37978.1, ARO37979.1, ARO37980.1, ARO37981.1, ARO37982.1, ARO37983.1, ARO37984.1, ARO37985.1, ARO37986.1, ARO37987.1, ARO37988.1, ARO37989.1, ARO37990.1, ARO37991.1, ARO37992.1, ARO37993.1, ARO37994.1, ARO37995.1, ARO37996.1, ARO37997.1, ARO37998.1, ARO37999.1, ASM47664.1, ASM47741.1, ASM47818.1, ASM47893.1, BAM73419.1, CAA26060.1, CAA32283.1, CAA32284.1, CAA32289.1, CAA38245.1, CAT05431.1, P06476.1, P36318.1, P57083.1, P68331.1, Q05059.1, Q69091.1, SBO07792.1, SBO07819.1, SBO07855.1, SBO07869.1, SBO07887.1, SBO07908.1, SBS69553.1, SBS69561.1, SBS69579.1, SBS69625.1, SBS69688.1, SBS69694.1, SBS69717.1, SBS69727.1, SBS69811.1, SBT69395.1, SCL76902.1, VGBEDZ, or YP_009137141.1.

In another embodiment, the composition comprises a modified mRNA encoding an HSV-2 gD protein. In another embodiment, the composition comprises a modified mRNA encoding a fragment of an HSV-2 gD protein.

In one embodiment, the nucleotide sequence of the modified mRNA encoding an HSV-2 gD fragment comprises:

(SEQ ID NO: 4)

GGAAUAAAAGUCUCAACACAACAUAUACAAAACAAACGAAUCUCAAGCA
AUCAAGCAUUCUACUUCUAUUGCAGCAAUUUAAAUCAUUUCUUUUAAAG
CAAAAGCAAUUUUCUGAAAAUUUUCACCAUUUACGAACGAUAGCAUGAC
CCGCCUGACCGUGCUGGCCCUGCUGGCCGGCCUGCUGGCCUCCUCCCGC
GCCAAGUACGCCCUGGCCGACCCCUCCCUGAAGAUGGCCGACCCCAACC
GCUUCCGCGGCAAGAACCUGCCCGUGCUGGACCAGCUGACCGACCCCCC
CGGCGUGAAGCGCGUGUACCACAUCCAGCCCUCCCUGGAGGACCCCUUC
CAGCCCCCCUCCAUCCCCAUCACCGUGUACUACGCCGUGCUGGAGCGCG
CCUGCCGCUCCGUGCUGCUGCACGCCCCCUCCGAGGCCCCCCAGAUCGU
GCGCGGCGCCUCCGACGAGGCCCGCAAGCACACCUACAACCUGACCAUC
GCCUGGUACCGCAUGGGCGACAACUGCGCCAUCCCCAUCACCGUGAUGG
AGUACACCGAGUGCCCCUACAACAAGUCCCUGGGCGUGUGCCCCAUCCG
CACCCAGCCCCGCUGGUCCUACUACGACUCCUUCUCCGCCGUGUCCGAG
GACAACCUGGGCUUCCUGAUGCACGCCCCCGCCUUCGAGACCGCCGGCA
CCUACCUGCGCCUGGUGAAGAUCAACGACUGGACCGAGAUCACCCAGUU
CAUCCUGGAGCACCGCGCCCGCGCCUCCUGCAAGUACGCCCUGCCCCUG
CGCAUCCCCCCCGCCGCCUGCCUGACCUCCAAGGCCUACCAGCAGGGCG
UGACCGUGGACUCCAUCGGCAUGCUGCCCCGCUUCAUCCCCGAGAACCA
GCGCACCGUGGCCCUGUACUCCCUGAAGAUCGCCGGCUGGCACGGCCCC
AAGCCCCCCUACACCUCCACCCUGCUGCCCCCCGAGCUGUCCGACACCA
CCAACGCCACCCAGCCCGAGCUGGUGCCCGAGGACCCCGAGGACUCCGC
CCUGCUGGAGGACCCCGCCGGCACCGUGUCCUCCCAGAUCCCCCCCAAC

-continued

UGGCACAUCCCCUCCAUCCAGGACGUGGCCCCCCACCACUAA*CUAGUAG*
*UGACUGACUAGGAUCUGGUUACCACUAAACCAGCCUCAAGAACACCCGA*
*AUGGAGUCUCUAAGCUACAUAAUACCAACUUACACUUACAAAAUGUUGU*
*CCCCCAAAAUGUAGCCAUUCGUAUCUGCUCCUAAUAAAAAGAAAGUUUC*
*UUCACAUUCUAAAAAAAAAAAAAAAAAAAAAAAAAAAAAAAAAAAAAAAA*
*AAAAAAAAAAAAAAAAAAAAAAAAAAAAAAAAAAAAAAAAAAAAAAAAAA*
*AAAAAAAAAAAAAC*

In one embodiment, all uridine residues are 1-methyl-pseudouridine. In one embodiment, underlined residues represent 5' untranslated sequences. In one embodiment, bold residues represent a signal sequence (leader sequence) to assist expression of the gD2 fragment. In one embodiment, italicized residues represent 3' untranslated sequences and poly adenylation tail.

In another embodiment, the nucleotide sequence of the modified mRNA encoding an HSV-2 gD fragment lacks the 5' untranslated sequences, the signal sequence, the 3' untranslated sequences, the poly adenylation tail, or a combination thereof.

In one embodiment, the HSV-2 gD fragment encoded by modified mRNA utilized in the methods and compositions of the present invention comprises amino acids 26-331 of gD from HSV-2 strain 333, as set forth in the following amino acid sequence:

(SEQ ID NO: 5)

KYALADPSLKMADPNRFRGKNLPVLDQLTDPPGVKRVYHIQPSLEDPFQ
PPSIPITVYYAVLERACRSVLLHAPSEAPQIVRGASDEARKHTYNLTIA
WYRMGDNCAIPITVMEYTECPYNKSLGVCPIRTQPRWSYYDSFSAVSED
NLGFLMHAPAFETAGTYLRLVKINDWTEITQFILEHRARASCKYALPLR
IPPAACLTSKAYQQGVTVDSIGMLPRFIPENQRTVALYSLKIAGWHGPK
PPYTSTLLPPELSDTTNATQPELVPEDPEDSALLEDPAGTVSSQIPPNW
HIPSIQDVAPHH.

In one embodiment, the full length HSV-2 gD encoded by modified mRNA utilized in the methods and compositions of the present invention comprises the following amino acid sequence:

(SEQ ID NO: 6)

MGRLTSGVGTAALLVVAVGLRVVCAKYALADPSLKMADPNRFRGKNLPV
LDQLTDPPGVKRVYHIQPSLEDPFQPPSIPITVYYAVLERACRSVLLHA
PSEAPQIVRGASDEARKHTYNLTIAWYRMGDNCAIPITVMEYTECPYNK
SLGVCPIRTQPRWSYYDSFSAVSEDNLGFLMHAPAFETAGTYLRLVKIN
DWTEITQFILEHRARASCKYALPLRIPPAACLTSKAYQQGVTVDSIGML
PRFIPENQRTVALYSLKIAGWHGPKPPYTSTLLPPELSDTTNATQPELV
PEDPEDSALLEDPAGTVSSQIPPNWHIPSIQDVAPHHAPAAPSNPGLII
GALAGSTLAVLVIGGIAFWVRRRAQMAPKRLRLPHIRDDDAPPSHQPLF
Y.

In another embodiment, the HSV-2 gD encoded by modified mRNA utilized in the methods and compositions of the present invention comprises the amino acid sequences as set forth in GenBank Accession Numbers: 1003204A, AAA45841.1, AAA45842.1, AAB60552.1, AAB60553.1, AAB60554.1, AAB60555.1, AAB72102.1, AAS01730.1, AAW23130.1, AAW23131.1, AAW23132.1, AAW23133.1, AAW23134.1, ABS84899.1, ABU45433.1, ABU45434.1, ABU45435.1, ABU45461.1, ABU45462.1, ACA28831.1, AEV91405.1, AFM93876.1, AFS18198.1, AFS18199.1, AFS18200.1, AFS18201.1, AFS18202.1, AFS18203.1, AFS18204.1, AFS18205.1, AFS18206.1, AFS18207.1, AFS18208.1, AFS18209.1, AFS18210.1, AFS18211.1, AFS18212.1, AFS18213.1, AFS18214.1, AFS18215.1, AFS18216.1, AFS18217.1, AFS18218.1, AFS18219.1, AFS18220.1, AFS18221.1, AHG54730.1, AIL27720.1, AIL27721.1, AIL27722.1, AIL27723.1, AIL27724.1, AIL27725.1, AIL27726.1, AIL27727.1, AIL27728.1, AIL27729.1, AIL27730.1, AIL27731.1, AIL28069.1, AIL28070.1, AKC42828.1, AKC59305.1, AKC59376.1, AKC59447.1, AKC59518.1, AKC59589.1, AMB66102.1, AMB66171.1, AMB66244.1, AMB66321.1, AMB66394.1, AMB66463.1, AQZ55754.1, AQZ55825.1, AQZ55896.1, AQZ55967.1, AQZ56038.1, AQZ56109.1, AQZ56180.1, AQZ56251.1, AQZ56322.1, AQZ56393.1, AQZ56464.1, AQZ56535.1, AQZ56606.1, AQZ56677.1, AQZ56748.1, AQZ56819.1, AQZ56890.1, AQZ56961.1, AQZ57032.1, AQZ57103.1, AQZ57174.1, AQZ57245.1, AQZ57316.1, AQZ57387.1, AQZ57458.1, AQZ57529.1, AQZ57600.1, AQZ57671.1, AQZ57742.1, AQZ57813.1, AQZ57884.1, AQZ57955.1, AQZ58026.1, AQZ58097.1, AQZ58168.1, AQZ58239.1, AQZ58310.1, AQZ58381.1, AQZ58452.1, AQZ58523.1, AQZ58594.1, AQZ58665.1, AQZ58736.1, AQZ58807.1, AQZ58878.1, AQZ58949.1, AQZ59020.1, AQZ59091.1, AQZ59162.1, ARO38000.1, ARO38001.1, ARO38002.1, ARO38003.1, ARO38004.1, ARO38005.1, ARO38006.1, ARO38007.1, ARO38008.1, ARO38009.1, ARO38010.1, ARO38011.1, ARO38012.1, ARO38013.1, ARO38014.1, ARO38015.1, ARO38016.1, ARO38017.1, ARO38018.1, ARO38019.1, ARO38020.1, ARO38021.1, ARO38022.1, ARO38023.1, ARO38024.1, ARO38025.1, ARO38026.1, ARO38027.1, ARO38028.1, ARO38029.1, ARO38030.1, ARO38031.1, ARO38032.1, ARO38033.1, ARO38034.1, ARO38035.1, ARO38036.1, ARO38037.1, ARO38038.1, ARO38039.1, ARO38040.1, ARO38041.1, ARO38042.1, ARO38043.1, ARO38044.1, CAA26025.1, CAB06713.1, CAC33573.1, CAT05432.1, P03172.2, Q69467.1, or YP_009137218.1.

In another embodiment, the gD protein or fragment includes Y63. In another embodiment, the gD protein or fragment includes R159. In another embodiment, the gD protein or fragment includes D240. In another embodiment, the gD protein or fragment includes P246. In another embodiment, the gD protein or fragment includes a residue selected from Y63, R159, D240, and P246. In another embodiment, inclusion of one of these residues elicits antibodies that inhibit binding to nectin-1.

The nomenclature used herein for gD amino acid residues includes the residues of the signal sequence. Thus, residue one of the mature protein is referred to as "26."

Each modified mRNA encoding gD-1 and gD-2 protein or fragment thereof represents a separate embodiment of the present invention.

In another embodiment, the HSV gD, gC, and gE proteins, and fragments thereof, encoded by the modified mRNA as disclosed herein are described in US Patent Publication No. 2013-0028925-A1, which is incorporated by reference herein in its entirety.

In another embodiment, a gD protein fragment encoded by modified mRNA utilized in the methods and compositions of the present invention is an immunogenic fragment. In another embodiment, a gD immunoprotective antigen need not be the entire protein. The protective immune response generally involves, in another embodiment, an antibody response. In another embodiment, mutants, sequence conservative variants, and functional conservative variants of gD are useful in methods and compositions of the present invention, provided that all such variants retain the required immuno-protective effect. In another embodiment, the immunogenic fragment can comprise an immuno-protective gD antigen from any strain of HSV. In another embodiment, the immunogenic fragment can comprise sequence variants of HSV, as found in infected individuals.

Glycoprotein C

In another embodiment, a composition of the present invention comprises a modified mRNA encoding HSV-1 gC protein. In another embodiment, the composition comprises a modified mRNA encoding a fragment of an HSV-1 gC protein.

In one embodiment, the nucleotide sequence of the modified mRNA encoding an HSV-1 gC fragment comprises:

(SEQ ID NO: 7)

GGAAUAAAAGUCUCAACACAACAUAUACAAAACAAACGAAUCUCAAGCA

AUCAAGCAUUCUACUUCUAUUGCAGCAAUUUAAAUCAUUUCUUUUAAAG

CAAAAGCAAUUUUCUGAAAAUUUUCACCAUUUACGAACGAUAGCAUGGC

CAUCUCCGGCGUGCCCGUGCUGGGCUUCUUCAUCAUCGCCGUGCUGAUG

UCCGCCCAGGAGUCCUGGGCCGAGACCGCCUCCACCGGCCCCACCAUCA

CCGCCGGCGCCGUGACCAACGCCUCCGAGGCCCCCACCUCCGGCUCCCC

CGGCUCCGCCGCCUCCCCCGAGGUGACCCCCACCUCCACCCCCAACCCC

AACAACGUGACCCAGAACAAGACCACCCCCACCGAGCCCGCCUCCCCCC

CCACCACCCCCAAGCCCACCUCCACCCCCAAGUCCCCCCCCACCUCCAC

CCCCGACCCCAAGCCCAAGAACAACACCACCCCCGCCAAGUCCGGCCGC

CCCACCAAGCCCCCCGGCCCCGUGUGGUGCGACCGCCGCGACCCCCUGG

CCCGCUACGGCUCCCGCGUGCAGAUCCGCUGCCGCUUCCGCAACUCCAC

CCGCAUGGAGUUCCGCCUGCAGAUCUGGCGCUACUCCAUGGGCCCCUCC

CCCCCCAUCGCCCCCGCCCCCGACCUGGAGGAGGUGCUGACCAACAUCA

CCGCCCCCCCCGGCGGCCUGCUGGUGUACGACUCCGCCCCCAACCUGAC

CGACCCCCACGUGCUGUGGGCCGAGGGCGCCGGCCCCGGCGCCGACCCC

CCCCUGUACUCCGUGACCGGCCCCCUGCCCACCCAGCGCCUGAUCAUCG

GCGAGGUGACCCCCGCCACCCAGGGCAUGUACUACCUGGCCUGGGGCCG

CAUGGACUCCCCCCACGAGUACGGCACCUGGGUGCGCGUGCGCAUGUUC

CGCCCCCCCUCCCUGACCCUGCAGCCCCACGCCGUGAUGGAGGGCCAGC

CCUUCAAGGCCACCUGCACCGCCGCCGCCUACUACCCCCGCAACCCCGU

GGAGUUCGACUGGUUCGAGGACGACCGCCAGGUGUUCAACCCCGGCCAG

AUCGACACCCAGACCCACGAGCACCCCGACGGCUUCACCACCGUGUCCA

CCGUGACCUCCGAGGCCGUGGGCGGCCAGGUGCCCCCCCGCACCUUCAC

CUGCCAGAUGACCUGGCACCGCGACUCCGUGACCUUCUCCCGCCGCAAC

GCCACCGGCCUGGCCCUGGUGCUGCCCCGCCCCACCAUCACCAUGGAGU

-continued

UCGGCGUGCGCCACGUGGUGUGCACCGCCGGCUGCGUGCCCGAGGGCGU

GACCUUCGCCUGGUUCCUGGGCGACGACCCCUCCCCCGCCGCCAAGUCC

GCCGUGACCGCCCAGGAGUCCUGCGACCACCCCGGCCUGGCCACCGUGC

GCUCCACCCUGCCCAUCUCCUACGACUACUCCGAGUACAUCUGCCGCCU

GACCGGCUACCCCGCCGGCAUCCCCGUGCUGGAGCACCACUAA*CUAGUA*

*GUGACUGACUAGGAUCUGGUUACCACUAAACCAGCCUCAAGAACACCCG*

*AAUGGAGUCUCUAAGCUACAUAAUACCAACUUACACUUACAAAAUGUUG*

*UCCCCCAAAAUGUAGCCAUUCGUAUCUGCUCCUAAUAAAAAGAAAGUUU*

*CUUCACAUUCUAAAAAAAAAAAAAAAAAAAAAAAAAAAAAAAAAAAAAAA*

*AAAAAAAAAAAAAAAAAAAAAAAAAAAAAAAAAAAAAAAAAAAAAAAAAA*

*AAAAAAAAAAAAAAAC*

In one embodiment, all uridine residues are 1-methyl-pseudouridine. In one embodiment, underlined residues represent 5' untranslated sequences. In one embodiment, bold residues represent a signal sequence (leader sequence) to assist expression of the gC1 fragment. In one embodiment, italicized residues represent 3' untranslated sequences and poly adenylation tail.

In another embodiment, the nucleotide sequence of the modified mRNA encoding an HSV-1 gC fragment does not comprise the 5' untranslated sequences, the signal sequence, the 3' untranslated sequences, the poly adenylation tail, or a combination thereof.

In one embodiment, the HSV-1 gC fragment encoded by modified mRNA utilized in the methods and compositions of the present invention comprises amino acids 27-457 of gC from HSV-1 KOS strain, as set forth in the following amino acid sequence:

(SEQ ID NO: 8)

ETASTGPTITAGAVTNASEAPTSGSPGSAASPEVTPTSTPNPNNVTQNK

TTPTEPASPPTTPKPTSTPKSPPTSTPDPKPKNNTTPAKSGRPTKPPGP

VWCDRRDPLARYGSRVQIRCRFRNSTRMEFRLQIWRYSMGPSPPIAPAP

DLEEVLTNITAPPGGLLVYDSAPNLTDPHVLWAEGAGPGADPPLYSVTG

PLPTQRLIIGEVTPATQGMYYLAWGRMDSPHEYGTWVRVRMFRPPSLTL

QPHAVMEGQPFKATCTAAAYYPRNPVEFDWFEDDRQVENPGQIDTQTHE

HPDGFTTVSTVTSEAVGGQVPPRTFTCQMTWHRDSVTFSRRNATGLALV

LPRPTITMEFGVRHVVCTAGCVPEGVTFAWFLGDDPSPAAKSAVTAQES

CDHPGLATVRSTLPISYDYSEYICRLTGYPAGIPVLEHH.

In one embodiment, the gC fragment encoded by modified mRNA utilized in the methods and compositions of the present invention comprises amino acids 27-457 of gC from an HSV-1 strain.

In one embodiment, the full length HSV-1 gC encoded by modified mRNA utilized in the methods and compositions of the present invention comprises the following amino acid sequence:

(SEQ ID NO: 9)

MAPGRVGLAVVLWGLLWLGAGVAGGSETASTGPTITAGAVTNASEAPTS

GSPGSAASPEVTPTSTPNPNNVTQNKTTPTEPASPPTTPKPTSTPKSPP

-continued

TSTPDPKPKNNTTPAKSGRPTKPPGPVWCDRRDPLARYGSRVQIRCRFR

NSTRMEFRLQIWRYSMGPSPPIAPAPDLEEVLTNITAPPGGLLVYDSAP

NLTDPHVLWAEGAGPGADPPLYSVTGPLPTQRLIIGEVTPATQGMYYLA

WGRMDSPHEYGTWVRVRMFRPPSLTLQPHAVMEGQPFKATCTAAAYYPR

NPVEFDWFEDDRQVFNPGQIDTQTHEHPDGFTTVSTVTSEAVGGQVPPR

TFTCQMTWHRDSVTFSRRNATGLALVLPRPTITMEFGVRHVVCTAGCVP

EGVTFAWFLGDDPSPAAKSAVTAQESCDHPGLATVRSTLPISYDYSEYI

CRLTGYPAGIPVLEHHGSHQPPPRDPTERQVIEAIEWVGIGIGVLAAGV

LVVTAIVYVVRTSQSRQRHRR.

In another embodiment, the HSV-1 gC encoded by modified mRNA utilized in the methods and compositions of the present invention comprises the amino acid sequences as set forth in any of the following GenBank Accession Numbers: AAA45779.1, AAA96680.1, ABI63505.1, ABM52973.1, ABM52976.1, ABM52977.1, ACM62267.1, ADD60042.1, ADD60119.1, ADM22367.1, ADM22444.1, ADM22520.1, ADM22597.1, ADM22674.1, ADM22751.1, ADM22827.1, ADM22904.1, ADM22981.1, ADM23057.1, ADM23133.1, ADM23210.1, ADM23287.1, ADM23361.1, ADM23435.1, ADM23509.1, ADM23583.1, ADM23658.1, ADM23733.1, ADM23809.1, AEQ77075.1, AEQ77099.1, AER37628.1, AER37697.1, AER37767.1, AER37838.1, AER37910.1, AER37981.1, AER38051.2, AFA36179.1, AFA36180.1, AFA36181.1, AFA36182.1, AFA36183.1, AFA36184.1, AFA36185.1, AFA36186.1, AFA36187.1, AFA36188.1, AFA36189.1, AFA36190.1, AFA36191.1, AFA36192.1, AFA36193.1, AFA36194.1, AFA36195.1, AFA36196.1, AFA36197.1, AFA36198.1, AFA36199.1, AFA36200.1, AFA36201.1, AFA36202.1, AFA36203.1, AFE62872.1, AFH78104.1, AFI23635.1, AFK50391.1, AFP86408.1, AGZ01906.1, AIR95840.1, AJE59989.1, AJE60060.1, AJE60131.1, AJE60202.1, AKE48623.1, AKE98415.1, AKE98416.1, AKE98417.1, AKE98418.1, AKE98419.1, AKE98420.1, AKE98421.1, AKE98422.1, AKE98423.1, AKE98424.1, AKE98425.1, AKE98426.1, AKE98427.1, AKE98428.1, AKE98429.1, AKE98430.1, AKE98431.1, AKE98432.1, AKE98433.1, AKE98434.1, AKE98435.1, AKG59227.1, AKG59299.1, AKG59372.1, AKG59444.1, AKG59516.1, AKG59591.1, AKG59663.1, AKG59736.1, AKG59807.1, AKG59879.1, AKG59953.1, AKG60027.1, AKG60099.1, AKG60170.1, AKG60243.1, AKG60316.1, AKG60386.1, AKG60456.1, AKG60528.1, AKG60601.1, AKG60674.1, AKG60745.1, AKG60817.1, AKG60887.1, AKG60959.1, AKG61032.1, AKG61104.1, AKG61175.1, AKG61248.1, AKG61321.1, AKG61392.1, AKG61464.1, AKG61537.1, AKG61611.1, AKG61684.1, AKG61756.1, AKG61828.1, AKG61902.1, AKG61974.1, AKH80444.1, AKH80517.1, AKM76368.1, ALM22613.1, ALM22687.1, ALM22761.1, ALM22835.1, ALO18641.1, ALO18717.1, AMB65642.1, AMB65715.1, AMB65862.1, AMN09813.1, ANN83942.1, ANN84019.1, ANN84095.1, ANN84172.1, ANN84249.1, ANN84326.1, ANN84403.1, ANN84478.1, ANN84555.1, ANN84632.1, ANN84708.1, ANN84785.1, ANN84861.1, ANN84938.1, ANN85014.1, ANN85091.1, ANN85167.1, ANN85242.1, ANN85319.1, ANN85396.1, ANN85472.1, ANN85549.1, ANN85626.1, ANN85703.1, ANN85779.1, AOY34308.1, AOY36663.1, AOY36687.1, ARB08935.1, ARO38059.1, ARO38060.1, ARO38061.1, ARO38062.1, ARO38063.1, ARO38064.1, ARO38065.1, ARO38066.1, ASM47642.1, ASM47719.1, ASM47796.1, ASM47871.1, BAM73394.1, CAA32294.1, CAB40083.1, CAD13356.1, CAD13357.1, CAD13358.1, CAD13359.1, CAD13360.1, CAD13361.1, CAD13362.1, CAD13363.1, CAD13364.1, CAD13365.1, CAD13366.1, CAD13367.1, CAD13368.1, CAD13369.1, CAD13370.1, CAD13371.1, CAD13372.1, CAD13373.1, CAD13374.1, CAD13375.1, CAD13376.1, CAD13377.1, CAD13378.1, P04290.1, P04488.1, P09855.1, P10228.1, P28986.1, SBO07729.1, SBO07793.1, SBO07798.1, SBO07812.1, SBO07880.1, SBS69375.1, SBS69379.1, SBS69440.1, SBS69448.1, SBS69560.1, SBS69599.1, SBS69602.1, SBS69637.1, SBS69790.1, SBT69374.1, SCL76887.1, YP_009137119.1, or YP_009137143.1.

In another embodiment, the composition comprises a modified mRNA encoding an HSV-2 gC protein. In another embodiment, the composition comprises a modified mRNA encoding a fragment of an HSV-2 gC protein.

In one embodiment, the nucleotide sequence of the modified mRNA encoding an HSV-2 gC fragment comprises:

(SEQ ID NO: 10)

GGAAUAAAAGUCUCAACACAACAUAUACAAAACAAACGAAUCUCAAGCA

AUCAAGCAUUCUACUUCUAUUGCAGCAAUUUAAAUCAUUUCUUUUAAAG

CAAAAGCAAUUUUCUGAAAAUUUUCACCAUUUACGAACGAUAGCAUGCG

CAUGCAGCUGCUGCUGCUGAUCGCCCUGUCCCUGGCCCUGGUGACCAAC

UCCGCCUCCCCCGGCCGCACCAUCACCGUGGGCCCCCGCGGCAACGCCU

CCAACGCCGCCCCCUCCGCCUCCCCCCGCAACGCCUCCGCCCCCCGCAC

CACCCCCACCCCCCCCCAGCCCCGCAAGGCCACCAAGUCCAAGGCCUCC

ACCGCCAAGCCCGCCCCCCCCCCCAAGACCGGCCCCCCCAAGACCUCCU

CCGAGCCCGUGCGCUGCAACCGCCACGACCCCCUGGCCCGCUACGGCUC

CCGCGUGCAGAUCCGCUGCCGCUUCCCCAACUCCACCCGCACCGAGUUC

CGCCUGCAGAUCUGGCGCUACGCCACCGCCACCGACGCCGAGAUCGGCA

CCGCCCCCUCCCUGGAGGAGGUGAUGGUGAACGUGUCCGCCCCCCCCGG

CGGCCAGCUGGUGUACGACUCCGCCCCCAACCGCACCGACCCCCACGUG

AUCUGGGCCGAGGGCGCCGGCCCCGGCGCCUCCCCCCGCCUGUACUCCG

UGGUGGGCCCCCUGGGCCGCCAGCGCCUGAUCAUCGAGGAGCUGACCCU

GGAGACCCAGGGCAUGUACUACUGGGUGUGGGGCCGCACCGACCGCCCC

UCCGCCUACGGCACCUGGGUGCGCGUGCGCGUGUUCCGCCCCCCCUCCC

UGACCAUCCACCCCCACGCCGUGCUGGAGGGCCAGCCCUUCAAGGCCAC

CUGCACCGCCGCCACCUACUACCCCGGCAACCGCGCCGAGUUCGUGUGG

UUCGAGGACGGCCGCCGCGUGUUCGACCCCGCCCAGAUCCACACCCAGA

CCCAGGAGAACCCCGACGGCUUCUCCACCGUGUCCACCGUGACCUCCGC

CGCCGUGGGCGGCCAGGGCCCCCCCCGCACCUUCACCUGCCAGCUGACC

UGGCACCGCGACUCCGUGUCCUUCUCCCGCCGCAACGCCUCCGGCACCG

CCUCCGUGCUGCCCCGCCCCACCAUCACCAUGGAGUUCACCGGCGACCA

CGCCGUGUGCACCGCCGGCUGCGUGCCCGAGGGCGUGACCUUCGCCUGG

UUCCUGGGCGACGACUCCUCCCCCGCCGAGAAGGUGGCCGUGGCCUCCC

AGACCUCCUGCGGCCGCCCCGGCACCGCCACCAUCCGCUCCACCCUGCC

-continued

CGUGUCCUACGAGCAGACCGAGUACAUCUGCCGCCUGGCCGGCUACCCC

GACGGCAUCCCCGUGCUGGAGCACCACUAA*CUAGUAGUGACUGACUAGG*

*AUCUGGUUACCACUAAACCAGCCUCAAGAACACCCGAAUGGAGUCUCUA*

*AGCUACAUAAUACCAACUUACACUUACAAAAUGUUGUCCCCCAAAAUGU*

*AGCCAUUCGUAUCUGCUCCUAAUAAAAAGAAAGUUUCUUCACAUUCUAA*

*AAAAAAAAAAAAAAAAAAAAAAAAAAAAAAAAAAAAAAAAAAAAAAAAAA*

*AAAAAAAAAAAAAAAAAAAAAAAAAAAAAAAAAAAAAAAAAAAAAAAAAA*

*AC*.

In one embodiment, all uridine residues are 1-methyl-pseudouridine. In one embodiment, underlined residues represent 5' untranslated sequences. In one embodiment, bold residues represent a signal sequence (leader sequence) to assist expression of the gC2 fragment. In one embodiment, italicized residues represent 3' untranslated sequences and poly adenylation tail.

In another embodiment, the nucleotide sequence of the modified mRNA encoding an HSV-2 gC fragment lacks the 5' untranslated sequences, the signal sequence, the 3' untranslated sequences, the poly adenylation tail, or a combination thereof.

In one embodiment, the HSV-2 gC fragment encoded by modified mRNA utilized in the methods and compositions of the present invention comprises amino acids 27-426 of gC from HSV-2 strain 333, as set forth in the following amino acid sequence:

(SEQ ID NO: 11)

ASPGRTITVGPRGNASNAAPSASPRNASAPRTTPTPPQPRKATKSKAST

AKPAPPPKTGPPKTSSEPVRCNRHDPLARYGSRVQIRCRFPNSTRTESR

LQIWRYATATDAEIGTAPSLEEVMVNVSAPPGGQLVYDSAPNRTDPHVI

WAEGAGPGASPRLYSVVGPLGRQRLIIEELTLETQGMYYWVWGRTDRPS

AYGTWVRVRVFRPPSLTIHPHAVLEGQPFKATCTAATYYPGNRAEFVWF

EDGRRVFDPAQIHTQTQENPDGFSTVSTVTSAAVGGQGPPRTFTCQLTW

HRDSVSFSRRNASGTASVLPRPTITMEFTGDHAVCTAGCVPEGVTFAWF

LGDDSSPAEKVAVASQTSCGRPGTATIRSTLPVSYEQTEYICRLAGYPD

GIPVLEHH.

In one embodiment, the full length HSV-2 gC encoded by modified mRNA utilized in the methods and compositions of the present invention comprises the following amino acid sequence:

(SEQ ID NO: 12)

MALGRVGLAVGLWGLLWVGVVVVLANASPGRTITVGPRGNASNAAPSAS

PRNASAPRTTPTPPQPRKATKSKASTAKPAPPPKTGPPKTSSEPVRCNR

HDPLARYGSRVQIRCRFPNSTRTEFRLQIWRYATATDAEIGTAPSLEEV

MVNVSAPPGGQLVYDSAPNRTDPHVIWAEGAGPGASPRLYSVVGPLGRQ

RLIIEELTLETQGMYYWVWGRTDRPSAYGTWVRVRVFRPPSLTIHPHAV

LEGQPFKATCTAATYYPGNRAEFVWFEDGRRVFDPAQIHTQTQENPDGF

STVSTVTSAAVGGQGPPRTFTCQLTWHRDSVSFSRRNASGTASVLPRPT

-continued

ITMEFTGDHAVCTAGCVPEGVTFAWFLGDDSSPAEKVAVASQTSCGRPG

TATIRSTLPVSYEQTEYICRLAGYPDGIPVLEHHGSHQPPPRDPTERQV

IRAVEGAGIGVAVLVAVVLAGTAVVYLTHASSVRYRRLR.

In another embodiment, the HSV-2 gC encoded by modified mRNA utilized in the methods and compositions of the present invention comprises the amino acid sequences as set forth in any of the following GenBank Accession Numbers: AAA20532.1, AAA66442.1, AAB60549.1, AAB60550.1, AAB60551.1, AAB72101.1, ABU45429.1, ABU45430.1, ABU45431.1, ABU45432.1, ABU45459.1, ABU45460.1, AEV91348.1, AEV91383.1, AEV91407.1, AFM93864.1, AHG54708.1, AKC42808.1, AKC59285.1, AKC59357.1, AKC59428.1, AKC59499.1, AKC59570.1, AMB66008.1, AMB66079.1, AMB66151.1, AMB66224.1, AMB66252.1, AMB66253.1, AMB66368.1, AMB66441.1, AQZ55735.2, AQZ55806.1, AQZ55877.1, AQZ55948.1, AQZ56019.1, AQZ56090.1, AQZ56161.2, AQZ56232.2, AQZ56303.2, AQZ56374.2, AQZ56445.1, AQZ56516.1, AQZ56587.1, AQZ56658.1, AQZ56729.2, AQZ56800.1, AQZ56871.1, AQZ56942.2, AQZ57013.1, AQZ57084.2, AQZ57155.1, AQZ57226.1, AQZ57297.1, AQZ57368.1, AQZ57439.1, AQZ57510.1, AQZ57581.1, AQZ57652.1, AQZ57723.1, AQZ57794.2, AQZ57865.2, AQZ57936.1, AQZ58007.2, AQZ58078.1, AQZ58149.2, AQZ58220.1, AQZ58291.1, AQZ58362.1, AQZ58433.1, AQZ58504.1, AQZ58575.1, AQZ58646.1, AQZ58717.2, AQZ58788.2, AQZ58859.2, AQZ58930.1, AQZ59001.2, AQZ59072.1, AQZ59143.1, ARO38067.1, ARO38068.1, ARO38069.1, ARO38070.1, ARO38071.1, ARO38072.1, CAA25687.1, CAA26025.1, CAB06730.1, CAB06734.1, CAB96544.1, P03173.1, P06475.1, P89475.1, Q89730.1, YP_009137161.1, YP_009137196.1, or YP_009137220.1.

In another embodiment, the gC protein fragment encoded by modified mRNA utilized in the methods and compositions of the present invention comprises a properdin interfering domain "Properdin-interfering domain" refers, in one embodiment, to a domain that blocks or inhibits binding of a host C3b molecule with a host properdin molecule. In another embodiment, the term refers to a domain that blocks or inhibits an interaction of a host C3b molecule with a host properdin molecule.

In another embodiment, the gC protein fragment encoded by modified mRNA utilized in the methods and compositions of the present invention is a C5 interfering domain. In another embodiment, the gC protein fragment is a portion of a C5 interfering domain. "C5-interfering domain" refers, in another embodiment, to a domain that interferes with binding of a host C3b molecule with a host C5 molecule. In another embodiment, the term refers to a domain that interferes with the interaction of a host C3b molecule with a host C5 molecule.

Each modified mRNA encoding gC-1 or gC-2 protein or fragment thereof represents a separate embodiment of the present invention.

In another embodiment, a gC protein fragment encoded by modified mRNA utilized in the methods and compositions of the present invention is an immunogenic fragment. In another embodiment, a gC immunoprotective antigen need not be the entire protein. The protective immune response generally involves, in another embodiment, an antibody response. In another embodiment, mutants, sequence conservative variants, and functional conservative variants of gC are useful in methods and compositions of the present invention, provided that all such variants retain the required immuno-protective effect. In another embodiment, the immunogenic fragment can comprise an immuno-protective gC antigen from any strain of HSV. In another embodiment, the immunogenic fragment can comprise sequence variants of HSV, as found in infected individuals.

Glycoprotein E

In another embodiment, a composition of the present invention comprises a modified mRNA encoding HSV-1 gE protein. In another embodiment, the composition comprises a modified mRNA encoding a fragment of an HSV-1 gE protein.

In one embodiment, the nucleotide sequence of the modified mRNA encoding an HSV-1 gD fragment comprises:

(SEQ ID NO: 13)

GGAAUAAAAGUCUCAACACAACAUAUACAAAACAAACGAAUCUCAAGCA

AUCAAGCAUUCUACUUCUAUUGCAGCAAUUUAAAUCAUUUCUUUUAAAG

CAAAAGCAAUUUUCUGAAAAUUUUCACCAUUUACGAACGAUAGCAUGCG

CAUGCAGCUGCUGCUGCUGAUCGCCCUGUCCCUGGCCCUGGUGACCAAC

UCCAAGACCUCCUGGCGCCGCGUGUCCGUGGGCGAGGACGUGUCCCUGC

UGCCCGCCCCCGGCCCCACCGGCCGCGGCCCCACCCAGAAGCUGCUGUG

GGCCGUGGAGCCCCUGGACGGCUGCGGCCCCCUGCACCCCUCCUGGGUG

UCCCUGAUGCCCCCCAAGCAGGUGCCCGAGACCGUGGUGGACGCCGCCU

GCAUGCGCGCCCCCGUGCCCCUGGCCAUGGCCUACGCCCCCCCCGCCCC

CUCCGCCACCGGCGGCCUGCGCACCGACUUCGUGUGGCAGGAGCGCGCC

GCCGUGGUGAACCGCUCCCUGGUGAUCUACGGCGUGCGCGAGACCGACU

CCGGCCUGUACACCCUGUCCGUGGGCGACAUCAAGGACCCCGCCCGCCA

GGUGGCCUCCGUGGUGCUGGUGGUGCAGCCCGCCCCCGUGCCCACCCCC

CCCCCCACCCCCGCCGACUACGACGAGGACGACAACGACGAGGGCGAGG

GCGAGGACGAGUCCCUGGCCGGCACCCCCGCCUCCGGCACCCCCCGCCU

GCCCCCCUCCCCCGCCCCCCCCCGCUCCUGGCCCUCCGCCCCCGAGGUG

UCCCACGUGCGCGGCGUGACCGUGCGCAUGGAGACCCCCGAGGCCAUCC

UGUUCUCCCCCGGCGAGGCCUUCUCCACCAACGUGUCCAUCCACGCCAU

CGCCCACGACGACCAGACCUACACCAUGGACGUGGUGUGGCUGCGCUUC

GACGUGCCCACCUCCUGCGCCGAGAUGCGCAUCUACGAGUCCUGCCUGU

ACCACCCCCAGCUGCCCGAGUGCCUGUCCCCCGCCGACGCCCCCUGCGC

CGCCUCCACCUGGACCUCCCGCCUGGCCGUGCGCUCCUACGCCGGCUGC

UCCCGCACCAACCCCCCCCCCCGCUGCUCCGCCGAGGCCCACAUGGAGC

CCUUCCCCGGCCUGGCCUGGCAGGCCGCCUCCGUGAACCUGGAGUUCCG

CGACGCCUCCCCCCAGCACUCCGGCCUGUACCUGUGCGUGGUGUACGUG

AACGACCACAUCCACGCCUGGGGCCACAUCACCAUCAACACCGCCGCCC

AGUACCGCAACGCCGUGGUGGAGCAGCCCCUGCCCCAGCGCGGCGCCGA

CCUGGCCGAGCCCACCCACCCCCACGUGGGCGCCUAA*CUAGUAGUGACU*

*GACUAGGAUCUGGUUACCACUAAACCAGCCUCAAGAACACCCGAAUGGA*

*GUCUCUAAGCUACAUAAUACCAACUUACACUUACAAAAUGUUGUCCCCC*

*AAAAUGUAGCCAUUCGUAUCUGCUCCUAAUAAAAAGAAAGUUUCUUCAC*

-continued

*AUUCUAAAAAAAAAAAAAAAAAAAAAAAAAAAAAAAAAAAAAAAAAAAAA*

*AAAAAAAAAAAAAAAAAAAAAAAAAAAAAAAAAAAAAAAAAAAAAAAAAA*

*AAAAAAAAC*.

In one embodiment, all uridine residues are 1-methyl-pseudouridine. In one embodiment, underlined residues represent 5' untranslated sequences. In one embodiment, bold residues represent a signal sequence (leader sequence) to assist expression of the gE1 fragment. In one embodiment, italicized residues represent 3' untranslated sequences and poly adenylation tail.

In another embodiment, the nucleotide sequence of the modified mRNA encoding an HSV-1 gE fragment lacks the 5' untranslated sequences, the signal sequence, the 3' untranslated sequences, the poly adenylation tail, or a combination thereof.

In one embodiment, the HSV-1 gE fragment encoded by modified mRNA utilized in the methods and compositions of the present invention comprises amino acids 24-409 of gE from HSV-1 NS strain, as set forth in the following amino acid sequence:

(SEQ ID NO: 14)

KTSWRRVSVGEDVSLLPAPGPTGRGPTQKLLWAVEPLDGCGPLHPSWVS

LMPPKQVPETVVDAACMRAPVPLAMAYAPPAPSATGGLRTDFVWQERAA

VVNRSLVIYGVRETDSGLYTLSVGDIKDPARQVASVVLVVQPAPVPTPP

PTPADYDEDDNDEGEGEDESLAGTPASGTPRLPPSPAPPRSWPSAPEVS

HVRGVTVRMETPEAILFSPGEAFSTNVSIHAIAHDDQTYTMDVVWLRFD

VPTSCAEMRIYESCLYHPQLPECLSPADAPCAASTWTSRLAVRSYAGCS

RTNPPPRCSAEAHMEPFPGLAWQAASVNLEFRDASPQHSGLYLCVVYVN

DHIHAWGHITINTAAQYRNAVVEQPLPQRGADLAEPTHPHVGA.

In one embodiment, the gE fragment encoded by modified mRNA utilized in the methods and compositions of the present invention comprises amino acids 24-409 of gE from an HSV-1 strain.

In one embodiment, the full length HSV-1 gE encoded by modified mRNA utilized in the methods and compositions of the present invention comprises the following amino acid sequence:

(SEQ ID NO: 15)

MDRGAVVGFLLGVCVVSCLAGTPKTSWRRVSVGEDVSLLPAPGPTGRGP

TQKLLWAVEPLDGCGPLHPSWVSLMPPKQVPETVVDAACMRAPVPLAMA

YAPPAPSATGGLRTDFVWQERAAVVNRSLVIYGVRETDSGLYTLSVGDI

KDPARQVASVVLVVQPAPVPTPPPTPADYDEDDNDEGEGEDESLAGTPA

SGTPRLPPSPAPPRSWPSAPEVSHVRGVTVRMETPEAILFSPGEAFSTN

VSIHAIAHDDQTYTMDVVWLRFDVPTSCAEMRIYESCLYHPQLPECLSP

ADAPCAASTWTSRLAVRSYAGCSRTNPPPRCSAEAHMEPFPGLAWQAAS

VNLEFRDASPQHSGLYLCVVYVNDHIHAWGHITINTAAQYRNAVVEQPL

PQRGADLAEPTHPHVGAPPHAPPTHGALRLGAVMGAALLLSALGLSVWA

CMTCWRRRAWRAVKSRASGKGPTYIRVADSELYADWSSDSEGERDQVPW

-continued

LAPPERPDSPSTNGSGFEILSPTAPSVYPRSDGHQSRRQLTTFGSGRPD

RRYSQASDSSVFW.

In another embodiment, the HSV-1 gE encoded by modified mRNA utilized in the methods and compositions of the present invention comprises the amino acid sequences as set forth in any of the following GenBank Accession Numbers: AAA45779.1, AAA96680.1, ABI63526.1, ACM62297.1, ADD60055.1, ADD60132.1, ADM22391.1, ADM22468.1, ADM22544.1, ADM22621.1, ADM22698.1, ADM22775.1, ADM22851.1, ADM22928.1, ADM23005.1, ADM23081.1, ADM23157.1, ADM23233.1, ADM23311.1, ADM23385.1, ADM23459.1, ADM23533.1, ADM23607.1, ADM23682.1, ADM23757.1, ADM23833.1, ADN34689.1, ADN34692.1, ADN34695.1, AEQ77099.1, AER37649.1, AER37717.1, AER37788.1, AER37859.1, AER37931.1, AER38002.1, AER38072.1, AFA36179.1, AFA36180.1, AFA36181.1, AFA36182.1, AFA36183.1, AFA36184.1, AFA36185.1, AFA36186.1, AFA36187.1, AFA36188.1, AFA36189.1, AFA36190.1, AFA36191.1, AFA36192.1, AFA36193.1, AFA36194.1, AFA36195.1, AFA36196.1, AFA36197.1, AFA36198.1, AFA36199.1, AFA36200.1, AFA36201.1, AFA36202.1, AFA36203.1, AFE62896.1, AFI23659.1, AFK50417.1, AFP86432.1, AGZ01930.1, AIR95859.1, AJE60011.1, AJE60082.1, AJE60153.1, AJE60224.1, AJE60295.1, AKE48647.1, AKE98373.1, AKE98374.1, AKE98375.1, AKE98376.1, AKE98377.1, AKE98378.1, AKE98379.1, AKE98380.1, AKE98381.1, AKE98382.1, AKE98383.1, AKE98384.1, AKE98385.1, AKE98386.1, AKE98387.1, AKE98388.1, AKE98389.1, AKE98390.1, AKE98391.1, AKE98392.1, AKE98393.1, AKG59248.1, AKG59320.1, AKG59393.1, AKG59464.1, AKG59538.1, AKG59611.1, AKG59684.1, AKG59757.1, AKG59828.1, AKG59900.1, AKG59974.1, AKG60048.1, AKG60120.1, AKG60191.1, AKG60263.1, AKG60336.1, AKG60406.1, AKG60476.1, AKG60548.1, AKG60622.1, AKG60694.1, AKG60765.1, AKG60837.1, AKG60908.1, AKG60980.1, AKG61052.1, AKG61125.1, AKG61196.1, AKG61269.1, AKG61341.1, AKG61413.1, AKG61486.1, AKG61558.1, AKG61631.1, AKG61705.1, AKG61776.1, AKG61849.1, AKG61922.1, AKG61995.1, AKH80465.1, AKH80538.1, ALM22637.1, ALM22711.1, ALM22785.1, ALM22859.1, ALO18664.1, ALO18740.1, AMB65664.1, AMB65737.1, AMB65811.1, AMB65887.1, AMB65958.1, AMN09834.1, ANN83966.1, ANN84043.1, ANN84119.1, ANN84196.1, ANN84273.1, ANN84350.1, ANN84426.1, ANN84502.1, ANN84579.1, ANN84655.1, ANN84732.1, ANN84808.1, ANN84885.1, ANN84961.1, ANN85038.1, ANN85114.1, ANN85189.1, ANN85266.1, ANN85343.1, ANN85418.1, ANN85496.1, ANN85573.1, ANN85650.1, ANN85726.1, ANN85803.1, AOY34085.1, AOY36687.1, ARB08959.1, ARO38073.1, ARO38074.1, ARO38075.1, ARO38076.1, ARO38077.1, ARO38078.1, ARO38079.1, ARO38080.1, ASM47642.1, ASM47666.1, ASM47743.1, ASM47820.1, ASM47895.1, BAM73421.1, CAA26062.1, CAA32272.1, CAF24756.1, CAF24757.1, CAF24758.1, CAF24759.1, CAF24760.1, CAF24761.1, CAF24762.1, CAF24763.1, CAF24764.1, CAF24765.1, CAF24766.1, CAF24767.1, CAF24768.1, CAF24769.1, CAF24770.1, CAF24771.1, CAF24772.1, CAF24773.1, CAF24774.1, CAF24775.1, CAF24776.1, CAF24777.1, CAF24778.1, CAF24779.1, CAF24780.1, CAF24781.1, CAF24782.1, CAF24783.1, CAF24784.1, CAF24785.1, P04290.1, P04488.1, P28986.1, Q703F0.1, SBO07910.1, SBS69571.1, SBS69576.1, SBS69595.1, SBS69636.1, SBS69693.1, SBS69701.1, SBS69722.1, SBS69732.1, SBS69813.1, SBT69397.1, or YP_009137143.1.

In another embodiment, the composition comprises a modified mRNA encoding an HSV-2 gE protein. In another embodiment, the composition comprises a modified mRNA encoding a fragment of an HSV-2 gE protein.

In one embodiment, the nucleotide sequence of the modified mRNA encoding an HSV-2 gE fragment comprises:

(SEQ ID NO: 16)

GGAAUAAAAGUCUCAACACAACAUAUACAAAACAAACGAAUCUCAAGCA
AUCAAGCAUUCUACUUCUAUUGCAGCAAUUUAAAUCAUUUCUUUUAAAG
CAAAAGCAAUUUUCUGAAAAUUUUCACCAUUUACGAACGAUAGCAUGCG
CAUGCAGCUGCUGCUGCUGAUCGCCCUGUCCCUGGCCCUGGUGACCAAC
UCCCGCACCUCCUGGAAGCGCGUGACCUCCGGCGAGGACGUGGUGCUGC
UGCCCGCCCCCGCCGGCCCCGAGGAGCGCACCCGCGCCCACAAGCUGCU
GUGGGCCGCCGAGCCCCUGGACGCCUGCGGCCCCCUGCGCCCCUCCUGG
GUGGCCCUGUGGCCCCCCCGCCGCGUGCUGGAGACCGUGGUGGACGCCG
CCUGCAUGCGCGCCCCCGAGCCCCUGGCCAUCGCCUACUCCCCCCCCUU
CCCCGCCGGCGACGAGGGCCUGUACUCCGAGCUGGCCUGGCGCGACCGC
GUGGCCGUGGUGAACGAGUCCCUGGUGAUCUACGGCGCCCUGGAGACCG
ACUCCGGCCUGUACACCCUGUCCGUGGUGGGCCUGUCCGACGAGGCCCG
CCAGGUGGCCUCCGUGGUGCUGGUGGUGGAGCCCGCCCCCGUGCCCACC
CCCACCCCCGACGACUACGACGAGGAGGACGACGCCGGCGUGUCCGAGC
GCACCCCCGUGUCCGUGCCCCCCCCCACCCCCCCCCGCCGCCCCCCCGU
GGCCCCCCCCACCCACCCCCGCGUGAUCCCCGAGGUGUCCCACGUGCGC
GGCGUGACCGUGCACAUGGAGACCCCCGAGGCCAUCCUGUUCGCCCCCG
GCGAGACCUUCGGCACCAACGUGUCCAUCCACGCCAUCGCCCACGACGA
CGGCCCCUACGCCAUGGACGUGGUGUGGAUGCGCUUCGACGUGCCCUCC
UCCUGCGCCGAGAUGCGCAUCUACGAGGCCUGCCUGUACCACCCCCAGC
UGCCCGAGUGCCUGUCCCCCGCCGACGCCCCCUGCGCCGUGUCCUCCUG
GGCCUACCGCCUGGCCGUGCGCUCCUACGCCGGCUGCUCCCGCACCACC
CCCCCCCCCCGCUGCUUCGCCGAGGCCCGCAUGGAGCCCGUGCCCGGCC
UGGCCUGGCUGGCCUCCACCGUGAACCUGGAGUUCCAGCACGCCUCCCC
CCAGCACGCCGGCCUGUACCUGUGCGUGGUGUACGUGGACGACCACAUC
CACGCCUGGGGCCACAUGACCAUCUCCACCGCCGCCCAGUACCGCAACG
CCGUGGUGGAGCAGCACCUGCCCCAGCGCCAGCCCGAGCCCGUGGAGCC
CACCCGCCCCCACGUGCGCGCCUAA*CUAGUAGUGACUGACUAGGAUCUG*
*GUUACCACUAAACCAGCCUCAAGAACACCCGAAUGGAGUCUCUAAGCUA*
*CAUAAUACCAACUUACACUUACAAAAUGUUGUCCCCCAAAAUGUAGCCA*
*UUCGUAUCUGCUCCUAAUAAAAAGAAAGUUUCUUCACAUUCUAAAAAAA*
*AAAAAAAAAAAAAAAAAAAAAAAAAAAAAAAAAAAAAAAAAAAAAAAAA*
*AAAAAAAAAAAAAAAAAAAAAAAAAAAAAAAAAAAAAAAAAAAAAAAAC*

In one embodiment, all uridine residues are 1-methyl-pseudouridine. In one embodiment, underlined residues represent 5' untranslated sequences. In one embodiment, bold residues represent a signal sequence (leader sequence) to assist expression of the gE2 fragment. In one embodiment, italicized residues represent 3' untranslated sequences and poly adenylation tail.

In another embodiment, the nucleotide sequence of the modified mRNA encoding an HSV-2 gE fragment lacks the 5' untranslated sequences, the signal sequence, the 3' untranslated sequences, the poly adenylation tail, or a combination thereof.

In one embodiment, the HSV-2 gE fragment encoded by modified mRNA utilized in the methods and compositions of the present invention comprises amino acids 24-405 of gE from HSV-2 strain 2.12 as set forth in the following amino acid sequence:

(SEQ ID NO: 17)

RTSWKRVTSGEDVVLLPAPAGPEERTRAHKLLWAAEPLDACGPLRPSWV
ALWPPRRVLETVVDAACMRAPEPLAIAYSPPFPAGDEGLYSELAWRDRV
AVVNESLVIYGALETDSGLYTLSVVGLSDEARQVASVVLVVEPAPVPTP
TPDDYDEEDDAGVSERTPVSVPPPTPPRRPPVAPPTHPRVIPEVSHVRG
VTVHMETPEAILFAPGETFGTNVSIHAIAHDDGPYAMDVVWMRFDVPSS
CAEMRIYEACLYHPQLPECLSPADAPCAVSSWAYRLAVRSYAGCSRTTP
PPRCFAEARMEPVPGLAWLASTVNLEFQHASPQHAGLYLCVVYVDDHIH
AWGHMTISTAAQYRNAVVEQHLPQRQPEPVEPTRPHVRA.

In one embodiment, the full length HSV-2 gE encoded by modified mRNA utilized in the methods and compositions of the present invention comprises the following amino acid sequence:

(SEQ ID NO: 18)

MARGAGLVFFVGVWVVSCLAAAPRTSWKRVTSGEDVVLLPAPAERTRAH
KLLWAAEPLDACGPLRPSWVALWPPRRVLETVVDAACMRAPEPLAIAYS
PPFPAGDEGLYSELAWRDRVAVVNESLVIYGALETDSGLYTLSVVGLSD
EARQVASVVLVVEPAPVPTPTPDDYDEEDDAGVTNARRSAFPPQPPPRR
PPVAPPTHPRVIPEVSHVRGVTVHMETLEAILFAPGETFGTNVSIHAIA
HDDGPYAMDVVWMRFDVPSSCADMRIYEACLYHPQLPECLSPADAPCAV
SSWAYRLAVRSYAGCSRTTPPPRCFAEARMEPVPGLAWLASTVNLEFQH
ASPQHAGLYLCVVYVDDHIHAWGHMTISTAAQYRNAVVEQHLPQRQPEP
VEPTRPHVRAPHPAPSARGPLRLGAVLGAALLLAALGLSAWACMTCWRR
RSWRAVKSRASATGPTYIRVADSELYADWSSDSEGERDGSLWQDPPERP
DSPSTNGSGFEILSPTAPSVYPHSEGRKSRRPLTTFGSGSPGRRHSQAS
YPSVLW.

In another embodiment, the HSV-2 gE encoded by modified mRNA utilized in the methods and compositions of the present invention comprises the amino acid sequences as set forth in any of the following GenBank Accession Numbers: ABU45436.1, ABU45437.1, ABU45438.1, ABU45439.1, ABW83306.1, ABW83308.1, ABW83310.1, ABW83312.1, ABW83314.1, ABW83316.1, ABW83318.1, ABW83320.1, ABW83322.1, ABW83324.1, ABW83326.1, ABW83328.1, ABW83330.1, ABW83332.1, ABW83334.1, ABW83336.1, ABW83338.1, ABW83340.1, ABW83342.1, ABW83344.1, ABW83346.1, ABW83348.1, ABW83350.1, ABW83352.1, ABW83354.1, ABW83356.1, ABW83358.1, ABW83360.1, ABW83362.1, ABW83364.1, ABW83366.1, ABW83368.1, ABW83370.1, ABW83372.1, ABW83374.1, ABW83376.1, ABW83378.1, ABW83380.1, ABW83382.1, ABW83384.1, ABW83386.1, ABW83388.1, ABW83390.1, ABW83392.1, ABW83394.1, ABW83396.1, ABW83398.1, ABW83400.1, ABZ04069.1, AEV91407.1, AHG54732.1, AKC42830.1, AKC59307.1, AKC59378.1, AKC59449.1, AKC59520.1, AKC59591.1, AMB66104.1, AMB66173.1, AMB66246.1, AMB66465.1, AQZ55756.1, AQZ55827.1, AQZ55898.1, AQZ55969.2, AQZ56040.2, AQZ56111.2, AQZ56182.1, AQZ56253.2, AQZ56324.1, AQZ56395.1, AQZ56466.2, AQZ56537.1, AQZ56608.1, AQZ56679.1, AQZ56750.1, AQZ56821.2, AQZ56892.1, AQZ56963.2, AQZ57034.2, AQZ57105.1, AQZ57176.1, AQZ57247.2, AQZ57318.2, AQZ57389.2, AQZ57460.2, AQZ57531.2, AQZ57602.2, AQZ57673.1, AQZ57744.2, AQZ57815.1, AQZ57886.1, AQZ57957.2, AQZ58028.2, AQZ58099.1, AQZ58170.2, AQZ58241.2, AQZ58312.2, AQZ58383.2, AQZ58454.2, AQZ58525.2, AQZ58596.1, AQZ58667.1, AQZ58738.2, AQZ58809.2, AQZ58880.2, AQZ58951.2, AQZ59022.2, AQZ59093.1, AQZ59164.1, ARO38081.1, ARO38082.1, ARO38083.1, ARO38084.1, ARO38085.1, ARO38086.1, CAB06715.1, P89436.1, P89475.1, or YP_009137220.1.

In another embodiment, a gE fragment encoded by modified mRNA utilized in the methods and compositions of the present invention comprises an IgG Fc-binding domain of the gE protein. In another embodiment, the gE domain encoded by modified mRNA utilized in the methods and compositions of the present invention is any other gE domain known in the art to mediate binding to IgG Fc.

In another embodiment, the gE protein encoded by modified mRNA utilized in the methods and compositions of the present invention comprises a gE domain involved in cell-to-cell spread.

In another embodiment, the gE fragment encoded by modified mRNA fragment utilized in the methods and compositions of the present invention comprises an immune evasion domain.

In another embodiment, the gE fragment encoded by modified mRNA fragment utilized in the methods and compositions of the present invention comprises a portion of an immune evasion domain.

Each modified mRNA encoding gE-1 or gE-2 protein or fragment thereof represents a separate embodiment of the present invention.

In another embodiment, a gE protein fragment encoded by modified mRNA utilized in the methods and compositions of the present invention is an immunogenic fragment. In another embodiment, a gE immunoprotective antigen need not be the entire protein. The protective immune response generally involves, in another embodiment, an antibody response. In another embodiment, mutants, sequence conservative variants, and functional conservative variants of gE are useful in methods and compositions of the present invention, provided that all such variants retain the required immuno-protective effect. In another embodiment, the immunogenic fragment can comprise an immuno-protective gE antigen from any strain of HSV. In another embodiment, the immunogenic fragment can comprise sequence variants of HSV, as found in infected individuals.

In one embodiment, an HSV glycoprotein encoded by modified mRNA utilized in the methods and compositions of the present invention is a homologue of the sequence provided herein. In another embodiment, an HSV glycoprotein encoded by modified mRNA utilized in the methods and compositions of the present invention is an isoform of the sequence provided herein. In another embodiment, an HSV glycoprotein encoded by modified mRNA utilized in the methods and compositions of the present invention is a variant of the sequence provided herein. In another embodiment, an HSV glycoprotein encoded by modified mRNA utilized in the methods and compositions of the present invention is a fragment of the sequence provided herein.

In another embodiment, the glycoprotein fragment encoded by modified mRNA of the methods and compositions of the present invention comprises the ectodomain of the glycoprotein. In another embodiment, the glycoprotein fragment encoded by modified mRNA of the methods and compositions of the present invention consists of the ectodomain of the glycoprotein. In another embodiment, the glycoprotein fragment encoded by modified mRNA of the methods and compositions of the present invention comprises a fragment of the ectodomain of the glycoprotein. In another embodiment, the glycoprotein fragment may be any glycoprotein fragment known in the art.

In another embodiment, the glycoprotein or immunogenic fragment encoded by modified mRNA fragment utilized in the methods and compositions of the present invention may be from any strain of HSV. In another embodiment, the immunogenic fragment encoded by modified mRNA fragment utilized in the methods and compositions of the present invention may comprise sequence variants of HSV, as found in infected individuals.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of one or more amino acids.

"Immune evasion domain" refers, in one embodiment, to a domain that interferes with or reduces in vivo anti-HSV efficacy of anti-HSV antibodies (e.g. anti-gD antibodies). In another embodiment, the domain interferes or reduces in vivo anti-HSV efficacy of an anti-HSV immune response. In another embodiment, the domain reduces the immunogenicity of an HSV protein (e.g. gD) during subsequent infection. In another embodiment, the domain reduces the immunogenicity of an HSV protein during subsequent challenge. In another embodiment, the domain reduces the immunogenicity of HSV during subsequent challenge. In another embodiment, the domain reduces the immunogenicity of an HSV protein in the context of ongoing HSV infection. In another embodiment, the domain reduces the immunogenicity of HSV in the context of ongoing HSV infection. In another embodiment, the domain functions as an IgG Fc receptor. In another embodiment, the domain promotes antibody bipolar bridging, which in one embodiment, is a term that refers to an antibody molecule binding by its Fab domain to an HSV antigen and by its Fe domain to a separate HSV antigen, such as in one embodiment, gE, thereby blocking the ability of the Fc domain to activate complement.

The present invention also provides for modified mRNA encoding analogs of HSV proteins or polypeptides, or fragments thereof. Analogs may differ from naturally occurring proteins or peptides by conservative amino acid sequence substitutions or by modifications which do not affect sequence, or by both.

In another embodiment, an HSV glycoprotein encoded by modified mRNA of the present invention is homologous to a sequence set forth hereinabove, either expressly or by reference to a GenBank entry. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, "homology" refers to identity of a protein sequence encoded by a modified mRNA to a sequence disclosed herein of greater than 70%. In another embodiment, the identity is greater than 72%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%. In another embodiment, the identity is greater than 92%. In another embodiment, the identity is greater than 93%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%.

In one embodiment, "isoform" refers to a version of a molecule, for example, a protein, with only slight differences to another isoform of the same protein. In one embodiment, isoforms may be produced from different but related genes, or in another embodiment, may arise from the same gene by alternative splicing. In another embodiment, isoforms are caused by single nucleotide polymorphisms.

In another embodiment, the modified mRNA encoding a glycoprotein or glycoprotein fragment as described herein further encodes an antigenic tag. In one embodiment, the tag is a histidine ("His") tag. In one embodiment, the His tag comprises 5 histidine residues. In another embodiment, the His tag comprises 6 histidine residues.

In another embodiment, methods and compositions of the present invention utilize a chimeric molecule, comprising a fusion of a modified mRNA encoding an HSV protein with a modified mRNA encoding a tag polypeptide that provides an epitope to which an anti-tag antibody can selectively bind. The epitope tag is placed, in other embodiments, at the amino- or carboxyl-terminus of the protein or in an internal location therein. The presence of such epitope-tagged forms of the recombinant HSV protein is detected, in another embodiment, using an antibody against the tag polypeptide. In another embodiment, inclusion of the epitope tag enables the recombinant HSV protein to be readily purified by affinity purification using an anti-tag antibody or another type of affinity matrix that binds to the epitope tag. Various tag polypeptides and their respective antibodies are known in the art.

In one embodiment, the compositions of the present invention comprise an adjuvant, while in another embodiment, the compositions do not comprise an adjuvant. "Adjuvant" refers, in another embodiment, to compounds that, when administered to an individual or tested in vitro, increase the immune response to an antigen in the individual or test system to which the antigen is administered. In another embodiment, an immune adjuvant enhances an immune response to an antigen that is weakly immunogenic when administered alone, i.e., inducing no or weak antibody titers or cell-mediated immune response. In another embodiment, the adjuvant increases antibody titers to the antigen. In another embodiment, the adjuvant lowers the dose of the antigen effective to achieve an immune response in the individual. Multiple types of adjuvants are known in the art and described in detail in U. S. Patent Publication 2013/0028925 which is hereby incorporated by reference herein.

Modified mRNAs

In one embodiment, the present invention provides compositions comprising modified mRNAs and methods of use thereof. In one embodiment, the modified mRNA comprises one or more modified nucleoside residues.

In another embodiment, the modified nucleoside of the methods and compositions of the present invention is m5C (5-methylcytidine). In another embodiment, the modified nucleoside is m5U (5-methyluridine). In another embodiment, the modified nucleoside is m6A (N6-methyladenosine). In another embodiment, the modified nucleoside is s2U (2-thiouridine). In another embodiment, the modified nucleoside is Ψ (pseudouridine). In another embodiment, the modified nucleoside is Um (2'-O-methyluridine).

In other embodiments, the modified nucleoside is $m^1A$ (1-methyladenosine), $m^2A$ (2-methyladenosine), $m^6A$ (N6-methyladenosine), Am (2'-O-methyladenosine), $ms^2m^6A$ (2-methylthio-N6-methyladenosine), $i^6A$ (N6-isopentenyladenosine), $ms^2i^6A$ (2-methylthio-N6-isopentenyladenosine), $io^6A$ (N6-(cis-hydroxyisopentenyl)adenosine), $ms^2io^6A$ (2-methylthio-N6-(cis-hydroxyisopentenyl) adenosine), $g^6A$ (N6-glycinylcarbamoyladenosine), $t^6A$ (N6-threonylcarbamoyladenosine), $ms^2t^6A$ (2-methylthio-N6-threonyl carbamoyladenosine), $m^6t^6A$ (N6-methyl-N6-threonylcarbamoyladenosine), $hn^6A$ (N6-hydroxynorvalylcarbamoyladenosine), $ms^2hn^6A$ (2-methylthio-N6-hydroxynorvalyl carbamoyladenosine), Ar(p) (2'-O-ribosyladenosine (phosphate)), I (inosine), $m^1I$ (1-methylinosine), $m^1Im$ (1,2'-O-dimethylinosine), $m^3C$ (3-methylcytidine), $m^5C$ (5-methylcytidine), Cm (2'-O-methylcytidine), $s^2C$ (2-thiocytidine), $ac^4C$ (N4-acetylcytidine), $f^5C$ (5-formylcytidine), $m^5Cm$ (5,2'-O-dimethylcytidine), $ac^4Cm$ (N4-acetyl-2'-O-methylcytidine), $k^2C$ (lysidine), $m^1G$ (1-methylguanosine), $m^2G$ (N2-methylguanosine), $m^7G$ (7-methylguanosine), Gm (2'-O-methylguanosine), $m^2{}_2G$ (N2,N2-dimethylguanosine), $m^2Gm$ (N2,2'-O-dimethylguanosine), $m^2{}_2Gm$ (N2,N2,2'-O-trimethylguanosine), Gr(p) (2'-O-ribosylguanosine (phosphate)), yW (wybutosine), $o_2yW$ (peroxywybutosine), OHyW (hydroxywybutosine), OHyW* (undermodified hydroxywybutosine), imG (wyosine), mimG (methylwyosine), Q (queuosine), oQ (epoxyqueuosine), galQ (galactosyl-queuosine), manQ (mannosyl-queuosine), preQ0 (7-cyano-7-deazaguanosine), preQ1 (7-aminomethyl-7-deazaguanosine), $G^+$ (archaeosine), Ψ (pseudouridine), D (dihydrouridine), $m^5U$ (5-methyluridine), Um (2'-O-methyluridine), $m^5Um$ (5,2'-O-dimethyluridine), $m^1\Psi$ (1 -methylpseudouridine), Ψm (2'-O-methylpseudouridine), $s^2U$ (2-thiouridine), $s^4U$ (4-thiouridine), $m^5s^2U$ (5-methyl-2-thiouridine), $s^2Um$ (2-thio-2'-O-methyluridine), $acp^3U$ (3-(3-amino-3-carboxypropyl)uridine), $ho^5U$ (5-hydroxyuridine), $mo^5U$ (5-methoxyuridine), $cmo^5U$ (uridine 5-oxyacetic acid), $mcmo^5U$ (uridine 5-oxyacetic acid methyl ester), $chm^5U$ (5-(carboxyhydroxymethyl)uridine), $mchm^5U$ (5-(carboxyhydroxymethyl)uridine methyl ester), $mcm^5U$ (5-methoxycarbonylmethyluridine), $mcm^5Um$ (5-methoxycarbonylmethyl-2'-O-methyluridine), mcm$^5$s$^2$U (5-methoxycarbonylmethyl-2-thiouridine), nm$^5$s$^2$U (5-aminomethyl-2-thiouridine), mnm$^5$U (5-methylaminomethyluridine), mnm$^5$s$^2$U (5-methylaminomethyl-2-thiouridine), mnm$^5$se$^2$U (5-methylaminomethyl-2-selenouridine), ncm$^5$U (5-carbamoylmethyluridine), nCm$^5$Um (5-carbamoylmethyl-2'-O-methyluridine), cmnm$^5$U (5-carboxymethylaminomethyluridine), cmnm$^5$Um (5-carboxymethylaminomethyl-2'-O-methyluridine), cmnm$^5$s$^2$U (5-carboxymethylaminomethyl-2-thiouridine), m$^6{}_2$A (N6, N6-dimethyladenosine), Im (2'-O-methylinosine), m$^4$C (N4-methylcytidine), m$^4$Cm (N4,2'-O-dimethylcytidine), hm$^5$C (5-hydroxymethylcytidine), m$^3$U (3-methyluridine), m$^1$acp$^3$T (1-methyl-3-(3-amino-3-carboxypropyl)pseudouridine), cm$^5$U (5-carboxymethyluridine), m$^6$Am (N6,2'-O-dimethyladenosine), m$^6{}_2$Am (N6,N6,2'-O-trimethyladenosine), m$^{2,7}$G (N2,7-dimethylguanosine), m$^{2,2,7}$G (N2,N2,7-trimethylguanosine), m$^3$Um (3,2'-O-dimethyluridine), m$^5$D (5-methyldihydrouridine), m$^3\Psi$ (3-methylpseudouridine), f$^5$Cm (5-formyl-2'-O-methylcytidine), m$^1$Gm (1,2'-O-dimethylguanosine), m$^1$Am (1,2'-O-dimethyladenosine), $\tau$m$^5$U (5-taurinomethyluridine), $\tau$m$^5$s$^2$U (5-taurinomethyl-2-thiouridine), imG-14 (4-demethylwyosine), imG2 (isowyosine), ac$^6$A (N6-acetyladenosine), inm$^5$U (5-(isopentenylaminomethyl)uridine), inm$^5$s$^2$U (5-(isopentenylaminomethyl)-2-thiouridine), inm$^5$Um (5-(isopentenylaminomethyl)-2'-O-methyluridine), m$^{2,7}$Gm (N2,7,2'-O-trimethylguanosine), m$^4{}_2$Cm (N4,N4,2'-O-trimethylcytidine), C$^+$ (agmatidine), m$^8$A (8-methyladenosine), gmnm$^5$s$^2$U (geranylated 5-methylaminomethyl-2-thiouridine), gcmnm$^5$s$^2$U (geranylated 5-carboxymethylaminomethyl-2-thiouridine), or cnm$^5$U (5-cyanomethyl-uridine).

In one embodiment, the modified nucleoside residues are pseudouridine or pseudouridine family residues.

In one embodiment, the modified mRNA comprises pseudouridine residues. In one embodiment, pseudouridine refers to the C-glycoside isomer of the nucleoside uridine. In one embodiment, pseudouridine residues comprise m$^1$acp$^3\Psi$ (1-methyl-3-(3-amino-5 -carboxypropyl)pseudouridine, m$^1\Psi$ (1-methylpseudouridine), $\Psi$m (2'-O-methylpseudouridine, m$^5$D (5-methyldihydrouridine), m$^3\Psi$ (3-methylpseudouridine), or a combination thereof. In one embodiment, said pseudouridine residues comprise 1-methylpseudouridine residues instead of uridine.

In one embodiment, the modified nucleoside residues are pseudouridine analogues. In one embodiment, a "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine (m$^1\Psi$), 1-methyl-4-thio-pseudouridine (m$^1$s$^4\Psi$), 4-thio-1-methyl-pseudouridine, 3-methyl-pseudouridine (m$^3\Psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine (acp$^3\Psi$), and 2'-O-methyl-pseudouridine ($\Psi$m).

In some embodiments, the modified nucleobase is a modified uracil. Exemplary nucleobases and nucleosides having a modified uracil include pseudouridine ($\Psi$), pyridin-4-one ribonucleoside, 5-aza-uridine, 6-aza-uridine, 2-thio-5-aza-uridine, 2-thio-uridine (s$^2$U), 4-thio-uridine (s$^4$U), 4-thio-pseudouridine, 2-thio-pseudouridine, 5-hydroxy-uridine (ho$^5$U), 5-aminoallyl-uridine, 5-halo-uridine (e.g., 5-iodo-uridine or 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine ($\tau$cm$^5$U), 1-taurinomethyl-pseudouridine, 5-taurinomethyl-2-thio-uridine ($\tau$rm$^5$s$^2$U), 1-taurinomethyl-4-thio-pseudouridine, 5-methyl-uridine (m$^5$U, i.e., having the nucleobase deoxythymine), 1-methylpseudouridine (m$^1\Psi$), 5-methyl-2-thio-uridine (m$^5$s$^2$U), 1-methyl-4-thio-pseudouridine (m$^1$s$^4\Psi$), 4-thio-1-methyl-pseudouridine, 3-methyl-pseudouridine (m$^3\Psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine (also known as 1-methylpseudouridine (m$^1\Psi$), 3-(3-amino-3-carboxypropyl)uridine (acp$^3$U), 1-methyl-3-(3-amino-3-carboxypropyl)pseudouridine (acp$^3\Psi$), 5-(isopentenylaminomethyl)uridine (inm$^5$U), 5-(isopentenylaminomethyl)-2-thio-uridine (inm$^5$s$^2$U), $\alpha$-thio-uridine, 2'-O-methyl-uridine (Um), 5,2'-O-dimethyl-uridine (m$^5$Um), 2'-O-methyl-pseudouridine ($\Psi$m), 2-thio-2'-O-methyl-uridine (s$^2$Um), 5-methoxycarbonylmethyl-2'-O-methyl-uridine (mcm$^5$Um), 5-carbamoylmethyl-2'-$\beta$-methyl-uridine (ncm$^5$Um), 5-carboxymethylaminomethyl-2'-O-methyl-uridine (cmnm$^5$Um), 3,2'-O-dimethyl-uridine (m$^3$Um), 5-(isopentenylaminomethyl)-2'-$\beta$-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl)uridine, and 5-[3-(1-E-propenylamino)uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m$^3$C), N4-acetyl-cytidine (ac$^4$C), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s$^2$C), 2-thio-5-methyl-cytidine, 4-thio-pseudoisocytidine, 4-thio-I-methyl-pseudoisocytidine, 4-thio-i-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-i-methyl-pseudoisocytidine, lysidine (k$_2$C), $\alpha$-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2'-O-dimethyl-cytidine (m$^4$Cm), 5-formyl-2'-O-methyl-cytidine (f$^5$Cm), N4,N4,2'-O-trimethyl-cytidine (m$^4{}_2$Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2 m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6{}_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^{6A}$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6{}_2Am$), 1,2'-O-dimethyl-adenosine ($m^1Am$), 2'-β-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2{}_2G$), N2,7-dimethyl-guanosine ($m^2$,7G), N2,N2,7-dimethyl-guanosine ($m^2$,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2{}_2Gm$), 1-methyl-2'-O-methyl-guanosine ($m^1Gm$), N2,7-dimethyl-2'-O-methyl-guanosine ($m^{2'7}Gm$), 2'-O-methyl-inosine (Im), 1,2'-O-dimethyl-inosine ($m^1Im$), and 2'-O-ribosylguanosine (phosphate) (Gr(p)).

The nucleobase of the nucleotide can be independently selected from a purine, a pyrimidine, a purine or pyrimidine analog. For example, the nucleobase can each be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Modifications on the Internucleoside Linkage

The modified nucleotides, which may be incorporated into a polynucleotide, primary construct, or mRNA molecule, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked polynucleotides, primary constructs, or mmRNA molecules are expected to also reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein below.

Combinations of Modified Sugars, Nucleobases, and Internucleoside Linkages

The polynucleotides, primary constructs, and mmRNA of the invention can include a combination of modifications to the sugar, the nucleobase, and/or the internucleoside linkage.

In another embodiment, the purified preparation of RNA, oligoribonucleotide, or polyribonucleotide of the methods and compositions of the present invention comprises a combination of two or more of the above-described modifications. In another embodiment, the purified preparation of the RNA or oligoribonucleotide comprises a combination of three or more of the above-described modifications. In another embodiment, the purified preparation of the RNA or oligoribonucleotide comprises a combination of more than three of the above-described modifications.

In one embodiment, the modified mRNAs comprise in vitro-synthesized modified mRNAs.

In one embodiment, the present invention comprises one or more modified mRNAs encoding an HSV glycoprotein. In one embodiment, the modified RNA comprises pseudouridine or pseudouridine family residues. In another embodiment, the modified mRNAs of the present invention are capable of directing protein expression of HSV glycoproteins encoded thereon.

In another embodiment, the present invention provides an in vitro-transcribed mRNA molecule encoding an HSV glycoprotein, comprising a pseudouridine. In another embodiment, the present invention provides a synthetic mRNA molecule encoding an HSV glycoprotein, comprising a pseudouridine.

In another embodiment, an in vitro-transcribed mRNA molecule of the methods and compositions of the present invention is synthesized by T7 phage RNA polymerase. In another embodiment, the molecule is synthesized by SP6 phage RNA polymerase. In another embodiment, the molecule is synthesized by T3 phage RNA polymerase. In another embodiment, the molecule is synthesized by a polymerase selected from the above polymerases. In another embodiment, the mRNA is synthesized chemically on a column similar to DNA.

In another embodiment, the nucleoside that is modified in an RNA, oligoribonucleotide, or polyribonucleotide of the methods and compositions of the present invention is uridine (U). In another embodiment, the modified nucleoside is cytidine (C). In another embodiment, the modified nucleoside is adenine (A). In another embodiment the modified nucleoside is guanine (G).

In another embodiment, the modified mRNA of the methods and compositions of the present invention further comprises a poly-A tail. In another embodiment, the modified mRNA of the methods and compositions of the present invention does not comprise a poly-A tail. Each possibility represents a separate embodiment of the present invention.

In another embodiment, the modified mRNA of the methods and compositions of the present invention comprises an m7GpppG cap. In another embodiment, the modified mRNA of the methods and compositions of the present invention does not comprise an m7GpppG cap. In another embodiment, the modified mRNA of the methods and compositions of the present invention comprises a 3'-O-methyl-m7GpppG. In another embodiment, the modified mRNA of methods and composition of the present invention comprise a non-reversible cap analog, which, in one embodiment, is added during transcription of the mRNA. In another embodiment, the modified mRNA of methods and composition of the present invention comprise an anti-reverse cap analog. Each possibility represents a separate embodiment of the present invention.

In another embodiment, the modified mRNA of the methods and compositions of the present invention further comprises a cap-independent translational enhancer. In another embodiment, the modified mRNA of the methods and compositions of the present invention does not comprise a cap-independent translational enhancer. In another embodiment, the cap-independent translational enhancer is a tobacco etch virus (TEV) cap-independent translational enhancer. In another embodiment, the cap-independent translational enhancer is any other cap-independent translational enhancer known in the art. Each possibility represents a separate embodiment of the present invention.

In one embodiment, "pseudouridine" refers to $m^1acp^3\Psi$ (1-methyl-3-(3-amino-5-carboxypropyl)pseudouridine. In another embodiment, the term refers to $m^1\Psi$ (1-methylpseudouridine). In another embodiment, the term refers to $\Psi m$ (2'-O-methylpseudouridine. In another embodiment, the term refers to $m^5D$ (5-methyldihydrouridine). In another embodiment, the term refers to $m^3\Psi$ (3-methylpseudouridine). In another embodiment, the modified nucleoside is 4' (pseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

In another embodiment, the modified RNA comprises a modified nucleoside, which in one embodiment, comprises $m^5C$, m5U, $m^6A$, $s^2U$, $\Psi$, 2'-O-methyl-U, 2'-O-methylpseudouridine, or a combination thereof.

In another embodiment, the present invention provides a method for delivering a recombinant protein to a subject, the method comprising the step of contacting the subject with a modified mRNA of the methods and compositions of the present invention, thereby delivering a recombinant protein to a subject.

In another embodiment, a method of the present invention comprises increasing the number, percentage, or frequency of modified uridine nucleosides in the RNA molecule to decrease immunogenicity or increase efficiency of translation. In one embodiment, the number of modified uridine residues in an RNA, oligoribonucleotide, or polyribonucleotide molecule determines the magnitude of the effects observed in the present invention.

In another embodiment, between 0.1% and 100% of the uridine residues in the modified mRNAs of the methods and compositions of the present invention are modified (e.g. by the presence of pseudouridine). In another embodiment, 0.1% of the residues are modified. In another embodiment, 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%

In another embodiment, 0.1% of the residues of a given uridine nucleotide are modified. In another embodiment, the fraction of the nucleotide is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction of the given uridine nucleotide is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, the terms "ribonucleotide," "oligoribonucleotide," and polyribonucleotide refers to, in one embodiment, compounds comprising nucleotides in which the sugar moiety is ribose. In another embodiment, the term includes both RNA and RNA derivates in which the backbone is modified. Numerous RNA backbone modifications are known in the art and contemplated in the present invention. In one embodiment, modified RNA is a PNA (peptide nucleic acid). PNA contain peptide backbones and nucleotide bases and are able to bind, in another embodiment, to both DNA and RNA molecules. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. Each nucleic acid derivative represents a separate embodiment of the present invention.

Methods for production of nucleic acids having modified backbones are well known in the art, and are described, for example in U.S. Pat. Nos. 5,723,335 and 5,663,153 issued to Hutcherson et al. and related PCT publication WO95/26204. Each method represents a separate embodiment of the present invention.

The nucleic acid of interest can be purified by any method known in the art, or any method to be developed, so long as the method of purification removes contaminants from the nucleic acid preparation and thereby substantially reduces the immunogenicity potential of the nucleic acid preparation. In one embodiment, the nucleic acid of interest is purified using high-performance liquid chromatography (HPLC). In another embodiment, the nucleic acid of interest is purified by contacting the nucleic acid of interest with the bacterial enzyme RNase III. In other various embodiments, any method of nucleic acid purification that substantially reduces the immunogenicity of the nucleic acid preparation can be used. Non-limiting examples of purification methods that can be used with the compositions and methods of the invention liquid chromatography separation and enzyme digestion, each used alone or in any combination, simultaneously or in any order. Non-limiting examples of liquid chromatography separation include HPLC and fast protein liquid chromatography (FPLC). Materials useful in the HPLC and FPLC methods of the invention include, but are not limited to, cross-linked polystyrene/divinylbenzene (PS/DVB), PS/DVB-C18, PS/DVB-alkylated, Helix DNA columns (Varian), Eclipse dsDNA Analysis Columns (Agilent Technologies), Reverse-phase 5 (RPC-5) exchange material, DNAPac, ProSwift, and bio-inert UltiMate® 3000 Titanium columns (Dionex). Enzymes useful in the enzyme digestion methods of the invention include any enzyme able to digest any contaminant in a nucleic acid preparation of the invention, such as, for example a dsRNA contaminant, and include but are not limited to, RNase III, RNase V1, Dicer, and Chipper (see Fruscoloni et al., 2002, PNAS 100:1639) Non-limiting examples of assays for assessing the purity of the nucleic acid of interest include a dot-blot assay, a Northern blot assay, and a dendritic cell activation assay, as described elsewhere herein.

In another embodiment, the modified mRNA of the methods and compositions of the present invention is significantly less immunogenic than an unmodified in vitro-synthesized mRNA molecule with the same sequence. In another embodiment, the modified mRNA molecule is 2-fold less immunogenic than its unmodified counterpart. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a fold factor. In another embodiment, immunogenicity is reduced by a 50-fold factor. In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

In another embodiment, "significantly less immunogenic" refers to a detectable decrease in immunogenicity. In another embodiment, the term refers to a fold decrease in immunogenicity (e.g. 1 of the fold decreases enumerated above). In another embodiment, the term refers to a decrease such that an effective amount of the modified mRNA can be administered without triggering a detectable immune response. In another embodiment, the term refers to a decrease such that the modified mRNA can be repeatedly administered without eliciting an immune response sufficient to detectably reduce expression of the recombinant protein. In another embodiment, the decrease is such that the modified mRNA can be repeatedly administered without eliciting an immune response sufficient to eliminate detectable expression of the recombinant protein.

Methods of determining immunogenicity are well known in the art, and described in detail in U.S. Pat. No. 8,278,036 which is hereby incorporated by reference herein.

In another embodiment, the modified mRNA of the methods and compositions of the present invention is translated in the cell more efficiently than an unmodified mRNA molecule with the same sequence. In another embodiment, the modified mRNA exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 5-fold factor. In another embodiment, translation is enhanced by a 7-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts. Each possibility represents a separate embodiment of the present invention.

Methods of determining translation efficiency are well known in the art, and include, e.g. measuring the activity of an encoded reporter protein (e.g luciferase or *renilla* or green fluorescent protein [Wall A A, Phillips A M et al, Effective translation of the second cistron in two *Drosophila* dicistronic transcripts is determined by the absence of in-frame AUG codons in the first cistron. J Biol Chem 2005; 280(30): 27670-8]), or measuring radioactive label incorporated into the translated protein (Ngosuwan J, Wang N M et al, Roles of cytosolic Hsp70 and Hsp40 molecular chaperones in post-translational translocation of pre-secretory proteins into the endoplasmic reticulum. J Biol Chem 2003; 278(9): 7034-42). Each method represents a separate embodiment of the present invention.

In another embodiment, the target cell of the method of the present invention is a dendritic cell. In another embodiment, the target cell of the method of the present invention is a macrophage. In another embodiment, the target cell of the method of the present invention is a B cell. In another embodiment, the target cell of the method of the present invention is another antigen presenting cell. In another embodiment, the target cell of methods of the present invention is a mucosal cell. In another embodiment, the target cell of methods of the present invention is an epithelial cell. In another embodiment, the cell is a skin cell. In another embodiment, the cell is an epidermal cell. In another embodiment, the cell is a keratinocyte. In another embodiment, the cell is a Merkel cell, melanocyte or Langerhans cell. Each possibility represents a separate embodiment of the present invention.

Methods of Treatment and Uses of the Compositions

The present invention also provides methods of vaccinating a subject against HSV and treating, impeding, inhibiting, reducing the incidence of, or suppressing an HSV infection or a symptom or manifestation thereof, comprising administration of a composition of the present invention.

In one embodiment, the present invention provides a method for treating an HSV infection in a subject, comprising contacting said subject with a composition comprising one or more modified mRNAs, wherein each of said modified mRNAs encodes an HSV glycoprotein or immunogenic fragment thereof.

In another embodiment, the present invention provides a method for suppressing an HSV infection in a subject, comprising contacting said subject with a composition comprising one or more modified mRNAs, wherein each of said modified mRNAs encodes an HSV glycoprotein or immunogenic fragment thereof.

In another embodiment, the present invention provides a method for inhibiting an HSV infection in a subject, comprising contacting said subject with a composition comprising one or more modified mRNAs, wherein each of said modified mRNAs encodes an HSV glycoprotein or immunogenic fragment thereof.

In another embodiment, the present invention provides a method for reducing the incidence of HSV infection in a subject, comprising contacting said subject with a composition comprising one or more modified mRNAs, wherein each of said modified mRNAs encodes an HSV glycoprotein or immunogenic fragment thereof.

In one embodiment, the HSV infection is an HSV-1 infection. In another embodiment, the HSV infection is an HSV-2 infection.

In one embodiment, the subject is administered HSV-1 glycoproteins for methods of treating, inhibiting, suppressing, etc. an HSV-1 infection. In another embodiment, the subject is administered HSV-2 glycoproteins for methods of treating, inhibiting, suppressing, etc. an HSV-2 infection. In another embodiment, the subject is administered HSV-1 glycoproteins for methods of treating, inhibiting, suppressing, etc. an HSV-1 infection, HSV-2 infection, or a combination thereof. In another embodiment, the subject is administered HSV-2 glycoproteins for methods of treating, inhibiting, suppressing, etc. an HSV-1 infection, HSV-2 infection, or a combination thereof. In one embodiment, administration of HSV-1 glycoproteins (e.g., gC1, gD1, gE1, or a combination thereof) treats or prevents HSV-1 and HSV-2 infection. In another embodiment, administration of HSV-2 glycoproteins (e.g., gC2, gD2 and gE2, or a combination thereof) treats or prevents HSV-1 and HSV-2 infection.

According to this aspect and in one embodiment, the present invention provides a method for treating, suppressing, inhibiting, or reducing the incidence of Herpes Simplex Virus 1 (HSV-1) infection in a subject, comprising contacting said subject with a composition comprising one or more modified mRNAs, wherein each of said modified mRNAs encodes an HSV-1 glycoprotein or immunogenic fragment thereof.

In one embodiment, the present invention provides a method for treating, suppressing, inhibiting, or reducing the incidence of Herpes Simplex Virus 2 (HSV-2) infection in a subject, comprising contacting said subject with a composition comprising one or more modified mRNAs, wherein each of said modified mRNAs encodes an HSV-2 glycoprotein or immunogenic fragment thereof.

In one embodiment, said contacting is via administration to said subject.

In another embodiment, the present invention provides a method of treating, suppressing, inhibiting, or reducing the incidence of an HSV infection in a subject, the method comprising the step of administering to said subject an immunogenic composition comprising modified mRNAs encoding: (a) an HSV gD or immunogenic fragment thereof, (b) an HSV gC or fragment thereof as described herein; (c) an HSV gE or fragment thereof as described herein, or a combination thereof.

In another embodiment, the present invention provides a method of treating, suppressing, inhibiting, or reducing the incidence of an HSV infection in a subject, the method comprising the step of administering to said subject an immunogenic composition comprising modified mRNAs encoding: (a) an HSV-2 gD or immunogenic fragment thereof, (b) an HSV-2 gC or fragment thereof as described herein; and (c) an HSV-2 gE or fragment thereof as described herein, or a combination thereof.

In another embodiment, the present invention provides a method of treating, suppressing, inhibiting, or reducing the incidence of an HSV infection in a subject, the method comprising the step of administering to said subject an immunogenic composition comprising modified mRNAs encoding: (a) an HSV-1 gD or immunogenic fragment thereof, (b) an HSV-1 gC or fragment thereof as described herein; and (c) an HSV-1 gE or fragment thereof as described herein, or a combination thereof.

In another embodiment, the present invention provides a method of inducing an anti-HSV immune response in a subject, the method comprising the step of administering to said subject an immunogenic composition comprising modified mRNAs encoding: (a) an HSV gD or immunogenic fragment thereof, (b) an HSV gC or fragment thereof as described herein; (c) an HSV gE or fragment thereof as described herein, or a combination thereof.

In another embodiment, the present invention provides a method of inducing an anti-HSV immune response in a subject, the method comprising the step of administering to said subject an immunogenic composition comprising modified mRNAs encoding: (a) an HSV-2 gD or immunogenic fragment thereof; (b) an HSV-2 gC or fragment thereof as described herein; and (c) an HSV-2 gE or fragment thereof as described herein, or a combination thereof.

In another embodiment, the present invention provides a method of inducing an anti-HSV immune response in a subject, the method comprising the step of administering to said subject an immunogenic composition comprising modified mRNAs encoding: (a) an HSV-1 gD or immunogenic fragment thereof; (b) an HSV-1 gC or fragment thereof as described herein; and (c) an HSV-1 gE or fragment thereof as described herein, or a combination thereof.

In another embodiment, the present invention provides a method of inhibiting a primary HSV infection in a subject, the method comprising the step of administering to the subject a composition of the present invention. In another embodiment, the present invention provides a method of treating an HSV infection in a subject, the method comprising the step of administering to said subject a composition of the present invention. In another embodiment, the present invention provides a method of reducing the incidence of an HSV infection in a subject, the method comprising the step of administering to said subject a composition of the present invention. In another embodiment, the present invention provides a method of inhibiting a flare following a primary HSV infection in a subject, the method comprising the step of administering to said subject a composition of the present invention.

In one embodiment, the present invention provides methods of treating and/or suppressing a primary HSV infection and/or a secondary HSV infection. In one embodiment, a "primary" infection refers to a first-time infection. In one embodiment, a "secondary" infection refers to a recurrence of an HSV infection.

In one embodiment, a "flare" or "recurrence" refers to reinfection of skin tissue following latent neuronal HSV infection. In another embodiment, the terms refer to reactivation of HSV after a latency period. In another embodiment, the terms refer to symptomatic HSV lesions following a non-symptomatic latency period.

In another embodiment, the present invention provides a method of inhibiting spread of HSV. In one embodiment, the spread from DRG to skin is inhibited. In one embodiment, cell-to-cell spread of HSV is inhibited. In one embodiment, anterograde spread is inhibited. In one embodiment, retrograde spread is inhibited. "DRG" refers, in one embodiment, to a neuronal cell body and in another embodiment, contain the neuron cell bodies of nerve fibers. In another embodiment, the term refers to any other definition of "DRG" used in the art. In another embodiment, spread of HSV to neural tissue is inhibited.

In another embodiment, the present invention provides a method of inhibiting a recurrence following a primary HSV infection in a subject, the method comprising the step of administering to said subject a composition of the present invention. In another embodiment, the present invention provides a method of preventing a recurrence following a primary HSV infection in a subject, the method comprising the step of administering to said subject a composition of the present invention.

In another embodiment, the present invention provides a method of inhibiting an HSV labialis following a primary HSV infection in a subject, the method comprising the step of administering to said subject a composition of the present invention.

In another embodiment, the present invention provides a method of preventing a recurrence of an HSV infection, the method comprising the step of administering to said subject a composition of the present invention. In another embodiment, the present invention provides a method of diminishing the severity of a recurrence of an HSV infection, the method comprising the step of administering to said subject a composition of the present invention. In another embodiment, the present invention provides a method of reducing the frequency of a recurrence of an HSV infection, the method comprising the step of administering to said subject a composition of the present invention. In one embodiment, the present invention provides any of the described methods in an HIV-infected subject.

In another embodiment, the present invention provides a method of treating an HSV encephalitis in a subject, the method comprising the step of administering to said subject a composition of the present invention. In another embodiment, the present invention provides a method of reducing the incidence of an HSV encephalitis in a subject, the method comprising the step of administering to said subject a composition of the present invention. "HSV encephalitis" refers, in one embodiment, to an encephalitis caused by a Herpes Simplex Virus-1 (HSV). In another embodiment, the term refers to an encephalitis associated with HSV. In another embodiment, the term refers to any other type of HSV-mediated encephalitis known in the art.

In another embodiment, the present invention provides a method of treating or reducing an HSV neonatal infection in a subject, the method comprising the step of administering to said subject a composition of the present invention.

In another embodiment, the present invention provides a method for introducing an HSV glycoprotein to a cell of a subject, comprising contacting said cell with an in vitro-transcribed mRNA molecule encoding the recombinant protein, wherein said in vitro-transcribed mRNA molecule further comprises a modified nucleoside, thereby introducing said HSV glycoprotein into said cell of said subject.

In another embodiment, the present invention provides a method for inducing a mammalian cell to produce an HSV glycoprotein, comprising contacting said mammalian cell with an in vitro-synthesized mRNA molecule encoding the HSV glycoprotein, the in vitro-synthesized mRNA molecule comprising a pseudouridine, thereby inducing said mammalian cell to produce said HSV glycoprotein.

It is to be understood that reference to HSV herein refers in one embodiment, to HSV-1, while in another embodiment, to HSV-2, while in another embodiment, to HSV-1 and HSV-2.

"HSV-1" refers, in another embodiment, to a Herpes Simplex Virus-1. In another embodiment, the term refers to a KOS strain. In another embodiment, the term refers to an F strain. In another embodiment, the term refers to an NS strain. In another embodiment, the term refers to a CL101 strain. In another embodiment, the term refers to a "17" strain. In another embodiment, the term refers to a "17+syn" strain. In another embodiment, the term refers to a MacIntyre strain. In another embodiment, the term refers to an MP strain. In another embodiment, the term refers to an HF strain. In another embodiment, the term refers to any other HSV-1 strain known in the art.

"HSV-2" refers, in another embodiment, to a Herpes Simplex Virus-2. In another embodiment, the term refers to an HSV-2 333 strain. In another embodiment, the term refers to a 2.12 strain. In another embodiment, the term refers to an HG52 strain. In another embodiment, the term refers to an MS strain. In another embodiment, the term refers to a G strain. In another embodiment, the term refers to a 186 strain. In another embodiment, the term refers to any other HSV-2 strain known in the art.

In another embodiment, the present invention provides a method of vaccinating a subject against an HSV infection, the method comprising the step of administering to said subject a composition of the present invention. In another embodiment, the present invention provides a method of suppressing an HSV infection in a subject, the method comprising the step of administering to said subject a composition of the present invention. In another embodiment, the present invention provides a method of impeding an HSV infection in a subject, the method comprising the step of administering to said subject a composition of the present invention. In another embodiment, the present invention provides a method of impeding a primary HSV infection in a subject, the method comprising the step of administering to said subject a composition of the present invention. In another embodiment, the present invention provides a method of impeding neuronal HSV spread in a subject, the method comprising the step of administering to said subject a composition of the present invention.

The terms "impeding an HSV infection" and "impeding a primary HSV infection" refer, in another embodiment, to decreasing the titer of infectious virus. In another embodiment, the terms refer to decreasing the extent of viral replication.

In another embodiment, the present invention provides a method of reducing the incidence of an HSV-mediated herpetic ocular disease in a subject, the method comprising the step of administering to said subject a composition of the present invention. In another embodiment, the present invention provides a method of treating an HSV-1 corneal infection or herpes keratitis in a subject, the method comprising the step of administering to said subject a composition of the present invention. In another embodiment, the present invention provides a method of reducing the incidence of an HSV-1 corneal infection or herpes keratitis in a subject, the method comprising the step of administering to said subject a composition of the present invention.

In another embodiment, the present invention provides a method of treating, suppressing or inhibiting an HSV genital infection, the method comprising the step of administering to said subject a composition of the present invention. In another embodiment, the present invention provides a method of treating, suppressing or inhibiting any manifestation of recurrent HSV infection, the method comprising the step of administering to said subject a composition of the present invention.

In another embodiment, the present invention provides a method of reducing the incidence of an HSV-mediated genital ulcer disease in a subject, the method comprising the step of administering to said subject a composition of the present invention. In another embodiment, the present invention provides a method of impeding an establishment of a latent HSV infection in a subject, the method comprising the step of administering to said subject a composition of the present invention.

In one embodiment, the present invention provides a method of treating, suppressing or inhibiting a genital herpes infection in a subject, comprising the step of administering to said subject a composition of the present invention. In another embodiment, the present invention provides a method of treating, suppressing or inhibiting an oral herpes infection in a subject, comprising the step of administering to said subject a composition of the present invention.

In another embodiment, the present invention provides a method of reducing the incidence of an HSV-mediated encephalitis in a subject, the method comprising the step of administering to said subject a composition of the present invention.

In another embodiment, the herpes-mediated encephalitis treated or prevented by a method of the present invention is a focal herpes encephalitis. In another embodiment, the herpes-mediated encephalitis is a neonatal herpes encephalitis. In another embodiment, the herpes-mediated encephalitis is any other type of herpes-mediated encephalitis known in the art.

In another embodiment, the present invention provides a method of treating or reducing the incidence of a disease, disorder, or symptom associated with or secondary to an HSV-mediated encephalitis in a subject, the method comprising the step of administering to said subject a composition of the present invention.

In another embodiment, the present invention provides a method of treating, reducing the pathogenesis of, ameliorating the symptoms of, ameliorating the secondary symptoms of, reducing the incidence of, prolonging the latency to a relapse of an HSV infection in a subject, comprising the step of administering to the subject a composition of the present invention.

In another embodiment, the present invention provides a method of protecting a subject against formation of a zosteriform lesion or an analogous outbreak in a human subject. In another embodiment, the present invention provides a method of inhibiting the formation of an HSV zosteriform lesion or an analogous outbreak in a human subject.

"Zosteriform" refers, in one embodiment, to skin lesions characteristic of an HSV infection, particularly during reactivation infection, which, in one embodiment, begin as a rash and follow a distribution near dermatomes, commonly occurring in a strip or belt-like pattern. In one embodiment, the rash evolves into vesicles or small blisters filled with serous fluid. In one embodiment, zosteriform lesions form in mice as a result of contact with HSV. In another embodiment, zosteriform lesions form in humans as a result of contact with HSV. "Zosteriform spread" refers, in one embodiment, to an HSV infection that spreads from the ganglia to secondary skin sites within the dermatome. In another embodiment, the term refers to spread within the same dermatome as the initial site of infection. In another embodiment, the term refers to any other definition of "zosteriform spread" known in the art. "Outbreak", in another embodiment, refers to a sudden increase in symptoms of a disease or in the spread or prevalence of a disease, and in one embodiment, refers to a sudden increase in zosteriform lesions, while in another embodiment, "outbreak" refers to a sudden eruption of zosteriform lesions.

In one embodiment, the present invention provides a method of impeding the formation of a dermatome lesion or an analogous condition in a subject. In one embodiment, dermatome lesions form as a result of contact with HSV. In another embodiment, dermatome lesions most often develop when the virus reactivates from latency in the ganglia and in one embodiment, spreads down nerves, in one embodiment, causing a recurrent infection.

It is to be understood that the methods of the present invention may be used to treat, inhibit, suppress, etc an HSV infection or primary or secondary symptoms related to such an infection following exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in treating, inhibiting, suppressing, etc. an HSV infection or primary or secondary symptoms related to such an infection.

In one embodiment, "treating" refers to either therapeutic treatment or prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the compositions and methods of the present invention are effective in lowering HSV acquisition rates, duration of HSV infection, frequency of HSV reactivation, or a combination thereof. In another embodiment, the compositions and methods of the present invention are effective in treating or inhibiting genital ulcer disease, which in one embodiment, entails decreasing the severity or frequency of HSV genital ulcer disease. In one embodiment, the compositions and methods of the present invention block immune evasion from complement. In one embodiment, vaccination with mRNA-encoded HSV subunits may produce high titers of neutralizing antibodies or potent T-cell responses; however, upon subsequent infection, HSV immune evasion molecules may block the activities of antibodies or T cells, thereby reducing composition efficacy. In one embodiment, the compositions and methods of the present invention incorporate strategies to block virus mediated immune evasion by, in one embodiment, enhancing the effectiveness of e.g. a gD-1 subunit composition using gC-1 to prevent immune evasion from complement.

In one embodiment, studies in guinea pigs and mice suggest that viral load in ganglia correlates with the frequency of recurrent HSV infections. Thus, in one embodiment, the compositions and methods of the present invention are useful for preventing or inhibiting recurrent HSV infections. In one embodiment, antibodies to e.g. gC-1 block domains involved in immune evasion, which enhances complement activity, improves neutralizing activity of anti-gD-1 IgG, increases antibody- and complement-dependent cellular cytotoxicity, and augments complement-mediated neutralization and lysis of infected cells.

In one embodiment, symptoms are primary, while in another embodiment, symptoms are secondary. In one embodiment, "primary" refers to a symptom that is a direct result of the subject viral infection, while in one embodiment, "secondary" refers to a symptom that is derived from or consequent to a primary cause. In one embodiment, the compositions and strains for use in the present invention treat primary or secondary symptoms or secondary complications related to HSV infection.

In another embodiment, "symptoms" may be any manifestation of an HSV infection, comprising blisters, ulcerations, or lesions on the urethra, cervix, upper thigh, and/or anus in women and on the penis, urethra, scrotum, upper thigh, and anus in men, inflammation, swelling, fever, flu-like symptoms, sore mouth, sore throat, pharyngitis, pain, blisters on tongue, mouth or lips, ulcers, cold sores, neck pain, enlarged lymph nodes, reddening, bleeding, itching, dysuria, headache, muscle pain, etc., or a combination thereof.

In another embodiment, the disease, disorder, or symptom is fever. In another embodiment, the disease, disorder, or symptom is headache. In another embodiment, the disease, disorder, or symptom is stiff neck. In another embodiment, the disease, disorder, or symptom is seizures. In another embodiment, the disease, disorder, or symptom is partial paralysis. In another embodiment, the disease, disorder, or symptom is stupor. In another embodiment, the disease, disorder, or symptom is coma. In another embodiment, the disease, disorder, or symptom is any other disease, disorder, or symptom known in the art that is associated with or secondary to a herpes-mediated encephalitis.

Methods of determining the presence and severity of herpes-mediated encephalitis are well known in the art, and are described, for example, in Bonkowsky J L et al. (Herpes simplex virus central nervous system relapse during treatment of infantile spasms with corticotropin. Pediatrics. 2006 May; 117(5):e1045-8) and Khan O A, et al. (Herpes encephalitis presenting as mild aphasia: case report. BMC Fam Pract. 2006 Mar. 24; 7:22). Each method represents a separate embodiment of the present invention.

In another embodiment, the present invention provides a method of treating or reducing the incidence of a disease, disorder, or symptom associated with an HSV infection in a subject, the method comprising the step of administering to said subject a composition of the present invention.

In another embodiment, the disease, disorder, or symptom secondary to an HSV infection is oral lesions. In another embodiment, the disease, disorder, or symptom is genital lesions. In another embodiment, the disease, disorder, or symptom is oral ulcers. In another embodiment, the disease, disorder, or symptom is genital ulcers. In another embodiment, the disease, disorder, or symptom is fever. In another embodiment, the disease, disorder, or symptom is headache. In another embodiment, the disease, disorder, or symptom is muscle ache. In another embodiment, the disease, disorder, or symptom is swollen glands in the groin area. In another embodiment, the disease, disorder, or symptom is painful urination. In another embodiment, the disease, disorder, or symptom is vaginal discharge. In another embodiment, the disease, disorder, or symptom is blistering. In another embodiment, the disease, disorder, or symptom is flu-like malaise. In another embodiment, the disease, disorder, or symptom is keratitis. In another embodiment, the disease, disorder, or symptom is herpetic whitlow. In another embodiment, the disease, disorder, or symptom is Bell's palsy. In another embodiment, the disease, disorder, or symptom is herpetic erythema multiforme. In another embodiment, the disease, disorder, or symptom is a lower back symptom (e.g. numbness, tingling of the buttocks or the area around the anus, urinary retention, constipation, and impotence). In another embodiment, the disease, disorder, or symptom is a localized eczema herpeticum. In another embodiment, the disease, disorder, or symptom is a disseminated eczema herpeticum. In another embodiment, the disease, disorder, or symptom is a herpes gladiatorum. In another embodiment, the disease, disorder, or symptom is a herpetic sycosis. In another embodiment, the disease, disorder, or symptom is an esophageal symptom (e.g. difficulty swallowing or burning, squeezing throat pain while swallowing, weight loss, pain in or behind the upper chest while swallowing). In another embodiment, the disease, disorder, or symptom is any other disease, disorder, or symptom that is known in the art. Each disease, disorder, and symptom represents a separate embodiment of the present invention.

Thus, in one embodiment, the compositions and methods of the instant invention treat, suppress, inhibit, or reduce the incidence of the infection itself, while in another embodiment, the compositions and methods of the instant invention treat, suppress, inhibit, or reduce the incidence of primary symptoms of the infection, while in another embodiment, the compositions and methods of the instant invention treat, suppress, inhibit, or reduce the incidence of secondary symptoms of the infection. It is to be understood that the compositions and methods of the instant invention may affect any combination of the infection, the primary symptoms caused by the infection, and secondary symptoms related to the infection.

The HSV infection that is treated or ameliorated by methods and compositions of the present invention is, in another embodiment, a genital HSV infection. In another embodiment, the HSV infection is an oral HSV infection. In another embodiment, the HSV infection is an ocular HSV infection. In another embodiment, the HSV infection is a dermatologic HSV infection.

In another embodiment, the present invention provides a method of reducing the incidence of a disseminated HSV infection in a subject, the method comprising the step of administering to said subject a composition of the present invention.

In another embodiment, the present invention provides a method of reducing the incidence of a neonatal HSV infection in an offspring of a subject, the method comprising the step of administering to said subject a composition of the present invention.

In another embodiment, the present invention provides a method of reducing a transmission of an HSV infection from a subject to an offspring thereof, the method comprising the step of administering to said subject a composition of the present invention.

In another embodiment, the offspring is an infant. In another embodiment, the transmission that is reduced or inhibited is transmission during birth. In another embodiment, transmission during breastfeeding is reduced or inhibited. In another embodiment, the transmission that is reduced or inhibited is any other type of parent-to-offspring transmission known in the art.

In another embodiment, the present invention provides a method of reducing a severity of a neonatal HSV infection in an offspring of a subject, the method comprising the step of administering to said subject a composition of the present invention.

In one embodiment, the present invention provides a method of treating, suppressing, inhibiting, or reducing the incidence of an HSV infection in a subject infected with HIV, the method comprising the step of administering to said subject a composition comprising: (a) a modified mRNA encoding HSV gC protein or fragment thereof; (b) a modified mRNA encoding HSV gE protein or fragment thereof, and (c) an adjuvant. In another embodiment, the present invention provides a method of treating, suppressing, inhibiting, or reducing the incidence of an HSV infection in a subject infected with HIV, the method comprising the step of administering to said subject a composition comprising: (a) a modified mRNA encoding HSV gC protein or fragment thereof, wherein said fragment comprises either a C3b-binding domain thereof, a properdin interfering domain thereof, a C5 interfering domain thereof, or a fragment of said C3b-binding domain, properdin interfering domain, or C5-interfering domain; (b) a modified mRNA encoding HSV gE protein or fragment thereof, wherein said fragment comprises AA 24-409 or a fragment thereof, and (c) an adjuvant.

In another embodiment, the present invention provides a method of treating an HSV infection in a subject infected with HIV, the method comprising the step of administering to said subject a composition of the present invention. In another embodiment, the present invention provides a method of suppressing an HSV infection in a subject infected with HIV, the method comprising the step of administering to said subject a composition of the present invention. In another embodiment, the present invention provides a method of inhibiting an HSV infection in a subject infected with HIV, the method comprising the step of administering to said subject a composition of the present invention. In another embodiment, the present invention provides a method of reducing the incidence of an HSV infection in a subject infected with HIV, the method comprising the step of administering to said subject a composition of the present invention. In another embodiment, the present invention provides a method of preventing an HIV infection, the method comprising the step of administering to said subject an HSV composition of the present invention. In one embodiment, HSV infection increases the risk of HIV infection, and protection against HSV infection decreases the risk of HIV infection. Thus, in one embodiment, the present invention provides a method of decreasing the risk of an HIV infection, the method comprising the step of administering to said subject a composition of the present invention.

In one embodiment, the composition for use in the methods of the present invention elicits an immune response against HSV. In another embodiment, the composition for use in the methods of the present invention elicits an immune response against HSV-1. In another embodiment, the composition for use in the methods of the present invention elicits an immune response against HSV-2. In another embodiment, the composition comprises modified mRNAs encoding gD and gC proteins. In another embodiment, the composition comprises modified mRNAs encoding gE and gD proteins. In another embodiment, the composition comprises modified mRNAs encoding gC and gE proteins. In another embodiment, the composition comprises modified mRNAs encoding gE, gD, and gC proteins. In another embodiment, the composition comprises modified mRNAs encoding gE, gD, or gC protein. In another embodiment, the proteins encoded by the modified mRNAs are HSV-1 proteins. In another embodiment, the proteins encoded by the modified mRNAs are HSV-2 proteins. In another embodiment, the proteins encoded by the modified mRNAs comprise both HSV-1 and HSV-2 proteins.

It is to be understood that, in one embodiment, a subject according to any of the embodiments described herein may be a subject infected with, or in another embodiment, susceptible to infection with HSV. In one embodiment, a subject may be infected with, or in another embodiment, susceptible to infection with at least one other pathogen. In one embodiment, a subject may be immunocompromised. In one embodiment, the subject is infected by HSV, while in another embodiment, the subject is at risk for infection by HSV, which in one embodiment, is a subject who is a neonate, in another embodiment, immunocompromised, in another embodiment, elderly, and in another embodiment, an immunocompromised neonate or an immunocompromised elderly subject.

In another embodiment, the compositions of the present invention and their related uses may suppress, inhibit, prevent or treat an HIV infection in a subject. In one embodiment, the compositions of the present invention and their related uses may treat secondary complications of HIV infection, which in one embodiment, are opportunistic infections, neoplasms, neurologic abnormalities, or progressive immunologic deterioration. In another embodiment, the methods comprise treating acquired immunodeficiency syndrome (AIDS). In another embodiment, the methods comprise treating a decline in the number of $CD4^+$ T lymphocytes.

In another embodiment, the present invention provides a method of reducing HIV-1 transmission to an offspring, the method comprising the step of administering to a subject a composition of the present invention. As is known in the art, HSV-2 infection increases HIV-1 viral shedding in genital secretions (Nagot N et al., Reduction of HIV-1 RNA levels with therapy to suppress herpes simplex virus. N Engl J Med. 2007 Feb. 22; 356(8):790-9). Thus, methods of the present invention of inhibiting HSV-2 infection are also efficacious for reducing HIV-1 transmission to an offspring. In another embodiment, the mutant HSV strain is an HSV-1 strain. In another embodiment, the mutant HSV strain is an HSV-2 strain.

In another embodiment, the present invention provides a method of reducing HIV-1 transmission to a sexual partner, the method comprising the step of administering to a subject a composition of the present invention. As is known in the art, HSV-2 infection increases HIV-1 viral shedding in genital secretions. Thus, methods of the present invention of inhibiting HSV-2 infection are also efficacious for reducing HIV-1 transmission to a sexual partner. In another embodiment, the mutant HSV strain is an HSV-1 strain. In another embodiment, the mutant HSV strain is an HSV-2 strain.

In another embodiment, the present invention provides a method of reducing susceptibility to HIV-1, the method comprising the step of administering to a subject a composition of the present invention. As is known in the art, HSV-2 infection increases HIV-1 replication (Ouedraogo A et al., Impact of suppressive herpes therapy on genital HIV-1 RNA among women taking antiretroviral therapy: a randomized controlled trial. AIDS. 2006 Nov. 28; 20(18):2305-13). Thus, methods of the present invention of inhibiting HSV-2 infection are also efficacious for reducing susceptibility to HIV-1. In another embodiment, the mutant HSV strain is an HSV-1 strain. In another embodiment, the mutant HSV strain is an HSV-2 strain.

Thus, in one embodiment, the present invention provides a method of inhibiting a primary HSV infection in an HIV-infected subject, comprising the step of administering to said subject a composition of the present invention. In another embodiment, the present invention provides a method of treating or reducing the incidence of an HSV infection in an HIV-infected subject, comprising the step of administering to said subject a composition of the present invention. In another embodiment, the present invention provides a method of inhibiting a flare, recurrence, or HSV labialis following a primary HSV infection in an HIV-infected subject, the method comprising the step of administering to said subject a composition of the present invention. In one embodiment, administration of a composition of the present invention an anti-HSV immune response.

In another embodiment, the present invention provides a method for inducing an immune response in a subject, the method comprising the step of administering to said subject a nucleoside modified mRNA composition of the present invention. In another embodiment, the immune response comprises a CD4 immune response. In another embodiment, the immune response comprises a CD8 immune response. In another embodiment, the immune response comprises a T follicular helper cell immune response. In another embodiment, the immune response comprises a germinal center B cell immune response. In another embodiment, the immune response comprises an IgG antibody response to gC2, gD2, gE2 or a combination thereof.

In another embodiment, the present invention provides a method of treating a Herpes Simplex Virus (HSV) infection in a subject, the method comprising the step of intramuscularly administering to said subject a nucleoside modified mRNA composition of the present invention. In another embodiment, the invention provides a method of suppressing, inhibiting, or reducing the incidence of a Herpes Simplex Virus (HSV) infection in a subject, the method comprising the step of intramuscularly administering to said subject a nucleoside modified mRNA composition of the present invention.

Administration and Pharmaceutical Regimens

Compositions of the present invention can be, in another embodiment, administered to a subject by any method known to a person skilled in the art, such as parenterally, paracancerally, transmucosally, transdermally, intramuscularly, intravenously, intra-dermally, subcutaneously, intraperitonealy, intra-ventricularly, intra-cranially, intra-vaginally, intra-nasally, intra-tumorally, or topically.

"Administering," in another embodiment, refers to directly introducing into a subject by injection or other means a composition of the present invention. In another embodiment, "administering" refers to contacting a cell of the subject's immune system with a composition or modified mRNA encoding HSV protein or mixture thereof.

In another embodiment of the methods and compositions of the present invention, the compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In other embodiments, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intramuscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier.

In another embodiment, the composition is administered as a suppository, for example a rectal suppository or a urethral suppository. In another embodiment, the pharmaceutical composition is administered by subcutaneous implantation of a pellet. In another embodiment, the pellet provides for controlled release of agent over a period of time.

In a preferred embodiment, pharmaceutical compositions are administered intramuscularly, subcutaneously or intradermally.

"Effective dosage" of the modified mRNA, refers, in another embodiment, to an amount sufficient to exert a therapeutic effect. In another embodiment, the term refers to an amount sufficient to elicit expression of a detectable amount of the encoded protein. Each possibility represents a separate embodiment of the present invention.

Methods for measuring the dose of a modified mRNA encoding an HSV glycoprotein (e.g. in human subjects) are well known in the art, and include, for example, dose-escalating trials. Each method represents a separate embodiment of the present invention.

In some embodiments, any of the HSV compositions of and for use in the methods of this invention will comprise a modified mRNA encoding HSV protein or combination of modified mRNAs encoding HSV proteins of the present invention, in any form or embodiment as described herein. In some embodiments, any of the compositions of and for use in the methods will consist of a modified mRNA encoding HSV protein or combination of modified mRNA encodings HSV proteins of the present invention, in any form or embodiment as described herein. In some embodiments, the compositions of this invention will consist essentially of a modified mRNA encoding an HSV protein or combination of modified mRNAs encoding HSV proteins of the present invention, in any form or embodiment as described herein. In some embodiments, the term "comprise" refers to the inclusion of modified mRNA encoding other HSV proteins, as well as inclusion of modified mRNA encoding other proteins that may be known in the art. In some embodiments, the term "consisting essentially of" refers to a composition, which has the modified mRNA encoding a specific HSV protein or fragment thereof. However, other components may be included that are not involved directly in the utility of the modified mRNA(s) encoding HSV protein(s). In some embodiments, the term "consisting" refers to a composition having a modified mRNA encoding particular HSV protein or fragment or combination of modified mRNAs encoding HSV proteins or fragments of the present invention, in any form or embodiment as described herein.

In another embodiment, the present invention provides a composition for treating HSV-1 or a symptom or manifestation thereof, the composition comprising a modified mRNA of the present invention.

In another embodiment, the present invention provides a composition for treating HSV-2 or a symptom or manifestation thereof, the composition comprising a modified mRNA of the present invention.

It is to be understood that the compositions, and methods of the present invention may be used in non-HSV herpesvirus as well, which in one embodiment, proteins gD, gE, or gC proteins that are, in one embodiment, 70% homologous, in another embodiment, 80% homologous, in another embodiment, 85% homologous, in another embodiment, 90% homologous, in another embodiment, 95% homologous, in another embodiment, 98% homologous, and in another embodiment, 100% homologous to the gD, gE, or gC proteins of HSV-1, or in another embodiment, of HSV-2. In one embodiment, such compositions may be useful in suppressing, inhibiting, preventing, or treating, cancers, or in another embodiment, tumors. In one embodiment, non-HSV herpesvirus comprise Varicella Zoster Virus (VZV), Epstein-Barr virus (EBV), EBNA, cytomegalovirus (CMV), and human herpesvirus-6 (HHV-6).

In another embodiment, of methods of the present invention, a composition of the present invention is administered once. In another embodiment, the composition is administered twice. In another embodiment, the composition is administered three times. In another embodiment, the composition is administered four times. In another embodiment, the composition is administered at least four times. In another embodiment, the composition is administered more than four times.

In another embodiment, the dosage is a daily dose. In another embodiment, the dosage is a weekly dose. In another embodiment, the dosage is a monthly dose. In another embodiment, the dosage is an annual dose. In another embodiment, the dose is one is a series of a defined number of doses. In another embodiment, the dose is a one-time dose.

In one embodiment, any of the booster doses described hereinabove is administered following a priming dose comprising one or modified more mRNAs encoding HSV-1 proteins or immunogenic fragments thereof. In another embodiment, any of the booster doses described hereinabove is administered following a priming vaccination comprising one or more modified more mRNAs encoding HSV-2 proteins or immunogenic fragments thereof.

In one embodiment, a subject is immunized with a single administration of the composition. In another embodiment, a subject is immunized with a single dose. In another embodiment, a subject is immunized with two doses. In another embodiment, a subject is immunized with three doses. In another embodiment, a subject is immunized with four doses. In another embodiment, a subject is immunized with five doses.

In one embodiment, all the components of the composition are provided in equal concentrations. According to this aspect and in one embodiment, modified mRNAs encoding gC, gD, and gE are provided in a ratio of 1:1:1. In another embodiment, modified mRNAs encoding gC, gD, and gE are provided in a ratio of 5:2:5. In another embodiment, modified mRNAs encoding gC and gD are provided in a ratio of 1:1. In another embodiment, modified mRNAs encoding gC and gE are provided in a ratio of 1:1. In another embodiment, modified mRNAs encoding gD and gE are provided in a ratio of 1:1.

In one embodiment, modified mRNAs encoding gC, gD, gE, or a combination thereof, or combined with other HSV glycoproteins, are administered in a single composition at the same site and by the same route, while in another embodiment, modified mRNAs encoding gC, gD, and gE are administered in separate compositions at separate sites but by the same route of administration, or in another embodiment, modified mRNAs encoding gC, gD, and gE are administered in separate compositions at separate sites and by different routes of administration, or in another embodiment, modified mRNAs encoding gC, gD, and gE are administered in separate compositions at the same site and by different routes of administration (e.g. injection and topical).

In one embodiment, the methods of the present invention include a one-time or single administration of compositions comprising one or more nucleoside modified mRNAs of the present invention. In another embodiment, the methods of the present invention include administration of compositions comprising one or more nucleoside modified mRNAs in a prime and boost approach. In one embodiment, the methods of the present invention further comprise the step of administering to said subject one or more additional administrations of said nucleoside modified mRNA composition subsequent to the first administration.

In another embodiment, the methods of the present invention comprise administering a composition comprising one or more nucleoside modified mRNAs encoding one or more HSV glycoproteins as a first administration and a composition comprising one or more HSV glycoproteins as a second or subsequent administration. In one embodiment, the HSV glycoproteins encoded by the mRNA in the first (or prime) administration are the same glycoproteins in the second or subsequent (or boost) administration. In another embodiment, a composition comprising one or more HSV glycoproteins is administered as a first administration, and a composition comprising one or more nucleoside modified mRNAs encoding one or more HSV glycoproteins is administered as a second or subsequent administration. Each possibility represents a separate embodiment of the present invention.

In another embodiment, modified mRNAs encoding gC, gD, and gE are administered simultaneously followed by a booster dose of modified mRNA encoding gD without modified mRNAs encoding gC or gE. In another embodiment, modified mRNAs encoding gC, gD, and gE are administered simultaneously followed by a booster dose of modified mRNA encoding gC without modified mRNAs encoding gD or gE. In another embodiment, modified mRNAs encoding gC, gD, and gE are administered simultaneously followed by a booster dose of modified mRNA encoding gE without modified mRNAs encoding gD or gC. In another embodiment, modified mRNAs encoding gC, gD, and gE are administered simultaneously followed by a booster dose of modified mRNAs encoding gC and gD without modified mRNAs encoding gE. In another embodiment, modified mRNAs encoding gC, gD, and gE are administered simultaneously followed by a booster dose of modified mRNAs encoding gC and gE without modified mRNAs encoding gD. In another embodiment, modified mRNAs encoding gC, gD, and gE are administered simultaneously followed by a booster dose of modified mRNAs encoding gD and gE without modified mRNAs encoding gE. In one embodiment the booster administration is performed at the same site and by the same mode of administration as the priming administration. In another embodiment, the booster administration is performed at a different site from the priming administration but by the same mode of administration as the priming administration. In one embodiment the booster administration is performed at the same site but by different mode of administration than priming administration. In another embodiment, the booster administration is performed at a different site and by different mode of administration than priming administration.

In one embodiment, the modified mRNA induces a detectably lower innate immune response than the same quantity of unmodified RNA having the same sequence.

In one embodiment, the effectiveness of the compositions and methods of the present invention are dependent on the presence of complement, while in another embodiment, the compositions and methods of the present invention are not dependent on the presence of complement. In one embodiment, the effectiveness of some of the compositions for use in the methods of the present invention are dependent on the presence of complement, while others are not. In one embodiment, the anti-gC antibody is dependent on complement for its effectiveness against HSV.

In one embodiment, complement is an important contributor to innate and acquired immunity. In one embodiment, complement activation facilitates virus neutralization by particle phagocytosis and lysis, functions as a chemoattractant for neutrophils and macrophages, and enhances B and T cell responses. In one embodiment, HSV-1 gC binds complement C3b and blocks C5 and properdin interaction with C3b, which inhibit complement activation and complement-mediated virus neutralization. In one embodiment, a gC-1 domain that interacts with complement is located within amino acids 33 to 133 and blocks C5 and properdin binding to C3b, and in one embodiment, a gC-1 domain that interacts with complement extends from amino acids 124 to 366 and directly binds C3b. In one embodiment, an HSV-1 gC mutant virus deleted in the C3b binding domain is more susceptible to complement-mediated virus neutralization in vitro and less virulent than wild-type (WT) virus in the mouse flank model. Therefore, in one embodiment, the interaction between gC-1 and C3b enhances HSV-1 virulence, and in one embodiment, blocking the gC-1 domain is effective in preventing or treating HSV-1 infection.

In one embodiment, the compositions and methods of the present invention are for use in human subjects, while in another embodiment, they are for use in animal subjects. In another embodiment, the subject is mammalian. In another embodiment, the subject is any organism susceptible to infection by HSV. In one embodiment, the subject is murine, bovine, ovine, canine, feline, equine, porcine, etc. In one embodiment, the compositions and methods of the present invention are effective in male subjects. In another embodiment, the compositions and methods of the present invention are effective in female subjects. In one embodiment, the compositions and methods of the present invention are effective in seronegative subjects. In another embodiment, the compositions and methods of the present invention are effective in seropositive subjects.

Pharmaceutical Formulations

In one embodiment, a method of present invention further comprises mixing the modified mRNA with a transfection reagent prior to the step of contacting. In another embodiment, a method of present invention further comprises administering the modified mRNA together with the transfection reagent. In another embodiment, the transfection reagent is a cationic lipid reagent.

In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin® or Lipofectamine®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity.

In another embodiment, liposomes are hollow spherical vesicles composed of lipids arranged in a similar fashion as those lipids which make up the cell membrane. They have, in another embodiment, an internal aqueous space for entrapping water soluble compounds and range in size from 0.05 to several microns in diameter. In another embodiment, liposomes can deliver RNA to cells in a biologically active form (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

Each type of transfection reagent represents a separate embodiment of the present invention.

In another embodiment, a modified mRNA of the present invention is encapsulated in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly(d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171.1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707.2005); and Zimmermann E et al, Electrolyte- and pH-stabilities of aqueous solid lipid nanoparticle (SLN) dispersions in artificial gastrointestinal media. Eur J Pharm Biopharm 52:203. 2001). Each method represents a separate embodiment of the invention.

In one embodiment, ψmRNA is encapsulated in nanoparticles to improve efficiency of delivery and expression of ψmRNA. Nanoparticle packaging involves condensing and encapsulating RNA into particles that are smaller than the pore of the nuclear membrane, using chemicals including poly-L-lysine and polyethylene glycol. In one embodiment, RNA is packaged into one of four nanoparticle formulations (PEI, PLL, PAE, and $CK_{30}PEG_{10k}$).

Lipid Nanoparticles

In one embodiment, nanoparticles used in the compositions and methods of the present invention comprise lipid nanoparticles as described in Cullis, P., & Hope, M. (n.d.). Lipid Nanoparticle Systems for Enabling Gene Therapies. Molecular therapy., 25(7), which is incorporated by reference herein in its entirety.

In one embodiment, delivery of nucleoside-modified RNA comprises any suitable delivery method, including exemplary RNA transfection methods described elsewhere herein. In certain embodiments, delivery of a nucleoside-modified RNA to a subject comprises mixing the nucleoside-modified RNA with a transfection reagent prior to the step of contacting. In another embodiment, a method of present invention further comprises administering nucleoside-modified RNA together with the transfection reagent. In another embodiment, the transfection reagent is a cationic lipid reagent.

In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin®, Lipofectamine®, or TransIT®. In another embodiment, the transfection reagent is any other transfection reagent known in the art.

In another embodiment, the transfection reagent forms a liposome.

Liposomes, in another embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In one embodiment, the composition comprises a lipid nanoparticle (LNP) and one or more nucleic acid molecules described herein. For example, in one embodiment, the composition comprises an LNP and one or more nucleoside-modified RNA molecules encoding one or more antigens, adjuvants, or a combination thereof.

The term "lipid nanoparticle" refers to a particle having at least one dimension on the order of nanometers (e.g., 1-1,000 nm) which includes one or more lipids, for example a lipid of Formula (I), (II) or (III), as described in WO2016176330A1, which is incorporated by reference herein in its entirety.

In some embodiments, lipid nanoparticles are included in a formulation comprising a nucleoside-modified RNA as described herein. In some embodiments, such lipid nanoparticles comprise a cationic lipid and one or more excipient selected from neutral lipids, charged lipids, steroids and polymer conjugated lipids (e.g., a pegylated lipid such as a pegylated lipid of structure (IV), such as compound IVa). In some embodiments, the nucleoside-modified RNA is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, the nucleoside-modified RNA, when present in the lipid nanoparticles, is resistant in aqueous solution to degradation with a nuclease.

The LNP may comprise any lipid capable of forming a particle to which the one or more nucleic acid molecules are attached, or in which the one or more nucleic acid molecules are encapsulated. The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the LNP comprises one or more cationic lipids, and one or more stabilizing lipids. Stabilizing lipids include neutral lipids and pegylated lipids.

In one embodiment, the LNP comprises a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

In certain embodiments, the cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N (N',N'-dimethylaminoethane)-carbamoyl)cholesterol (DC-Choi), N-(1-(2,3-dioleoyloxy)propyl)-N-2-(sperminecarboxamido)ethyl)-N, N-dimethylammonium trifluoracetate (DOSPA), dioctadecylamidoglycyl carboxy spermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH:

DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Suitable amino lipids useful in the invention include those described in WO 2012/016184, incorporated herein by reference in its entirety. Representative amino lipids include, but are not limited to, 1,2-dilinoleyoxy-3-(dimethylamino) acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

In certain embodiments, the cationic lipid is present in the LNP in an amount from about 30 to about 95 mole percent.

In one embodiment, the cationic lipid is present in the LNP in an amount from about 30 to about 70 mole percent. In one embodiment, the cationic lipid is present in the LNP in an amount from about 40 to about 60 mole percent. In one embodiment, the cationic lipid is present in the LNP in an amount of about 50 mole percent. In one embodiment, the LNP comprises only cationic lipids. In certain embodiments, the L P comprises one or more additional lipids which stabilize the formation of particles during their formation.

Suitable stabilizing lipids include neutral lipids and anionic lipids.

The term "neutral lipid" refers to any one of a number of lipid species that exist in either an uncharged or neutral zwitterionic form at physiological pH.

Representative neutral lipids include diacylphosphatidylcholines, diacylphosphatidylethanolamines, ceramides, sphingomyelins, dihydro sphingomyelins, cephalins, and cerebrosides.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-l-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid (e.g., lipid of Formula (I)) to the neutral lipid ranges from about 2:1 to about 8:1.

In various embodiments, the LNPs further comprise a steroid or steroid analogue.

In certain embodiments, the steroid or steroid analogue is cholesterol. In some of these embodiments, the molar ratio of the cationic lipid (e.g., lipid of Formula (I)) to cholesterol ranges from about 2:1 to 1:1.

The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

In certain embodiments, the LNP comprises glycolipids (e.g., monosialoganglioside GMi). In certain embodiments, the LNP comprises a sterol, such as cholesterol.

In some embodiments, the LNPs comprise a polymer conjugated lipid. The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-s-DMG) and the like.

In certain embodiments, the LNP comprises an additional, stabilizing-lipid which is a polyethylene glycol-lipid (pegylated lipid). Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols.

Representative polyethylene glycol-lipids include PEG-c-DOMG, PEG-c-DMA, and PEG-s-DMG. In one embodiment, the polyethylene glycol-lipid is N-[(methoxy poly (ethylene glycol)$_2$ooo)carbamyl]-1,2-dimyristyloxlpropyl-3-amine (PEG-c-DMA). In one embodiment, the polyethylene glycol-lipid is PEG-c-DOMG). In other embodiments, the LNPs comprise a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-0-(2',3'-di(tetradecanoyloxy)propyl-1-0-(co-methoxy(polyethoxy) ethyl)butanedioate (PEG-S-DMG), a pegylated ceramide (PEG-cer), or a PEG dialkoxypropylcarbamate such as Q-methoxy(polyethoxy)ethyl-N-(2,3-di(tetradecanoxy)propyl)carbamate or 2,3-di(tetradecanoxy)propyl-N-(co-methoxy(polyethoxy)ethyl)carbamate. In various embodiments, the molar ratio of the cationic lipid to the pegylated lipid ranges from about 100:1 to about 25:1.

In certain embodiments, the additional lipid is present in the LNP in an amount from about 1 to about 10 mole percent. In one embodiment, the additional lipid is present in the LNP in an amount from about 1 to about 5 mole percent. In one embodiment, the additional lipid is present in the LNP in about 1 mole percent or about 1.5 mole percent.

In certain embodiments, the LNP comprises one or more targeting moieties which are capable of targeting the LNP to a cell or cell population. For example, in one embodiment, the targeting moiety is a ligand which directs the LNP to a receptor found on a cell surface.

In certain embodiments, the LNP comprises one or more internalization domains. For example, in one embodiment, the LNP comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

Other exemplary LNPs and their manufacture are described in the art, for example in WO2016176330A1, U.S. Patent Application Publication No. US20120276209, Semple et al., 2010, Nat Biotechnol., 28(2): 172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tarn et al., 2013, Nanomedicine, 9(5): 665-74, each of which are incorporated by reference in their entirety.

In another embodiment, methods of the present invention comprise administering a modified mRNAs encoding HSV glycoprotein and a pharmaceutically acceptable carrier or diluent. In other embodiments, pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

As used herein "pharmaceutically acceptable carriers or diluents" are well known to those skilled in the art.

In another embodiment, the pharmaceutical compositions provided herein are controlled-release compositions, i.e. compositions in which the compound is released over a period of time after administration. Controlled- or sustained-release compositions include formulation in lipophilic depots (e.g. fatty acids, waxes, oils). In another embodiment, the composition is an immediate-release composition, i.e. a composition in which the entire compound is released immediately after administration.

Each of the additives, excipients, formulations and methods of administration represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

The following examples are presented in order to more fully illustrate the preferred embodiments of the invention. They should in no way be construed, however, as limiting the broad scope of the invention.

EXPERIMENTAL DETAILS SECTION

Example 1: Materials and Experimental Methods

Modified mRNA expressing HSV-2 glycoproteins C, D and E (gC2/gD2/gE2) ectodomains. Modified mRNA (encoding gC2 (SEQ ID NO: 10), encoding gD2 (SEQ ID NO: 4), and encoding gE2 (SEQ ID NO: 16)) was prepared based on the DNA coding sequences that encode HSV-2 glycoprotein C (gC2) amino acids 27-426 from HSV-2 strain 333 (SEQ ID NO: 11), glycoprotein D (gD2) amino acids 26-331 from HSV-2 strain 333 (SEQ ID NO: 5), and glycoprotein E (gE2) amino acids 24-405 from HSV-2 strain 2.12 (SEQ ID NO: 17).

The modified mRNA was incorporated into liposomal nanoparticles (LNP) by Acuitas Therapeutics to prepare the following immunogens: (a) Poly C mRNA in LNP; (b) gC2 modified mRNA in LNP; (c) gD2 modified mRNA in LNP; (d) gE2 modified mRNA in LNP; (e) gC2 & gD2 & gE2 modified mRNA in LNP.

Immunization groups were as follows:

a) Controls (Poly C group): 10 μg Poly C mRNA/LNP divided into 4 aliquots and administered at 4 separate sites.
b) gD2 alone (gD2 group): 10 μg gD2 mRNA/LNP divided into 4 aliquots and administered at 4 separate sites.
c) Individual trivalent (Trivalent-I group): 10 μg gC2 mRNA/LNP, 10 μg gD2 mRNA/LNP, 10 μg gE2 mRNA/LNP each divided into 2 aliquots and each given at 2 sites.
d) Combined trivalent (Trivalent-C group): 10 μg gC2 mRNA & 10 μg gD2 mRNA & 10 μg gE2 mRNA combined into LNP and divided into 4 aliquots and given at 4 sites.

Experimental Procedures. Hair was removed from the back of 6-8 week old BALB/c mice using an electric razor and Nair. Mice were bled prior to the first and second immunization and prior to intravaginal challenge. Two immunizations were performed intradermally at 28-day intervals. Intradermal immunizations were performed on the denuded backs. Five mice that received the trivalent vaccine at individual sites (group c above) were sacrificed 14 days after the second immunization. Spleens were harvested for $CD4^+$ and $CD8^+$ T cell responses to gC2, gD2 and gE2 subunit antigens or to 15 amino acid peptides each with 11 overlapping amino acids. Twenty-eight days after the second immunization, mice were treated subcutaneously with 2 mg Depo-Provera and 5 days later infected intravaginally with $5\times10^3$ PFU HSV-2 strain MS (~400 $LD_{50}$). On days 2 and 4 post-challenge, vaginal swabs were obtained for virus cultures. On day 4 post-challenge, some mice in each vaccine group were sacrificed and dorsal root ganglia (DRG) excised for HSV-2 DNA qPCR. The remaining animals were evaluated for weight loss and hind limb weakness for 10 days while survival and genital disease were monitored for 28 days.

Figures 1A, 1B, 1C:
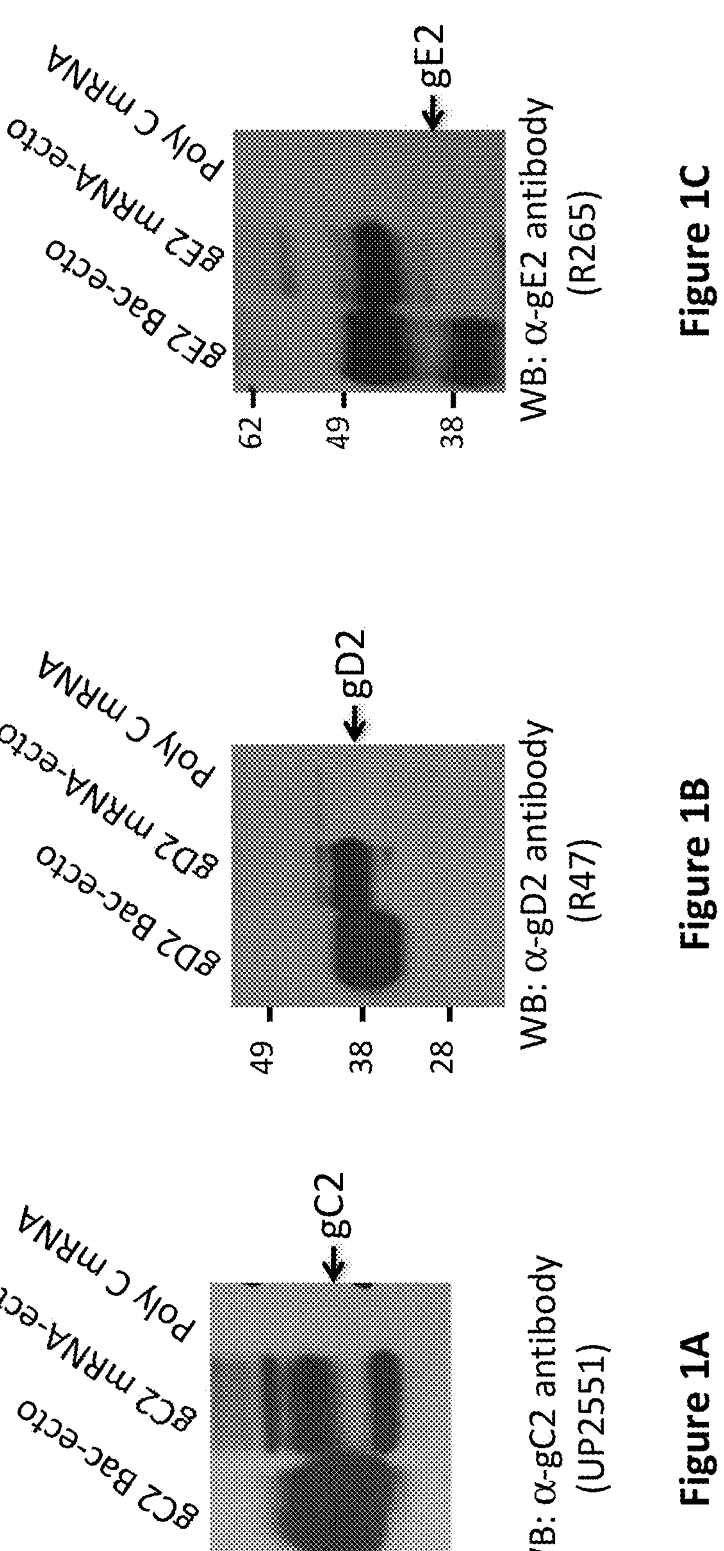
FIGS. 1A-1C. Characterization of the translational product of the ectodomain of gC2-, gD2- and gE2-modified mRNA in Vero cells.

Example 2: Characterization of Translational Products Produced by gC2, gD2, and gE2 Modified mRNA The ability of modified mRNA to express proteins of the expected molecular weight when transfected into mammalian cells was verified. 0.1 μg of gC2-, gD2-, or gE2-modified mRNA was transfected into 293T cells using TransIT-mRNA (Mirus Bio LLC) for the transfection. Eighteen hours later, cells were harvested and extracts prepared for Western blots. The mRNAs were designed to express the ectodomains of gC2, gD2 and gE2 (labeled mRNA-ecto). As controls for the expected molecular weights, purified baculovirus proteins gC2, gD2, and gE2 expressing the same amino acids as the mRNA constructs (labeled Bac-ecto) were used (FIGS. 1A-C).

Conclusion: When transfected into mammalian cells, modified mRNA encoding the ectodomains of HSV-2 gC2 (FIG. 1A), gD2 (FIG. 1B) and gE2 (FIG. 1C) produced proteins of the appropriate molecular weights that reacted with antibodies to the glycoproteins on Western blot.

Example 3: ELISA Antibody Responses in Subjects Immunized with gD2 or Trivalent Modified mRNA Vaccines ELISA endpoint titers were evaluated on sera taken 28 days after the first and second immunizations. Immunization groups were as follows: Poly C (10 μg Poly C mRNA/LNP divided into 4 aliquots and administered at 4 separate sites) (control); gD2 (10 μg gD2 mRNA/LNP divided into 4 aliquots and administered at 4 separate sites); Trivalent-I (10 μg gC2 mRNA/LNP, 10 μg gD2 mRNA/LNP, 10 μg gE2 mRNA/LNP each divided into 2 aliquots and each given at 2 sites); and Trivalent-C(10 μg gC2 mRNA & 10 μg gD2 mRNA & 10 μg gE2 mRNA combined into LNP and divided into 4 aliquots and given at 4 sites).

Figures 2A, 2B, 2C:
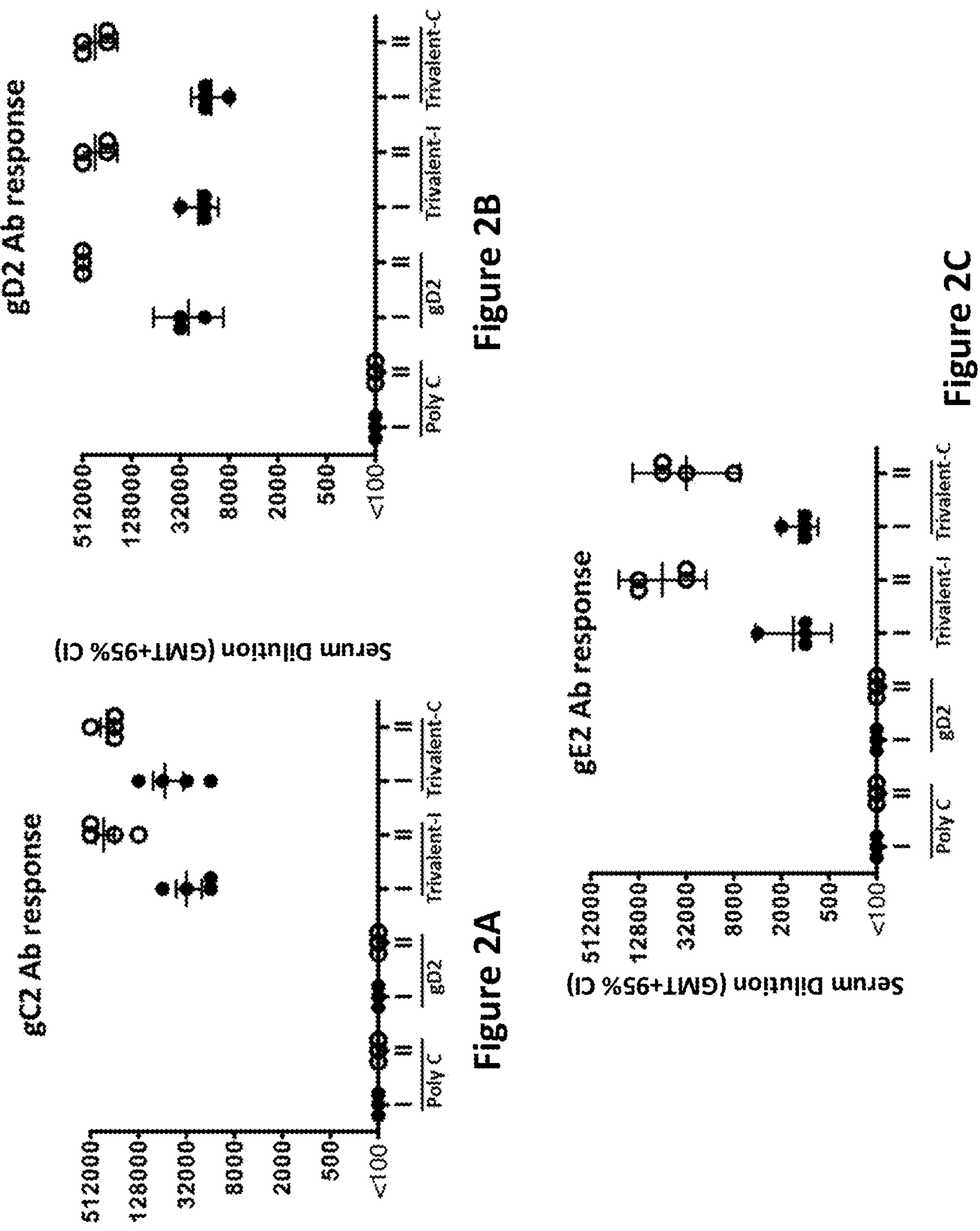
FIG. 2A. gC2 antibody (Ab) response as determined by antigen-specific ELISA in mice immunized with gD2 mRNA; or gC2 mRNA, gD2 mRNA and gE2 mRNA each given at a different intradermal site (Trivalent-I); or gC2 mRNA, gD2 mRNA and gE2 mRNA given in combination (Trivalent-C). I indicates first immunization; II indicates second immunization.
FIG. 2B. gD2 Ab response as determined by antigen-specific ELISA in mice immunized with gD2 mRNA; or gC2 mRNA, gD2 mRNA and gE2 mRNA each given at a different intradermal site (Trivalent-I); or gC2 mRNA, gD2 mRNA and gE2 mRNA given in combination (Trivalent-C). I indicates first immunization; II indicates second immunization.
FIG. 2C. gE2 Ab response as determined by antigen-specific ELISA in mice immunized with gD2 mRNA; or gC2 mRNA, gD2 mRNA and gE2 mRNA each given at a different intradermal site (Trivalent-I); or gC2 mRNA, gD2 mRNA and gE2 mRNA given in combination (Trivalent-C). I indicates first immunization; II indicates second immunization.

Four animals were evaluated in each group. High ELISA titers to each immunogen were obtained after the first immunization (marked as roman numeral I; FIGS. 2A-C), and the titers were boosted even higher after the second immunization (marked as roman numeral II; FIGS. 2A-C). Immunization with gD2 modified mRNA vaccine selectively induced extremely high titers of ELISA antibodies to gD2 (FIG. 2B), while immunization with the trivalent modified mRNA vaccines induced extremely high titers of ELISA antibodies to gC2 (FIG. 2A) and gD2 (FIG. 2B) and high titers to gE2 (FIG. 2C). In all non-control groups, the second immunization significantly boosted the ELISA titers compared to the first. The differences between the titers in the second vs the first immunizations were significant, $p<0.05$ (t-tests, comparing the antibody titers after the first and second immunization).

Conclusion: The gD2 mRNA and gC2, gD2 and gE2 mRNA immunogens induced extremely high titers of ELISA antibodies after the first immunization that were significantly boosted after the second immunization.

Example 4: Balanced $T_H1$ and $T_H2$ Igg Isotypes Produced by Modified mRNA Immunization The ability of mRNA immunizations to stimulate predominantly a $T_H1$ or $T_H2$ immune response was tested by determining whether IgG1 ($T_H2$) or IgG2a ($T_H1$) antibodies are produced. ELISA was performed on plates coated with all three antigens, gC2, gD2 and gE2. Serum obtained after the first or second immunization was added to the antigen-coated plates, and IgG1 or IgG2a was detected using HRP anti-mouse IgG1 or IgG2a. IgG1 (FIG. 3A) and IgG2a (FIG. 3B) titers were significantly elevated after immunization with gD2 and the trivalent modified mRNA vaccines. Further, the IgG1 (FIG. 3A) or IgG2a (FIG. 3B) titers were significantly higher after the second modified mRNA immunization compared to the first, $p<0.05$ (t tests).

Conclusion: The results demonstrate high titers of antibodies are produced to both IgG1 and IgG2a isotypes, indicating a balanced $T_H1$ and $T_H2$ response to immunization with modified gC2, gD2 and gE2 mRNA.

Example 5: High Neutralizing Antibody Titers after Modified mRNA Immunization Serum was obtained 28 days after the second immunization, and neutralizing antibody titers were determined using serial 2-fold dilutions of serum, starting at a 1:25 dilution and 10% human serum as a source of complement. The human serum was obtained from an individual seronegative for HSV-1 and HSV-2. The modified mRNA groups were each significantly different from the poly C controls ($p<0.001$; FIG. 4). While each of the mRNA groups was not significantly different from one another, the trivalent vaccine given as a combined immunogen (Trivalent-C) performed the best of the three mRNA groups (FIG. 4).

Conclusion: Each of the modified mRNA groups produced extremely high titers of neutralizing antibodies in the presence of 10% human complement.

Example 6: $CD4^+$ and $CD8^+$ T Cell Responses in Splenocytes after Modified mRNA Immunization Five animals from the trivalent modified mRNA group that were immunized with each glycoprotein mRNA at a separate site (Trivalent-I group) were euthanized 14 days after the second immunization. Splenocytes were prepared for T cell assays. Splenocytes were stimulated with glycoprotein subunit antigens prepared in baculovirus or 15 amino acid peptides containing 11 overlapping amino acids. The $CD4^+$ and $CD8^+$ T cell responses are shown in FIGS. 5A-5B and FIGS. 6A-6B, respectively.

$CD4^+$ T cells: The modified mRNA-expressed gC2, gD2, and gE2 subunit antigens each stimulated polyfunctional $CD4^+$ T cell responses (FIGS. 5A-5B). Splenocytes harvested from immunized subjects and then stimulated with subunit antigen glycoproteins increased polyfunctional $CD4^+$ T cell responses (FIG. 5A). Splenocytes harvested from immunized subjects and then stimulated with 15 amino acid overlapping peptides increased polyfunctional $CD4^+$ T cell responses and IFNγ responses (FIG. 5B). $CD8^+$ T cells: Only gE peptide pool 2 stimulated a significant IFNγ $CD8^+$ T cell response (FIG. 6B).

Example 7: Survival, Weight Loss and Neurological Signs after Modified mRNA Immunization and Intravaginal Challenge Thirty-three days after the second immunization, animals were inoculated intravaginally with $5\times10^3$ PFU of HSV-2 strain MS (~400 $LD_{50}$). Animals were observed daily for survival, neurological signs consisting of hind limb weakness or paralysis and hunched gait, and for weight loss or gain. All animals in the poly C control group died, while all animals in the gD2 alone, trivalent given individually (labeled Trivalent-I) or trivalent given combined (labeled Trivalent-C) survived (FIG. 7A; $p=0.002$ by Log-rank (Mantel-Cox) comparing the three mRNA/LNP groups with poly C controls). FIG. 7B demonstrates that administration of the modified mRNA vaccine twice at 28 day intervals and challenged intravaginally with HSV-2 does not result in neurological signs or weight loss. Control subjects that were not administered the vaccine and were and challenged intravaginally with HSV-2 showed weight loss and neurological signs.

Each of the mRNA/LNP groups significantly outperformed the control group. All mice immunized with the modified mRNA survived and showed no evidence of weight loss, neurological disease or genital lesions after intravaginal challenge with ~400 $LD_{50}$ of HSV-2.

Example 8: HSV-2 Vaginal Titers after Modified mRNA Immunization and Intravaginal Challenge Vaginal swabs were obtained from 10 animals per group on days 2 and 4 post challenge and cultured for replication competent HSV-2 virus. Results are shown in FIGS. 8A=8B. 9/10 animals in the poly C group had positive cultures on days 2 (FIG. 8A) and 4 (FIG. 8B) compared with 3/10 in the gD2 group and 0/10 in the trivalent-I or trivalent-C groups (P values by Fisher Exact test were not significant comparing trivalent groups to gD2 alone; $p<0.001$ comparing trivalent-I or trivalent-C with poly C; $p=0.02$ comparing gD2 alone with poly C).

Each of the mRNA/LNP groups significantly outperformed the Poly C control group. Remarkably, day 2 and day 4 vaginal titers after challenge were negative in mice immunized with the trivalent mRNA whether given at separate sites or as a combined immunization. No significant differences were detected comparing either trivalent group with gD2 alone, although both trivalent groups outperformed the gD2 alone group, as 3 of 10 mice in the gD2 group had virus isolated from vaginal swabs.

Example 9: Genital Disease after Modified mRNA Immunization and Intravaginal Challenge Animals were monitored daily for genital disease for 28 days post challenge. A score of 0 was assigned for no disease, and 1 point each was assigned for hair loss around the anal or genital orifices, genital erythema, genital exudate, and necrosis of genital tissues (FIG. 9).

No animal in the gD2 or trivalent mRNA/LNP groups developed genital disease, which was significantly different than the poly C controls ($p<0.001$, one-way ANOVA by Kruskal-Wallis test followed by Dunn's multiple comparisons for significance).

Example 10: HSV-2 DNA in Dorsal Root Ganglia after Modified mRNA Immunization and Intravaginal Challenge Five animals per group were euthanized at 4 days post challenge, except for the trivalent-combined group in which four animals were euthanized. Dorsal root ganglia (DRG) were harvested for HSV-2 DNA quantitation by qPCR to detect the Us9 gene. All five animals in the poly C group had HSV-2 DNA detected in the DRG, while 2/5 animals in the gD mRNA, 1/5 in the trivalent mRNA at individual sites, and 1/4 trivalent mRNA given at the same site were positive for HSV-2 DNA (FIG. 10; Mann-Whitney test: gD2 compared with poly C, $p=0.03$; trivalent at different sites compared with poly C, $p<0.01$; trivalent at same site compared with poly C, $p=0.14$). The difference between the modified mRNA immunized groups was not significant.

Conclusion: Dorsal root ganglia were negative for HSV-2 DNA on day 4 after infection in 75% to 80% of animals immunized with gD2 alone or the trivalent vaccine. The trivalent mRNA group at different sites and the gD2 mRNA group significantly outperformed the poly C mRNA control group, while the trivalent mRNA group with all glycoproteins given together did not differ significantly from the poly C group, likely because of the smaller sample size in the trivalent-combined group.

SUMMARY

Modified mRNA vaccines expressing gD2 alone or gC2, gD2 and gE2 provided outstanding protection against HSV-2 genital challenge. The expression of the three proteins slightly outperformed gD2 based on day 2 and day 4 titers after challenge and the lower number of animals with HSV-2 DNA detected in DRG on day 4.

Example 11: T Follicular Helper (Tfh) Cell and Germinal Center B Cell Responses in Immunized Mice BALB/c female mice were left un-immunized as naïve control animals or immunized intradermally twice at 28 day intervals with poly C mRNA-LNP or trivalent modified mRNA-LNP. The poly C mRNA controls received 10 μg Poly C mRNA-LNP divided into 4 aliquots and administered at 4 separate sites. The trivalent modified mRNA group received 10 μg gC2 mRNA-LNP, 10 μg gD2 mRNA-LNP, and 10 μg gE2 mRNA-LNP each divided into 2 aliquots and each given at 2 sites. Two weeks after the second immunization, spleens were harvested from 5 animals per group and flow cytometry performed to detect T follicular helper (Tfh) cells (FIG. 11A; *$p<0.05$) and germinal center B cell responses (FIG. 11B; *$p<0.05$).

Conclusion: The trivalent mRNA-LNP vaccine induced a potent Tfh and germinal center B cell response and significantly outperformed the poly C control immunization ($p<0.05$) and the naïve group ($p<0.05$) for both Tfh and germinal center B cell responses. These immune responses suggest that the trivalent modified mRNA-LNP vaccine will likely induce a durable antibody response.

Example 12: Vaginal Igg Responses to Modified mRNA Immunization in Mice

BALB/c mice were immunized intradermally twice at 28 day intervals with 10 μg of ploy C mRNA-LNP, 10 μg gD2 mRNA-LNP or 10 μg each of gC2, gD2, gE trivalent modified mRNA-LNP. The trivalent mRNA was combined and administered as 10 μg gC2 mRNA & 10 μg gD2 mRNA & 10 μg gE2 mRNA combined into LNP and divided into 4 aliquots and given at 4 sites. One month after the second immunization, 60 μl of media was introduced in the vaginal cavity and retrieved. IgG titers to gC2 (FIG. 12A), gD2 (FIG. 12B), and gE2 (FIG. 12C) were determined at a 1:50 dilution of the vaginal wash fluids by ELISA (FIGS. 12A-12C, n=10 mice in the poly C group, n=10 in the gD2 mRNA group and n=25 in the trivalent mRNA group; *$p<0.001$; $p<0.01$).

Conclusion: The trivalent mRNA produced a robust vaginal IgG response to gC2 (FIG. 12A) and gD2 (FIG. 12B) and a more moderate response to gE2 (FIG. 12C). The gD2 ELISA titers were higher in mice immunized with the modified trivalent mRNA vaccine compared to mice immunized with the modified gD2 mRNA vaccine (FIG. 12B).

Example 13: Antibodies to gC2 Produced by Trivalent mRNA Immunization of Mice Block Immune Evasion Domains on gC2

BALB/c mice were left unimmunized as a source of non-immune IgG, or immunized intradermally with poly C mRNA-LNP or trivalent mRNA-LNP. The poly C mRNA controls received 10 μg poly C mRNA-LNP divided into 4 aliquots and administered at 4 separate sites. The gD2 mRNA group received 10 μg gD2 mRNA-LNP administered as described for the poly C mRNA-LNP. The trivalent modified mRNA group received 10 μg gC2 mRNA-LNP, 10 μg gD2 mRNA-LNP, and 10 μg gE2 mRNA-LNP combined into one LNP and divided into 4 aliquots and given at 4 sites. There were 10 mice in each group. Sera from the 10 mice were pooled and IgG was purified. The IgG was evaluated at 12 g/200 μl for its ability to block complement component C3b binding to gC2. This blocking assay is used to assess whether antibodies produced by immunization block the immune evasion properties of gC2. Non-immune murine IgG, IgG from the poly C mRNA group, and IgG from the gD2 mRNA group each failed to block gC2 binding to C3b. In contrast, IgG from trivalent mRNA-immunized animals totally blocked the interaction between gC2 and C3b (FIG. 13, ****$p<0.0001$).

Conclusions: The trivalent mRNA vaccine produces antibodies that block immune evasion domains on gC2 as determined by blocking the interaction between gC2 and C3b.

Example 14: Intravaginal Infection of Mice at a Higher Inoculum Titer of HSV-2 after Modified mRNA Vaccination BALB/c mice (n=5) were immunized with the trivalent modified mRNA using 10 μg gC2 mRNA-LNP, 10 μg gD2 mRNA-LNP, 10 μg gE2 mRNA-LNP each divided into 2 aliquots and each given individually at 2 sites. One month after the second immunization, mice were treated with medroxyprogesterone and five days later infected intravaginally with $5\times10^4$ PFU HSV-2 strain MS (2,000 $LD_{50}$). Animals were followed for 28 days and evaluated for death, genital disease, vaginal viral titers 2 and 4 days after infection and dorsal root ganglia (DRG) HSV-2 DNA copy number 28 days after infection. No mouse immunized with the trivalent mRNA-LNP vaccine died, had genital disease, had any virus detected on day 2 or 4 post-infection or had HSV-2 DNA detected in DRG (Table 1).

TABLE 1

Trivalent mRNA-LNP immunized mice challenged with HSV-2 strain MS (2,000 $LD_{50}$)

| Disease parameters | Mice | % Protection |
|---|---|---|
| Death | 0/5 | 100 |
| Genital disease | 0/5 | 100 |
| Vaginal viral titers day 2 | 0/5 | 100 |
| Vaginal viral titers day 4 | 0/5 | 100 |
| HSV-2 DNA copies in DRG | 0/5 | 100 |

Conclusions: Mice were infected with HSV-2 at a dose that was 10-fold higher than used in earlier experiments described herein (FIGS. 7A-10). Protection of the mice remained outstanding even at this higher titer challenge. We achieved sterilizing immunity in all five mice as determined by no deaths, no genital disease, negative vaginal virus titers on days 2 and 4 post-infection and no HSV-2 DNA in the lumbosacral DRG on day 28 (Table 1).

Example 15: Evaluation of the Intramuscular Route of Modified mRNA Immunization in Mice BALB/c mice were immunized intramuscularly with poly C mRNA-LNP as a control (15/group) or with trivalent mRNA containing 10 μg each of gC2, gD2 and gE2 mRNA-LNP (20/group). All poly C control animals died by day 12, while all animals in the trivalent mRNA group survived (FIG. 14A). No weight loss occurred in the trivalent mRNA group, while the poly C control animals lost >15% of body weight (FIG. 14B). The poly C group developed extensive genital disease, while the trivalent mRNA animals had no genital disease (FIG. 14C). DRG were harvested from nine poly C animals at the time of euthanasia between days 7 and 12 post-infection or at the end of the experiment on day 28 in the trivalent mRNA group. All animals in the poly C group had HSV-2 DNA detected in DRG, while none were positive for HSV-2 DNA in trivalent mRNA group (FIG. 14D). Day 2 (FIG. 14E) and Day 4 (FIG. 14F) vaginal viral cultures were positive in all 15 animals in the poly C group, while cultures were negative in all 20 animals in the trivalent mRNA group. Differences between poly C and trivalent groups are significant, p<0.001 for each figure (FIGS. 14A-14F).

Conclusions: Trivalent modified mRNA-LNP provides outstanding protection in mice when administered intramuscularly. We reported comparable findings above when mice were immunized intradermally. Overall, we have now evaluated 64 mice that were immunized with trivalent mRNA at 10 μg of each immunogen given either intradermally (FIGS. 7A-10) or intramuscularly (FIGS. 14A-14F). We have achieved sterilizing immunity in 63/64 (98%) mice based on no death, no genital disease, no weight loss, negative day 2 and 4 vaginal titers and negative HSV-2 DNA in DRG.

Example 16: Summary Comparison of Immunization with Trivalent mRNA-LNP and Trivalent Subunit Antigen CPG/Alum in Balb/c Mice The results presented in Table 2 hereinbelow represent a summary of all the results in BALB/c mice that were immunized either intradermally or intramuscularly with trivalent mRNA containing 10 μg each of gC2, gD2 and gE2 mRNA-LNP (total 64 mice studied). We show a comparison with the results obtained in BALB/c mice that were immunized with 5 μg each of bac-gC2(27-426t) containing gC2 amino acids 27-426 from HSV-2 strain 333, bac-gD2(306t) containing gD2 amino acids 26-331 from HSV-1 strain 333, and bac-gE2(24-405t) containing gE2 amino acids 24-405 from HSV-2 strain 2.12. The gC2, gD2, gE2 subunit antigens were mixed with 150 μg CpG and 25 μg alum/per g protein as adjuvants and administered intramuscularly. Mice were immunized twice at 28-day intervals with trivalent mRNA-LNP and three times at 14-day intervals with subunit antigens, as we have done in prior experiments. The mRNA and subunit antigen experiments were performed at the same time. The results summarized in Table 2 demonstrate significant superiority of the trivalent mRNA-LNP vaccine over the trivalent subunit antigen vaccine in many immune response parameters, and most importantly in vaccine efficacy. The trivalent mRNA-LNP vaccine achieved sterilizing immunity in 63/64 (98%) of mice compared to 15/20 (75%) in the subunit antigen group.

TABLE 2

Comparisons of immunization with trivalent mRNA-LNP or trivalent subunit antigen CpG/alum in BALB/c mice.

| Comparison | Trivalent mRNA | Trivalent subunit antigen | P value |
|---|---|---|---|
| Serum IgG ELISA | | | |
| gC2 | 1:256,000 | 1:32,000 | p < 0.001 |
| gD2 | 1:512,000 | 1:128,000 | p < 0.01 |
| gE2 | 1:64,000 | 1:16,000 | p < 0.05 |
| Vaginal fluid IgG ELISA OD at 405 nm tested at 1:50 dilution | | | |
| gC2 | 1.6 OD | 0.6 OD | p < 0.001 |
| gD2 | 1.5 OD | 1.0 OD | p < 0.05 |
| gE2 | 0.5 OD | 0.25 OD | p < 0.01 |
| Serum neutralizing antibody | | | |
| Against HSV-2 | 1:4,800 | 1:1,600 | p < 0.01 |
| Against HSV-1 | 1:6,400 | 1:4,000 | p = NS* |
| Blocking C3b binding to gC2 | Total blocking | Total blocking | p = NS |
| $CD4^+$ T cell responses | Significant responses for gC2, gD2 and gE2 | Significant response only for gD2 | Trivalent mRNA more potent |
| $CD8^+$ T cell responses | Significant response for gE2 | No significant responses | Trivalent mRNA more potent |
| Achieving sterilizing immunity# | 63/64 (98%) mice | 15/20 (75%) mice | p < 0.01 |

*NS, not significant;

#Sterilizing immunity defined as no death, no genital disease, no weight loss, and no evidence of subclinical infection as measured by day 2 and day 4 vaginal cultures post-infection and HSV-2 DNA in dorsal root ganglia on day 4 or day 28 post-infection.

Example 17: Evaluation of the Trivalent mRNA-LNP Vaccine in Guinea Pigs

Hartley Strain female guinea pigs were left unimmunized and uninfected (naive group, n=10), immunized three times intradermally at monthly intervals with 20 μg poly C mRNA-LNP (n=10) or with 20 μg each of gC2, gD2, gE modified mRNA-LNP (n=10). One month after the final immunization, animals in the poly C and trivalent mRNA groups were infected intravaginally with $5\times10^5$ PFU of HSV-2 strain MS (50 $LD_{50}$). Animals were observed for death, genital lesions during the acute phase of infection (days 1-14) and genital lesions during the recurrent phase of infection (days 15-60). In the poly C control group, 7/10 animals died or were humanly euthanized between days 7 and 20 post-infection, while no animal in the trivalent group and no naïve (uninfected) animal died (FIG. 15A). The poly C group had genital lesions on a mean of 6.4 days during the acute phase of infection with 9/10 animals developing acute genital disease, while no animal in the trivalent group or naïve (uninfected) group developed acute genital disease (FIG. 15B). The poly C animals had genital lesions on a mean of 3.7 days during the recurrent phase of infection from days 15-60, with 2/3 animals developing recurrent genital lesions (FIG. 15C). In contrast, the trivalent immunized guinea pigs and the naïve (uninfected) animals had no recurrent genital lesions (FIG. 15C).

Conclusions: Trivalent modified mRNA-LNP provided outstanding protection against acute and recurrent genital lesions in guinea pigs.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

All patent documents and references cited herein are incorporated by reference as if fully set forth.

The invention claimed is:

1. A composition comprising a plurality of RNAs encoding HSV antigens, wherein the plurality of RNAs consist of:

(a) RNA encoding an immunogenic fragment of a Herpes Simplex Virus (HSV) glycoprotein D (gD), wherein the immunogenic fragment consists of a sequence that is at least 95% identical to SEQ ID NO: 5;

(b) RNA encoding an immunogenic fragment of an HSV glycoprotein C (gC), wherein the immunogenic fragment consists of a sequence that is at least 95% identical to SEQ ID NO: 11; and (c) RNA encoding an immunogenic fragment of an HSV glycoprotein E (gE), wherein the immunogenic fragment consists of a sequence that is at least 95% identical to SEQ ID NO: 17;

wherein one or more of said RNAs is a nucleoside modified RNA.

2. The composition of claim 1, wherein said nucleoside modified RNA comprises one or more pseudouridine residues.

3. The composition of claim 2, wherein said one or more pseudouridine residues comprise m1Ψ (1-methylpseudouridine), m1acp3Ψ (1-methyl-3-(3-amino-5-carboxypropyl) pseudouridine, Ψm (2'-O-methylpseudouridine, m5D (5-methyldihydrouridine), m3Ψ (3-methylpseudouridine), or any combination thereof.

4. The composition of claim 1, wherein said RNA further comprises:

(i) a poly-A tail;

(ii) an m7GpppG cap, 3'-O-methyl-m7GpppG cap, or anti-reverse cap analog;

(iii) a cap-independent translational enhancer;

(iv) 5' and 3' untranslated regions that enhance translation; or (v) a combination thereof.

5. A method of treating a Herpes Simplex Virus (HSV) infection or suppressing, inhibiting, or reducing the incidence of an HSV infection in a subject, the method comprising the step of administering a composition to said subject, wherein the composition comprises a plurality of RNAs encoding HSV antigens, wherein the plurality of RNAs consist of:

(a) RNA encoding an immunogenic fragment of a Herpes Simplex Virus (HSV) glycoprotein D (gD), wherein the immunogenic fragment consists of a sequence that is at least 95% identical to SEQ ID NO: 5;

(b) RNA encoding an immunogenic fragment of an HSV glycoprotein C (gC), wherein the immunogenic fragment consists of a sequence that is at least 95% identical to SEQ ID NO: 11; and (c) RNA encoding an immunogenic fragment of an HSV glycoprotein E (gE), wherein the immunogenic fragment consists of a sequence that is at least 95% identical to SEQ ID NO: 17;

wherein one or more of said RNAs is a nucleoside modified RNA.

6. The method of claim 5, wherein said HSV infection comprises an HSV-1 infection or an HSV-2 infection.

7. The method of claim 5, wherein said HSV infection comprises a primary HSV infection; a flare, recurrence, or HSV labialis following a primary HSV infection; a reactivation of a latent HSV infection; an HSV encephalitis; an HSV neonatal infection; a genital HSV infection; an oral HSV infection; or a combination thereof.

8. The method of claim 5, wherein the administration step comprises intramuscular, subcutaneous, intradermal, intranasal, intravaginal, intrarectal, or topical administration.

9. A method of inducing an immune response in a subject, comprising the step of administering a composition to said subject, wherein the composition comprises a plurality of RNAs encoding HSV antigens, wherein the plurality of RNAs consist of:

(a) RNA encoding an immunogenic fragment of a Herpes Simplex Virus (HSV) glycoprotein D (gD);

(b) RNA encoding an immunogenic fragment of an HSV glycoprotein C (gC); and (c) RNA encoding an immunogenic fragment of an HSV glycoprotein E (gE);

wherein one or more of said RNAs is a nucleoside modified RNA.

10. The method of claim 9, wherein said immune response comprises a CD4 immune response; a CD8 immune response; a T follicular helper cell immune response; a germinal center B cell immune response; an IgG antibody response; or a combination thereof.

11. The composition of claim 1, comprising:

(a) RNA encoding an immunogenic fragment of an gD and a signal sequence;

(b) RNA encoding an immunogenic fragment of an HSV gC and a signal sequence; and (c) RNA encoding an immunogenic fragment of an HSV gE and a signal sequence.

12. The composition of claim 11, wherein the signal sequence of (b) is not a naturally occurring HSV gC signal sequence and/or the signal sequence of (c) is not a naturally occurring HSV gE signal sequence.

13. The composition of claim 11, wherein the signal sequence of (b) and/or the signal sequence of (c) comprises the nucleotide sequence of

```
                                        (SEQ ID NO: 20)
AUGCGCAUGCAGCUGCUGCUGCUGAUCGCCCUGUCCCUGGCCCUGGUGA
CCAACUCC.
```

14. The composition of claim 1, wherein the composition does not include RNA encoding immunogenic fragments of any HSV antigen that is not HSV gD, HSV gC, or HSV gE.

15. The composition of claim 1, wherein the composition does not include RNA encoding an immunogenic fragment of an HSV glycoprotein B (gB), an HSV glycoprotein H (gH), an HSV glycoprotein L (gL), or an HSV glycoprotein I (gI).

16. The composition of claim 1, wherein the composition further comprises a nanoparticle, lipid, polymer, cholesterol, and/or cell penetrating peptide.

17. The composition of claim 16, wherein the nanoparticle is a lipid nanoparticle (LNP).

* * * * *